United States Patent
Juhl et al.

(10) Patent No.: US 10,618,913 B2
(45) Date of Patent: Apr. 14, 2020

(54) MACROCYCLES AS PDE1 INHIBITORS

(71) Applicant: H. Lundbeck A/S, Valby (DK)

(72) Inventors: Karsten Juhl, Greve (DK); Mikkel Jessing, Frederiksberg (DK); Morten Langgård, Glostrup (DK); Paulo Jorge Vieira Vital, København V (DK); Jan Kehler, Lyngby (DK); Lars Kyhn Rasmussen, Vanløse (DK); Carl Martin Sebastian Clementson, Valby (DK); Mauro Marigo, Skovlunde (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 16/217,754

(22) Filed: Dec. 12, 2018

(65) Prior Publication Data

US 2019/0185489 A1 Jun. 20, 2019

(30) Foreign Application Priority Data

Dec. 20, 2017 (DK) .......................... PA 2017 00731

(51) Int. Cl.
| | | |
|---|---|---|
| *C07D 498/22* | (2006.01) | |
| *A61K 31/4375* | (2006.01) | |
| *A61P 25/28* | (2006.01) | |
| *A61K 31/437* | (2006.01) | |
| *C07D 519/00* | (2006.01) | |
| *C07D 471/04* | (2006.01) | |

(52) U.S. Cl.
CPC .......... *C07D 498/22* (2013.01); *A61K 31/437* (2013.01); *A61K 31/4375* (2013.01); *A61P 25/28* (2018.01); *C07D 471/04* (2013.01); *C07D 519/00* (2013.01)

(58) Field of Classification Search
CPC .. C07D 471/04; C07D 519/00; A61K 31/437; A61P 25/28
USPC .................................. 540/468, 469; 514/183
See application file for complete search history.

(56) References Cited

U.S. PATENT DOCUMENTS

| | | |
|---|---|---|
| 10,034,861 B2 | 7/2018 | Kehler et al. |
| 10,351,561 B2 | 7/2019 | Kehler et al. |
| 2016/0083391 A1 | 3/2016 | Burdi et al. |
| 2016/0083400 A1 | 3/2016 | Burdi et al. |
| 2018/0000786 A1 | 1/2018 | Kehler et al. |
| 2018/0179200 A1 | 6/2018 | Kehler et al. |
| 2019/0105302 A1 | 4/2019 | Kehler et al. |
| 2019/0194189 A1 | 6/2019 | Juhl et al. |
| 2019/0352302 A1 | 11/2019 | Kehler et al. |

FOREIGN PATENT DOCUMENTS

| | | |
|---|---|---|
| WO | WO 2006/044821 A1 | 4/2006 |
| WO | WO 2008/070095 A1 | 6/2008 |
| WO | WO 2008/111010 A1 | 9/2008 |
| WO | WO 2010/065153 A1 | 6/2010 |
| WO | WO 2013/142307 A1 | 9/2013 |
| WO | WO 2016/042775 A1 | 3/2016 |
| WO | WO 2016/055618 A1 | 4/2016 |
| WO | WO 2016/147659 A1 | 9/2016 |
| WO | WO 2016/170064 A1 | 10/2016 |
| WO | WO 2017/172795 A1 | 10/2017 |
| WO | WO 2018/007249 A2 | 1/2018 |

OTHER PUBLICATIONS

U.S. Appl. No. 16/033,395, filed Jul. 12, 2018, Pending.
U.S. Appl. No. 15/849,798, filed Dec. 21, 2017, Published, 2018-0179200.
U.S. Appl. No. 16/218,019, filed Dec. 12, 2018, Pending.
PCT/EP2017/066255, Aug. 25, 2017, International Search Report and Written Opinion.
PCT/EP2017/083721, Feb. 7, 2018, International Search Report and Written Opinion.
PCT/EP2018/085728, Feb. 11, 2019, International Search Report and Written Opinion.
PCT/EP2018/085798, Feb. 13, 2019, International Search Report and Written Opinion.
International Search Report and Written Opinion dated Aug. 25, 2017 for Application No. PCT/EP2017/066255.
International Search Report and Written Opinion dated Feb. 7, 2018 for Application No. PCT/EP2017/083721.
International Search Report and Written Opinion dated Feb. 11, 2019 for Application No. PCT/EP2018/085728.
International Search Report and Written Opinion dated Feb. 13, 2019 for Application No. PCT/EP2018/085798.
Bernard et al., Transcriptional architecture of the primate neocortex. Neuron. Mar. 22, 2012;73(6):1083-99.
Blokland et al., PDE Inhibition and Cognition Enhancement. Expert Opinion Thera. Patents. 2012; 22(4):349-354.
Francis et al., Mammalian cyclic nucleotide phosphodiesterases: molecular mechanisms and physiological functions. Physiol Rev. Apr. 2011;91(2):651-90.

(Continued)

*Primary Examiner* — Deepak R Rao
(74) *Attorney, Agent, or Firm* — Wolf, Greenfield & Sacks, P.C.

(57) ABSTRACT

The present invention provides macrocycles of formula (I) as PDE1 inhibitors and their use as a medicament, in particular for the treatment of neurodegenerative disorders and psychiatric disorders.

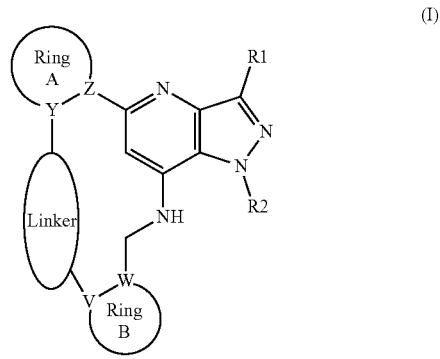

(I)

19 Claims, No Drawings

(56) References Cited

OTHER PUBLICATIONS

Medina, Therapeutic Utility of Phosphodiesterase Type I Inhibitors in Neurological Conditions. Front Neurosci. 2011; 5: 21.
Yamamoto et al., The effects of a novel phosphodiesterase 7A and -4 dual inhibitor, YM-393059, on T-cell-related cytokine production in vitro and in vivo. Eur J Pharmacol. Jul. 10, 2006;541(1-2):106-14.
U.S. Appl. No. 15/637,920, filed Jun. 29, 2017, Granted, U.S. Pat. No. 10,034,861.
U.S. Appl. No. 16/033,395, filed Jul. 12, 2018, Allowed, 2019-0105302.
U.S. Appl. No. 16/670,408, filed Oct. 31, 2019, Pending.
U.S. Appl. No. 15/849,798, filed Dec. 21, 2017, Granted, U.S. Pat. No. 10,351,561.
U.S. Appl. No. 16/424,585, filed May 29, 2017, Published, 2019-0352302.
U.S. Appl. No. 16/218,019, filed Dec. 12, 2018, Published, 2019-0194189.

MACROCYCLES AS PDE1 INHIBITORS

CROSS-REFERENCE TO RELATED APPLICATION

Foreign priority benefits are claimed under 35 U.S.C. § 119(a)-(d) or 35 U.S.C. § 365(b) of Danish application number PA201700731, filed Dec. 20, 2017. The entire contents of this application is incorporated herein by reference in its entirety.

FIELD OF THE INVENTION

The present invention provides compounds that are PDE1 enzyme inhibitors and their use as a medicament, in particular for the treatment of neurodegenerative disorders and psychiatric disorders. The present invention also provides pharmaceutical compositions comprising compounds of the invention and methods of treating disorders using the compounds of the invention.

BACKGROUND OF THE INVENTION

The second messenger cyclic Nucleotides (cNs), cyclic adenosine monophosphate (cAMP) and cyclic guanosine monophosphate (cGMP) play a major role in intracellular signal transduction cascade, by regulating cN-dependent protein kinases (PKA and PKG), EPACs (Exchange Protein Activated by cAMP), phosphoprotein phosphatases, and/or cN-gated cation channels. In neurons, this includes the activation of cAMP- and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by phosphodiesterases (PDEs, EC 3.1.4.17). PDEs are bimetallic hydrolases that inactivate cAMP/cGMP by catalytic hydrolysis of the 3'-ester bond, forming the inactive 5'-monophosphate. Since PDEs provide the only means of degrading the cyclic nucleotides cAMP and cGMP in cells, PDEs play an essential role in cyclic nucleotide signalling. The catalytic activities of PDEs provide for breakdown of cNs over a spectrum of cN-concentrations in all cells, and their varied regulatory mechanisms provide for integration and crosstalk with myriads of signalling pathways. Particular PDEs are targeted to discrete compartments within cells where they control cN level and sculpt microenvironments for a variety of cN signalosomes (Sharron H. Francis, Mitsi A. Blount, and Jackie D. Corbin. Physiol Rev 2011, 91: 651-690).

On the basis of substrate specificity, the PDE families can be divided into three groups: 1) The cAMP-specific PDEs, which include PDE4, PDE7, and PDE8, 2) the cGMP-selective enzymes PDE5 and PDE9, and 3) the dual-substrate PDEs, PDE1, PDE2, PDE3, as well as PDE10 and PDE11.

Previously named calmodulin-stimulated PDE (CaM-PDE), PDE1 is unique in that it is $Ca^{2+}$-dependently regulated via calmodulin (CaM, a 16 kDa $Ca^{2+}$-binding protein) complexed with four $Ca^{2+}$ (for review, Sharron H. Francis, Mitsi A. Blount, and Jackie D. Corbin. Physiol Rev 2011, 91: 651-690). Thus, PDE1 represents an interesting regulatory link between cyclic nucleotides and intracellular $Ca^{2+}$. The PDE1 family is encoded by three genes: PDE1A (mapped on human chromosome 2q32), PDE1B (human chromosome location, hcl: 12q13) and PDE1C (hcl: 7p14.3). They have alternative promoters and give rise to a multitude of proteins by alternative splicing which differ in their regulatory properties, substrate affinities, specific activities, activation constants for CaM, tissue distribution and molecular weights. More than 10 human isoforms are identified. Their molecular weights vary from 58 to 86 kDa per monomer. The N-terminal regulatory domain contains two $Ca^{2+}$/CaM binding domains and two phosphorylation sites and different splice variants have different variations of the N-terminal domain, which can give proteins with different amino acid sequence with different biochemical functions. PDE1 is a dual substrate PDE and the PDE1C-subtype has equal activity towards cAMP and cGMP (Km≈1-3 µM), whereas the subtypes PDE1A and PDE1B have a preference for cGMP (Km for cGMP≈1-3 µM and for cAMP≈10-30 µM).

The PDE1 subtypes are highly enriched in the brain and located especially in the striatum (PDE1B), hippocampus (PDE1A) and cortex (PDE1A) and this localization is conserved across species (Amy Bernard et al. Neuron 2012, 73, 1083-1099). In the cortex, PDE1A is present mainly in deep cortical layers 5 and 6 (output layers), and used as a specificity marker for the deep cortical layers. PDE1 inhibitors enhance the levels of the second messenger cNs leading to enhanced neuronal excitability.

Thus, PDE1 is a therapeutic target for regulation of intracellular signalling pathways, preferably in the nervous system and PDE1 inhibitors can enhance the levels of the second messenger's cAMP/cGMP leading to modulation of neuronal processes and to the expression of neuronal plasticity-related genes, neurotrophic factors, and neuroprotective molecules. These neuronal plasticity enhancement properties together with the modulation of synaptic transmission make PDE1 inhibitors good candidates as therapeutic agents in many neurological and psychiatric conditions. The evaluation of PDE1 inhibitors in animal models (for reviews see e.g. Blokland et al. Expert Opinion on Therapeutic Patents (2012), 22(4), 349-354; and Medina, A. E. Frontiers in Neuropharmacology (2011), 5 (February), 21) has suggested the potential for the therapeutic use of PDE1 inhibitors in neurological disorders, like e.g. Alzheimer's, Parkinson's and Huntington's Diseases and in psychiatric disorders like e.g. Attention Deficit Hyperactivity Disorder (ADHD), depression, anxiety, narcolepsy, cognitive impairment and cognitive impairment associated with schizophrenia (CIAS) and in restless leg syndrome. There have also been patent applications claiming that PDE1 inhibitors are useful in diseases that may be alleviated by the enhancement of progesterone-signalling such as female sexual dysfunction (e.g. WO 2008/070095).

Current treatments for neurodegenerative and/or psychiatric disorders are not efficacious in all patients. Hence, there remains a need for alternative methods of treatment of such diseases and for this purpose PDE1 inhibitors may be a good alternative. The present invention discloses new compounds with PDE1 inhibitor activity and good physicochemical properties as alternatives to known PDE1 inhibitors.

SUMMARY OF THE INVENTION

PDE1 enzymes are expressed in the Central Nervous System (CNS), making this gene family an attractive source of new targets for the treatment of psychiatric and neurodegenerative disorders.

Accordingly, the present invention relates to a compound according to formula (I)

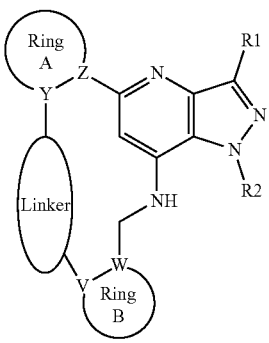

(I)

wherein
ring A is a 5 or 6 membered heteroaromatic ring or ring A is phenyl, and
there is 1 bond between Y and Z;
ring B is a 5 or 6 membered heteroaromatic ring or ring B is phenyl, and
there is 1 bond between V and W;
when ring A is a 5 membered heteroaromatic ring, then one of Y and Z is C and the other is N, or Y=Z=C;
when ring A is a 6 membered heteroaromatic ring or phenyl, then Y=Z=C;
when ring B is a 5 membered heteroaromatic ring, then one of V and W is C and the other is N, or V=W=C;
when ring B is a 6 membered heteroaromatic ring or phenyl, then V=W=C;
the linker is a 5-7 membered saturated chain wherein the atoms consisting of carbon and optionally one or more oxygen, with the proviso that the chain contains no O—O bond, and with the proviso that the bond to V cannot be an O—N bond, and with the proviso that the bond to Y cannot be an O—N bond;
R1 is selected from the group consisting of hydrogen, linear or branched $C_{1-4}$ alkyl and saturated monocyclic $C_{3-4}$ cycloalkyl, wherein said linear or branched $C_{1-4}$ alkyl and saturated monocyclic $C_{3-4}$ cycloalkyl can be optionally substituted with one or more halogen;
R2 is selected from the group consisting of linear or branched $C_{1-6}$ alkyl, saturated monocyclic $C_{3-6}$ cycloalkyl, oxetanyl, tetrahydrofuranyl and tetrahydropyranyl, all of which can optionally be substituted with one or more halogen;
or a pharmaceutically acceptable salt thereof.

Reference to compounds encompassed by the present invention includes the free base and pharmaceutically acceptable salts of the compounds, such as acid addition salts of the compounds, racemic mixtures of the compounds, or the corresponding enantiomer and/or optical isomer of the compounds for which this is relevant, and polymorphic and amorphic forms of compounds of the present invention and of pharmaceutically acceptable salts of said compounds, as well as tautomeric forms the compounds for which this is relevant. Furthermore, the compounds of the present invention and pharmaceutically acceptable salts thereof may potentially exist in unsolvated as well as in solvated forms with pharmaceutically acceptable solvents such as water, ethanol and the like. Both solvated and unsolvated forms of the compounds and pharmaceutically acceptable salts thereof are encompassed by the present invention.

In one embodiment, the invention relates to a compound according to formula (I) or a pharmaceutically acceptable salt thereof for use in therapy.

In one embodiment, the invention relates to a compound according to formula (I) or a pharmaceutically acceptable salt thereof, for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

In one embodiment, the invention relates to a pharmaceutical composition comprising a compound according formula (I) or a pharmaceutically acceptable salt thereof, and one or more pharmaceutically acceptable carrier and/or excipient.

In one embodiment, the invention relates to a method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to formula (I) or a pharmaceutically acceptable salt thereof, to a patient in need thereof.

In one embodiment, the invention relates to the use of a compound according to formula (I) or a pharmaceutically acceptable salt thereof, in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

Definitions

PDE1 Enzymes:
The PDE1 isozyme family includes numerous splice variant PDE1 isoforms. It has three subtypes, PDE1A, PDE1B and PDE1C which divide further into various isoforms. In the context of the present invention PDE1 and PDE1 enzymes are synonymous and refer to PDE1A, PDE1B and PDE1C enzymes as well as their isoforms unless otherwise specified.
PDE1 Inhibitors:
In the context of the present invention, a compound is considered to be a PDE1 inhibitor if the amount required to reach the $IC_{50}$ level of one or more of the three PDE1 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less.

Preferred compounds of the invention exhibit selectivity towards the PDE1B isoform meaning that said compounds are stronger as PDE1B inhibitors than as PDE1A and/or PDE1C inhibitors. In preferred embodiments, said compounds are at least two-fold stronger, five-fold stronger or ten-fold stronger as PDE1B inhibitors than as PDE1A and/or PDE1C inhibitors. In more preferred embodiments, said compounds are at least fifteen-fold stronger or twenty-fold stronger as PDE1B inhibitors than as PDE1A and/or PDE1C inhibitors.

In preferred embodiments, the required amount of PDE1 inhibitor required to reach the $IC_{50}$ level of PDE1B is 400 nM or less, such as 300 nM or less, 200 nM or less, 100 nM or less, or even 80 nM or less, such as 50 nM or less, for example 25 nM or less. Selectivity towards the PDE1B isoform may prevent potentially unwanted effects associated with PDE1A and/or PDE1C inhibition. For example, potentially unwanted peripheral effects.

Substituents:

In the present context, "optionally substituted" means that the indicated moiety may or may not be substituted, and when substituted is mono-, di-, or tri-substituted. It is understood that where no substituents are indicated for an "optionally substituted" moiety, then the position is held by a hydrogen atom.

As used in the context of the present invention, the terms "halo" and "halogen" are used interchangeably and refer to fluorine, chlorine, bromine or iodine. In a preferable embodiment, "halogen" refers to fluorine.

A given range may interchangeably be indicated with "-" (dash) or "to", e.g. the term "$C_{1-3}$ alkyl" is equivalent to "$C_1$ to $C_3$ alkyl".

The terms "$C_{1-3}$ alkyl", "$C_{1-4}$ alkyl", "$C_{1-5}$ alkyl", "$C_{1-6}$ alkyl", refer to a linear (i.e. unbranched) or branched saturated hydrocarbon having from one up to eight carbon atoms, inclusive. Examples of such groups include, but are not limited to, methyl, ethyl, 1-propyl, 2-propyl, 1-butyl, 2-butyl, 2-methyl-2-propyl, 2-methyl-1-butyl and n-hexyl.

The term saturated monocyclic $C_{3-6}$ cycloalkyl refers to cyclopropyl, cyclobutyl, cyclopentyl and cyclohexyl.

The term "5-membered heteroaromatic ring" refers to a 5 membered aromatic monocyclic ring containing 1 to 4 carbon atoms and one or more heteroatoms selected from oxygen, nitrogen and sulfur. Examples include, but are not limited to thiazolyl, oxazolyl, isoxazolyl, triazolyl, pyrazolyl, tetrazolyl, imidazolyl, oxadiazolyl, thiadiazolyl and thiophenyl.

The term "6-membered heteroaromatic ring" refers to a 6 membered aromatic monocyclic ring containing 1 to 5 carbon atoms and one or more heteroatoms selected from oxygen, nitrogen and sulfur, preferably nitrogen. Examples include, but are not limited to pyridinyl, pyrimidinyl and pyrazinyl. Particular mention is made of pyridinyl and pyrazinyl.

Isomeric and Tautomeric Forms:

When compounds of the present invention contain one or more chiral centers reference to any of the compounds will, unless otherwise specified, cover the enantiomerically or diastereomerically pure compound as well as mixtures of the enantiomers or diastereomers in any ratio.

Furthermore, some of the compounds of the present invention may exist in different tautomeric forms and it is intended that any tautomeric forms that the compounds are able to form are included within the scope of the present invention.

Pharmaceutically Acceptable Salts:

The compounds of this invention are generally utilized as the free substance or as a pharmaceutically acceptable salt thereof. When a compound of formula (I) contains a free base, such salts are prepared in a conventional manner by treating a solution or suspension of a free base of formula (I) with a molar equivalent of a pharmaceutically acceptable acid. Representative examples of suitable organic and inorganic acids are described below.

Pharmaceutically acceptable salts in the present context is intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid, salicylic acid, saccharin and sulfonic acids, such as methanesulfonic acid, ethanesulfonic acid, toluenesulfonic acid and benzenesulfonic acid. Some of the acids listed above are di- or tri-acids, i.e. acids containing two or three acidic hydrogens, such as phosphoric acid, sulphuric acid, fumaric acid and maleic acid.

Additional examples of useful acids and bases to form pharmaceutically acceptable salts can be found e.g. in Stahl and Wermuth (Eds) "Handbook of Pharmaceutical salts. Properties, selection, and use", Wiley-VCH, 2008.

Therapeutically Effective Amount:

In the present context, the term "therapeutically effective amount" of a compound means an amount sufficient to alleviate, arrest, partly arrest, remove or delay the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

Treatment and Treating:

In the present context, "treatment" or "treating" is intended to indicate the management and care of a patient for the purpose of alleviating, arresting, partly arresting, removing or delaying progress of the clinical manifestation of the disease. The patient to be treated is preferably a mammal, in particular a human being.

Combinations

In one embodiment of the invention, the compound of formula (I) is for use as stand-alone treatment as the sole active compound.

In another embodiment of the invention, the compound of formula (I) may be used in combination with a second compound, wherein said second compound is selected from the following: a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

In yet another embodiment of the invention, the compound of formula (I) may be used in combination with a second compound, wherein said second compound is a compound that is useful in the treatment of a psychiatric disorder.

The terms "combined use", "in combination with" and "a combination of" and the like as used herein in the context of the method of the invention comprising the combined administration of therapeutically effective amounts of a compound of formula (I), and another pharmaceutically active compound, is intended to mean the administration of a compound of formula (I) simultaneously or sequentially, in any order, together with said second compound.

The two compounds may be administered simultaneously or with a time gap between the administrations of the two compounds. The two compounds may be administered either as part of the same pharmaceutical formulation or composition, or in separate pharmaceutical formulations or compositions. The two compounds may be administered on the same day or on different days. They may be administered by the same route, such for example by oral administration, by depot, by intramuscular injection or intravenous injection; or by different routes wherein one compound is for example administered orally or placed by depot and the other compound is for example injected. The two compounds may be administered by the same dosage regime or interval, such as once or twice daily, weekly, or monthly; or by different dosage regimes for example wherein one is administered once daily and the other is administered twice daily or weekly or monthly.

In some instances, the patient to be treated may already be in treatment with one or more of said second compound when treatment with a compound of formula (I) is initiated. In other instances, the patient may already be in treatment with a compound of formula (I) when treatment with one or more of said second compound is initiated. In other instances, the treatment with a compound of formula (I) and treatment with one or more of said second compound is initiated at the same time.

Compounds for Combination Treatment

In the context of the invention, compounds to be used in combination with a compound of formula (I) in the treatment of a neurodegenerative disorder, are selected from for example a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

In the context of the invention, compounds to be used in combination with a compound of formula (I) in the treatment of a psychiatric and/or cognitive disorder, is a compound with a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor. Examples of such compounds includes clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

Administration Routes:

Pharmaceutical compositions comprising a compound of the present invention either as the sole active compound or in combination a second compound defined above, may be specifically formulated for administration by any suitable route such as the oral, rectal, nasal, buccal, sublingual, transdermal and parenteral (e.g. subcutaneous, intramuscular, and intravenous) route; the oral route being preferred.

It will be appreciated that the route will depend on the general condition and age of the subject to be treated, the nature of the condition to be treated and the active ingredient.

Pharmaceutical Formulations and Excipients:

In the following, the term, "excipient" or "pharmaceutically acceptable excipient" refers to pharmaceutical excipients including, but not limited to, fillers, antiadherents, binders, coatings, colours, disintegrants, flavours, glidants, lubricants, preservatives, sorbents, sweeteners, solvents, vehicles and adjuvants.

The present invention also provides a pharmaceutical composition comprising a compound of formula (I), such as one of the compounds disclosed in the Experimental Section herein. The present invention also provides a process for making a pharmaceutical composition comprising a compound of formula (I). The pharmaceutical compositions according to the invention may be formulated with pharmaceutically acceptable excipients in accordance with conventional techniques such as those disclosed in Remington, "The Science and Practice of Pharmacy", $22^{th}$ edition (2012), Edited by Allen, Loyd V., Jr.

Pharmaceutical compositions for oral administration include solid oral dosage forms such as tablets, capsules, powders and granules; and liquid oral dosage forms such as solutions, emulsions, suspensions and syrups as well as powders and granules to be dissolved or suspended in an appropriate liquid.

Solid oral dosage forms may be presented as discrete units (e.g. tablets or hard or soft capsules), each containing a predetermined amount of the active ingredient, and preferably one or more suitable excipients. Where appropriate, the solid dosage forms may be prepared with coatings such as enteric coatings or they may be formulated so as to provide modified release of the active ingredient such as delayed or extended release according to methods well known in the art. Where appropriate, the solid dosage form may be a dosage form disintegrating in the saliva, such as for example an orodispersible tablet.

Examples of excipients suitable for solid oral formulation include, but are not limited to, microcrystalline cellulose, corn starch, lactose, mannitol, povidone, croscarmellose sodium, sucrose, cyclodextrin, talcum, gelatin, pectin, magnesium stearate, stearic acid and lower alkyl ethers of cellulose. Similarly, the solid formulation may include excipients for delayed or extended release formulations known in the art, such as glyceryl monostearate or hypromellose. If solid material is used for oral administration, the formulation may for example be prepared by mixing the active ingredient with solid excipients and subsequently compressing the mixture in a conventional tableting machine; or the formulation may for example be placed in a hard capsule e.g. in powder, pellet or mini tablet form. The amount of solid excipient will vary widely but will typically range from about 25 mg to about 1 g per dosage unit.

Liquid oral dosage forms may be presented as for example elixirs, syrups, oral drops or a liquid filled capsule. Liquid oral dosage forms may also be presented as powders for a solution or suspension in an aqueous or non-aqueous liquid. Examples of excipients suitable for liquid oral formulation include, but are not limited to, ethanol, propylene glycol, glycerol, polyethylenglycols, poloxamers, sorbitol, poly-sorbate, mono and di-glycerides, cyclodextrins, coconut oil, palm oil, and water. Liquid oral dosage forms may for example be prepared by dissolving or suspending the active ingredient in an aqueous or non-aqueous liquid, or by incorporating the active ingredient into an oil-in-water or water-in-oil liquid emulsion.

Further excipients may be used in solid and liquid oral formulations, such as colourings, flavourings and preservatives etc.

Pharmaceutical compositions for parenteral administration include sterile aqueous and nonaqueous solutions, dispersions, suspensions or emulsions for injection or infusion, concentrates for injection or infusion as well as sterile powders to be reconstituted in sterile solutions or dispersions for injection or infusion prior to use. Examples of excipients suitable for parenteral formulation include, but are not limited to water, coconut oil, palm oil and solutions of cyclodextrins. Aqueous formulations should be suitably buffered if necessary and rendered isotonic with sufficient saline or glucose.

Other types of pharmaceutical compositions include suppositories, inhalants, creams, gels, dermal patches, implants and formulations for buccal or sublingual administration.

It is requisite that the excipients used for any pharmaceutical formulation comply with the intended route of administration and are compatible with the active ingredients.

Doses:

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 0.1-1000 mg/day of a compound of the present invention, such as 1-500 mg/day, such as 1-100 mg/day or 1-50 mg/day. Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

DETAILED DESCRIPTION OF THE INVENTION

The present inventors have identified compounds that are PDE1 inhibitors, and as such are useful to treat neurodegenerative and psychiatric disorders. The present invention thus provides compounds of formula (I) that are effective in inhibiting PDE1 for use as a medicament in the treatment of a mammal, preferably a human.

The invention provides a compound of formula (I) or a pharmaceutically acceptable salt thereof, as well as a pharmaceutical composition containing such a compound, for use in the treatment of a brain disease which could be a neurodegenerative disorder or a psychiatric disorder. In a preferred embodiment, the neurodegenerative disorder is selected from the group consisting of Alzheimer's Disease, Parkinson's Disease and Huntington's Disease. In another preferred embodiment, the psychiatric disorder is selected from the group consisting of Attention Deficit Hyperactivity Disorder (ADHD), depression, anxiety, narcolepsy, cognitive impairment and cognitive impairment associated with schizophrenia (CIAS). Other brain disorders could be e.g. restless leg syndrome.

This invention further provides a method of treating a brain disease which could be a neurodegenerative or a psychiatric disorder, which method comprises administering to said mammal a pharmaceutically effective amount of a compound of formula (I) or a pharmaceutically acceptable salt thereof. Examples of neurodegenerative disorders that can be treated according to the present invention include Alzheimer's Disease, Parkinson's Disease and Huntington's Disease, which method comprises administering to the subject a therapeutically effective amount of a compound of formula (I). Examples of psychiatric disorders that can be treated according to the present invention include Attention Deficit Hyperactivity Disorder (ADHD), depression, narcolepsy, cognitive impairment and cognitive impairment associated with schizophrenia (CIAS). Other brain disorders to be treated could be e.g. restless leg syndrome.

Embodiments of the Invention

In the following, embodiments of the invention are disclosed. The first embodiment is denoted E1, the second embodiment is denoted E2 and so forth E1. A compound according to formula (I)

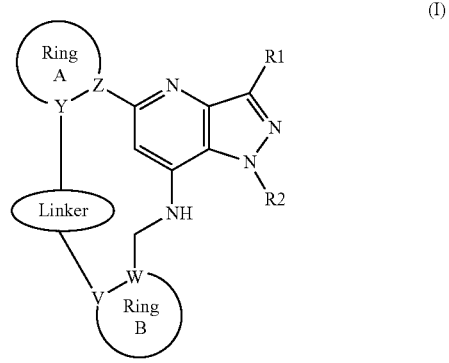

(I)

wherein ring A is a 5 or 6 membered heteroaromatic ring or ring A is phenyl, and there is 1 bond between Y and Z;

ring B is a 5 or 6 membered heteroaromatic ring or ring B is phenyl, and there is 1 bond between V and W;

when ring A is a 5 membered heteroaromatic ring, then one of Y and Z is C and the other is N, or Y=Z=C;

when ring A is a 6 membered heteroaromatic ring or phenyl, then Y=Z=C;

when ring B is a 5 membered heteroaromatic ring, then one of V and W is C and the other is N, or V=W=C;

when ring B is a 6 membered heteroaromatic ring or phenyl, then V=W=C;

the linker is a 5-7 membered saturated chain wherein the atoms consisting of carbon and optionally one or more oxygen, with the proviso that the chain contains no O—O bond, and with the proviso that the bond to V cannot be an O—N bond, and with the proviso that the bond to Y cannot be an O—N bond;

R1 is selected from the group consisting of hydrogen, linear or branched $C_{1-4}$ alkyl and saturated monocyclic $C_{3-4}$ cycloalkyl, wherein said linear or branched $C_{1-4}$ alkyl and saturated monocyclic $C_{3-4}$ cycloalkyl can be optionally substituted with one or more halogen;

R2 is selected from the group consisting of linear or branched $C_{1-6}$ alkyl, saturated monocyclic $C_{3-6}$ cycloalkyl, oxetanyl, tetrahydrofuranyl and tetrahydropyranyl, all of which can optionally be substituted with one or more halogen;

or a pharmaceutically acceptable salt thereof.

E2. The compound according to embodiment 1, wherein ring A is a 5 membered heteroaromatic ring.
E3. The compound according to embodiment 1, wherein ring A is a 6 membered heteroaromatic ring.
E4. The compound according to embodiment 1, wherein ring A is phenyl.
E5. The compound according to embodiment 1, wherein ring B is a 5 membered heteroaromatic ring.
E6. The compound according to embodiment 1, wherein ring B is a 6 membered heteroaromatic ring.
E7. The compound according to embodiment 1, wherein ring B is phenyl.
E8. The compound according to any of embodiments 1, 2 and 5, wherein said 5 membered heteroaromatic ring is pyrazolyl.
E9. The compound according to any of embodiments 1, 3 and 6, wherein said 6 membered heteroaromatic ring is pyridinyl or pyrazinyl.
E10. The compound according to any of embodiments 1-9, wherein R1 is a linear or branched $C_{1-4}$ alkyl.
E11. The compound according to any of embodiments 1-10, wherein R1 is methyl.
E12. The compound according to anyone of embodiments 1-11, wherein R2 is a linear or branched $C_{1-6}$ alkyl.
E13. The compound according to anyone of embodiments 1-12, wherein R2 is selected from methyl, ethyl and isopropyl.
E14. The compound according to embodiment 1, wherein said compound is selected from the list consisting of
1. $2^1$-isopropyl-$2^3$-methyl-$2^1$H-6,11-dioxa-3-aza-2(5,7)-pyrazolo[4,3-b]pyridina-1,5(3,2)-dipyridinacycloundecaphane;
2. $2^1$-isopropyl-$2^3$-methyl-$2^1$H-6,12-dioxa-3-aza-2(5,7)-pyrazolo[4,3-b]pyridina-1,5(3,2)-dipyridinacyclododecaphane;
3. $2^1$-isopropyl-$2^3$-methyl-$2^1$H-6,10-dioxa-3-aza-2(5,7)-pyrazolo[4,3-b]pyridina-1,5(3,2)-dipyridinacyclodecaphane;
4. $2^1$-isopropyl-$2^3$-methyl-$2^1$H-6,9,12-trioxa-3-aza-2(5,7)-pyrazolo[4,3-b]pyridina-1,5(3,2)-dipyridinacyclododecaphane;
5. $2^1$-isopropyl-$2^3$-methyl-$2^1$H,$5^1$H-11-oxa-3-aza-2(5,7)-pyrazolo[4,3-b]pyridina-1(3,2)-pyridina-5(5,1)-pyrazolacycloundecaphane;
6. $2^1$-isopropyl-$2^3$-methyl-$2^1$H-6,11-dioxa-3-aza-2(5,7)-pyrazolo[4,3-b]pyridina-1(3,2),5(2,3)-dipyridinacycloundecaphane;
7. $2^1$,$2^3$-dimethyl-$2^1$H-6,11-dioxa-3-aza-2(5,7)-pyrazolo[4,3-b]pyridina-1,5(3,2)-dipyridinacycloundecaphane;
8. $2^1$-ethyl-$2^3$-methyl-$2^1$H-6,11-dioxa-3-aza-2(5,7)-pyrazolo[4,3-b]pyridina-1,5(3,2)-dipyridinacycloundecaphane;
9. $2^1$-isopropyl-$2^3$-methyl-$2^1$H,$5^1$H-10-oxa-3-aza-2(5,7)-pyrazolo[4,3-b]pyridina-1(3,2)-pyridina-5(5,1)-pyrazolacyclodecaphane;
10. $2^1$-isopropyl-$2^3$-methyl-$2^1$H-6,11-dioxa-3-aza-2(5,7)-pyrazolo[4,3-b]pyridina-5(2,3)-pyrazina-1(3,2)-pyridinacycloundecaphane;
or a pharmaceutically acceptable salt of any of these compounds.
E15. A compound of any one of embodiments 1-14 or a pharmaceutically acceptable salt thereof, for use in therapy.
E16. A compound according to any of embodiments 1-14 or a pharmaceutically acceptable salt thereof, for use as a medicament.
E17. A pharmaceutical composition comprising a therapeutically effective amount of a compound of any one of embodiments 1-14 or a pharmaceutically acceptable salt thereof, and one or more pharmaceutically acceptable carriers, diluents and/or excipients.

E18. The pharmaceutical composition according to embodiment 17 for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.
E19. The pharmaceutical composition according to embodiment 18, wherein said pharmaceutical composition further comprises a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.
E20. The pharmaceutical composition according to embodiment 19, wherein said composition is for use in the treatment of a neurodegenerative disorder selected from the group consisting of Alzheimer's Disease, Parkinson's Disease and Huntington's Disease.
E21. The pharmaceutical composition according to embodiment 17, further comprising a second compound, which compound is useful in the treatment of a psychiatric disorder.
E22. The pharmaceutical composition according to embodiment 21, wherein said second compound has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.
E23. The pharmaceutical composition according to embodiment 22, wherein said second compound is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.
E24. The pharmaceutical composition according to any of embodiments 21-23, wherein said composition is for use in the treatment of a psychiatric disorder such as Attention Deficit Hyperactivity Disorder (ADHD), depression, anxiety, narcolepsy, cognitive impairment and cognitive impairment associated with schizophrenia (CIAS).
E25. A compound according to any of embodiments 1-14 or a pharmaceutically acceptable salt thereof, for use in the treatment of a neurodegenerative disorder, selected from the group consisting of Alzheimer's Disease, Parkinson's Disease and Huntington's Disease or for use in the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.
E26. The compound according to any of embodiments 1-14 or a pharmaceutically acceptable salt thereof, for the use in the treatment of a neurodegenerative disorder selected from the group consisting of Alzheimer's Disease, Parkinson's Disease and Huntington's Disease, wherein said compound is used in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E27. The compound according to any of embodiments 1-14 or a pharmaceutically acceptable salt thereof, for the use in the treatment of a psychiatric disorder such as Attention Deficit Hyperactivity Disorder (ADHD), depression, anxiety, narcolepsy, cognitive impairment and cognitive impairment associated with schizophrenia (CIAS), wherein said compound is used in combination with a second compound, which compound is useful in the treatment of a psychiatric disorder.

E28. The compound or pharmaceutically acceptable salt thereof for the use according to embodiment 27, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E29. The compound or pharmaceutically acceptable salt thereof for the use according to embodiment 27, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

E30. A method for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome, which method comprises the administration of a therapeutically effective amount of a compound according to any of embodiments 1-14 or a pharmaceutically acceptable salt thereof, to a patient in need thereof.

E31. A method for the treatment of a neurodegenerative disorder, selected from the group consisting of Alzheimer's Disease, Parkinson's Disease and Huntington's Disease, which method comprises the administration of a therapeutically effective amount of a compound according to any of embodiments 1-14 or a pharmaceutically acceptable salt thereof, in combination with a therapeutically effective amount of a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody; to a patient in need thereof.

E32. A method for the treatment of a psychiatric disorder such as Attention Deficit Hyperactivity Disorder (ADHD), depression, anxiety, narcolepsy, cognitive impairment and cognitive impairment associated with schizophrenia (CIAS), which method comprises the administration of a therapeutically effective amount of a compound according to any of embodiments 1-14 or a pharmaceutically acceptable salt thereof, in combination with a therapeutically effective amount of a second compound, which compound is useful in the treatment of a psychiatric disorder; to a patient in need thereof.

E33. The method according to embodiment 32, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E34. The method according to embodiment 32, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

E35. Use of a compound according to any of embodiments 1-14 or a pharmaceutically acceptable salt thereof, in the manufacture of a medicament for the treatment of a neurodegenerative disorder, selected from the group consisting of Alzheimer's Disease, Parkinson's Disease and Huntington's Disease or for the treatment of a psychiatric disorder such as Attention Deficit Hyperactivity Disorder (ADHD), depression, anxiety, narcolepsy, cognitive impairment and cognitive impairment associated with schizophrenia (CIAS), or another brain disease like restless leg syndrome.

E36. Use of a compound according to any of embodiments 1-14 or a pharmaceutically acceptable salt thereof, in the manufacture of a medicament for the treatment of a neurodegenerative disorder, selected from the group consisting of Alzheimer's Disease, Parkinson's Disease and Huntington's Disease, wherein said medicament is for use in combination with a second compound, which compound is selected from a compound useful in active or passive Tau immunotherapy, a compound useful in active or passive Aβ peptide immunotherapy, an NMDA receptor antagonist, an acetylcholine esterase inhibitor, a BACE inhibitor, a 5-HT6 receptor antagonist, an antiepileptic, an anti-inflammatory drug or an anti-N3-pGlu Abeta monoclonal antibody.

E37. Use of a compound according to any of embodiments 1-14 or a pharmaceutically acceptable salt thereof, in the manufacture of a medicament for the treatment of a psychiatric disorder such as Attention Deficit Hyperactivity Disorder (ADHD), depression, anxiety, narcolepsy, cognitive impairment and cognitive impairment associated with schizophrenia (CIAS), wherein said medicament is for use in combination with a second compound, which compound is useful in the treatment of a psychiatric disorder.

E38. The use according to embodiment 37, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

E39. The use according to embodiment 37, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

All references, including publications, patent applications and patents, cited herein are hereby incorporated by reference in their entirety and to the same extent as if each reference were individually and specifically indicated to be incorporated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The present invention includes all modifications and equivalents of the subject-matter recited in the claims appended hereto, as permitted by applicable law.

Compounds of the Invention

TABLE 1

Compounds of the invention

| Example | Compound | PDE1A, $IC_{50}$ (nM) | PDE1B, $IC_{50}$ (nM) | PDE1C, $IC_{50}$ (nM) |
|---|---|---|---|---|
| 1 | $2^1$-isopropyl-$2^3$-methyl-$2^1$H-6,11-dioxa-3-aza-2(5,7)-pyrazolo[4,3-b]pyridina-1,5(3,2)-dipyridinacycloundecaphane | 12 | 1.4 | 20 |
| 2 | $2^1$-isopropyl-$2^3$-methyl-$2^1$H-6,12-dioxa-3-aza-2(5,7)-pyrazolo[4,3-b]pyridina-1,5(3,2)-dipyridinacyclododecaphane | 18 | 1.5 | 54 |
| 3 | $2^1$-isopropyl-$2^3$-methyl-$2^1$H-6,10-dioxa-3-aza-2(5,7)-pyrazolo[4,3-b]pyridina-1,5(3,2)-dipyridinacyclodecaphane | 38 | 4.2 | 69 |
| 4 | $2^1$-isopropyl-$2^3$-methyl-$2^1$H-6,9,12-trioxa-3-aza-2(5,7)-pyrazolo[4,3-b]pyridina-1,5(3,2)-dipyridinacyclododecaphane | 2.6 | 0.54 | 16 |
| 5 | $2^1$-isopropyl-$2^3$-methyl-$2^1$H,$5^1$H-11-oxa-3-aza-2(5,7)-pyrazolo[4,3-b]pyridina-1(3,2)-pyridina-5(5,1)-pyrazolacycloundecaphane | 25 | 4.7 | 80 |
| 6 | $2^1$-isopropyl-$2^3$-methyl-$2^1$H-6,11-dioxa-3-aza-2(5,7)-pyrazolo[4,3-b]pyridina-1(3,2),5(2,3)-dipyridinacycloundecaphane | 0.47 | 0.27 | 3.9 |
| 7 | $2^1$,$2^3$-dimethyl-$2^1$H-6,11-dioxa-3-aza-2(5,7)-pyrazolo[4,3-b]pyridina-1,5(3,2)-dipyridinacycloundecaphane | 428 | 95 | 497 |
| 8 | $2^1$-ethyl-$2^3$-methyl-$2^1$H-6,11-dioxa-3-aza-2(5,7)-pyrazolo[4,3-b]pyridina-1,5(3,2)-dipyridinacycloundecaphane | 256 | 36 | 412 |
| 9 | $2^1$-isopropyl-$2^3$-methyl-$2^1$H,$5^1$H-10-oxa-3-aza-2(5,7)-pyrazolo[4,3-b]pyridina-1(3,2)-pyridina-5(5,1)-pyrazolacyclodecaphane | 53 | 15 | 56 |
| 10 | $2^1$-isopropyl-$2^3$-methyl-$2^1$H-6,11-dioxa-3-aza-2(5,7)-pyrazolo[4,3-b]pyridina-5(2,3)-pyrazina-1(3,2)-pyridinacycloundecaphane; | 10 | >99% inhibition at 10 µM | 17 |

Table 1 lists the $IC_{50}$ value for inhibition of PDE1 by the compounds of the invention. The $IC_{50}$ value refers to the concentration (nM) of the compound required to reach 50% inhibition of the PDE1 enzyme at the specified substrate concentration. PDE1 assays are described in the Experimental Section.

Supporting Examples

The compounds in Table 2 are disclosed herein in order to support the substituents of R1 and R2 and the rings A and B.

TABLE 2

Supporting Examples

| Supporting example | Compound | PDE1A, $IC_{50}$ (nM) | PDE1B, $IC_{50}$ (nM) | PDE1C, $IC_{50}$ (nM) |
|---|---|---|---|---|
| S1 | 5-(2-ethoxy-3-pyridyl)-1-isopropyl-3-methyl-N-[(5-methyl-1,3,4-oxadiazol-2-yl)methyl]pyrazolo[4,3-b]pyridin-7-amine | 18 | 1.6 | 40 |

TABLE 2-continued

Supporting Examples

| Supporting example | Compound | PDE1A, IC$_{50}$ (nM) | PDE1B, IC$_{50}$ (nM) | PDE1C, IC$_{50}$ (nM) |
|---|---|---|---|---|
| S12 | 1-cyclopropyl-5-(2-ethoxy-3-pyridyl)-3-methyl-N-[(1-methylpyrazol-4-yl)methyl]pyrazolo[4,3-b]pyridin-7-amine | 200 | 60 | 690 |
| S13 | 5-(2-ethoxy-3-pyridyl)-N-[(1-methylpyrazol-4-yl)methyl]-1-propyl-pyrazolo[4,3-b]pyridin-7-amine | 90 | 15 | 340 |
| S14 | 5-(2-ethoxypyridin-3-yl)-N-((1-methyl-1H-pyrazol-4-yl)methyl)-1-(oxetan-3-yl)-1H-pyrazolo[4,3-b]pyridin-7-amine | 450 | 38 | 300 |
| S17 | 5-(2-ethoxy-3-pyridyl)-1-isopropyl-N-[(1-methylimidazol-2-yl)methyl]pyrazolo[4,3-b]pyridin-7-amine | 700 | 54 | 970 |
| S23 | 5-(2-ethoxy-3-pyridyl)-1-isopropyl-N-(m-tolylmethyl)pyrazolo[4,3-b]pyridin-7-amine | 240 | 38 | 750 |
| S26 | 5-(2-ethoxy-3-pyridyl)-1-ethyl-N-[(1-methylpyrazol-4-yl)methyl]pyrazolo[4,3-b]pyridin-7-amine | 140 | 22 | 440 |
| S28 | 5-(2-ethoxy-3-pyridyl)-1,3-dimethyl-N-[(1-methylpyrazol-4-yl)methyl]pyrazolo[4,3-b]pyridin-7-amine | 550 | 85 | 1900 |
| S29 | 5-(2-ethoxy-3-pyridyl)-1-isopropyl-3-methyl-N-[(4-methylthiazol-2-yl)methyl]pyrazolo[4,3-b]pyridin-7-amine | 27 | 1.1 | 44 |
| S41 | N-benzyl-5-(2-ethoxy-3-pyridyl)-1-isopropyl-pyrazolo[4,3-b]pyridin-7-amine | 500 | 45 | 500 |
| S48 | 5-(2-ethoxypyridin-3-yl)-1-ethyl-3-methyl-N-((1-methyl-1H-pyrazol-4-yl)methyl)-1H-pyrazolo[4,3-b]pyridin-7-amine | 38 | 6.3 | 170 |
| S61 | 5-(1,3-dimethylpyrazol-4-yl)-1-isopropyl-3-methyl-N-[(1-methylpyrazol-4-yl)methyl]pyrazolo[4,3-b]pyridin-7-amine | 550 | 120 | 680 |
| S67 | 5-(2-ethoxy-3-pyridyl)-3-methyl-1-[1-methylpropyl]-N-[(1-methylpyrazol-3-yl)methyl]pyrazolo[4,3-b]pyridin-7-amine, enantiomer 2 | 9.6 | 0.64 | 27 |
| S69 | 5-(2-ethoxy-3-pyridyl)-1-[1-methylpropyl]-N-[(1-methylpyrazol-4-yl)methyl]pyrazolo[4,3-b]pyridin-7-amine, enantiomer 1 | 14 | 1.2 | 40 |
| S113 | 5-(2-ethoxy-3-pyridyl)-3-methyl-N-[(2-methylthiazol-4-yl)methyl]-1-(oxetan-3-yl)pyrazolo[4,3-b]pyridin-7-amine | 110 | 5.7 | 130 |
| S120 | 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 2 | 4.6 | 0.27 | 7.6 |
| S147 | 1-isopropyl-3-methyl-N-[(1-methylpyrazol-4-yl)methyl]-5-thiazol-2-yl-pyrazolo[4,3-b]pyridin-7-amine | 12 | 2.1 | 28 |
| S161 | 5-(2-ethoxy-3-pyridyl)-1-isopropyl-3-methyl-N-[(2-methyl-1,2,4-triazol-3-yl)methyl]pyrazolo[4,3-b]pyridin-7-amine | 60 | 6.6 | 120 |
| S162 | 5-(2-ethoxy-3-pyridyl)-1-isopropyl-3-methyl-N-[(4-methyl-1,2,4-triazol-3-yl)methyl]pyrazolo[4,3-b]pyridin-7-amine | 100 | 13 | 180 |
| S163 | 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine | 120 | 14 | 120 |
| S165 | N-[[1-(difluoromethyl)pyrazol-4-yl]methyl]-5-(2-ethoxy-3-pyridyl)-1-isopropyl-3-methyl-pyrazolo[4,3-b]pyridin-7-amine | 73 | 5.9 | 110 |
| S168 | 1-isopropyl-3-methyl-N-[(1-methylpyrazol-4-yl)methyl]-5-oxazol-2-yl-pyrazolo[4,3-b]pyridin-7-amine | 14 | 2.6 | 36 |
| S169 | 1-isopropyl-3-methyl-N-[(1-methylpyrazol-4-yl)methyl]-5-(3-methyltriazol-4-yl)pyrazolo[4,3-b]pyridin-7-amine | 610 | 85 | 170 |
| S184 | 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine | 13 | 2.4 | 45 |
| S195 | 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine | 420 | 110 | 160 |

TABLE 2-continued

Supporting Examples

| Supporting example | Compound | PDE1A, IC$_{50}$ (nM) | PDE1B, IC$_{50}$ (nM) | PDE1C, IC$_{50}$ (nM) |
|---|---|---|---|---|
| S197 | 5-(2-ethoxy-3-pyridyl)-N-[(2-methoxy-3-pyridyl)methyl]-3-methyl-1-(oxetan-3-yl)pyrazolo[4,3-b]pyridin-7-amine | 190 | 13 | 190 |
| S199 | 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine | 7.4 | 0.75 | 26 |
| S200 | 1-isopropyl-3-methyl-N-((1-methyl-1H-pyrazol-4-yl)methyl)-5-(4-methyloxazol-5-yl)-1H-pyrazolo[4,3-b]pyridin-7-amine | 98 | 18 | 110 |

Table 2 lists the IC$_{50}$ value for inhibition of PDE1 by the supporting examples. The IC$_{50}$ value refers to the concentration (nM) of the compound required to reach 50% inhibition of the PDE1 enzyme at the specified substrate concentration. PDE1 assays are described in the Experimental Section.

EXPERIMENTAL SECTION

Preparation of the Compounds of the Invention—General Methods

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as "Compendium of Organic Synthetic Methods, Vol. I-XIII" (published with Wiley-Interscience, ISSN: 1934-4783). Preferred methods include, but are not limited to, those described below.

The schemes are representative of methods useful in synthesizing the compounds of the present invention and the supporting examples. They are not to constrain the scope of the invention in any way.

Method 1:

Scheme 1 where R1 is as described for formula I and R is hydrogen or R is R2 as described for formula I. Compounds of general formula IV (Scheme 1) can be prepared from compounds of general formula II and III.

Method 2:

Scheme 2 where R1 is as described for formula I and R is R2 as described for formula I or a protection group such as para-methoxy benzyl.

Compounds of general formula IV (Scheme 2) can be prepared from compounds of general formula II, III and V as described in the literature (e.g. Int. Pat. App. WO2013142307)

Method 3:

Scheme 3

R = H
R = Protection group

-continued

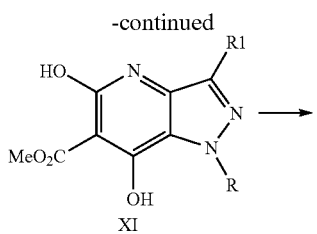
XI

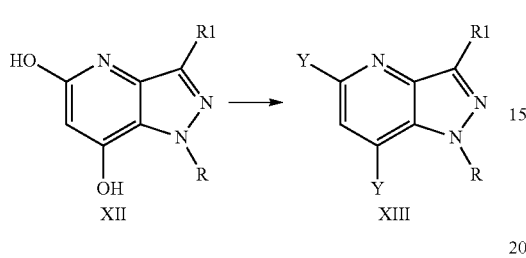
XII → XIII where R1 is as described for formula I, R is R2 as described for formula I or R is a protection group such as para-methoxy benzyl and Y is a halogen such as chlorine or bromine.

Compounds of general formula VIII (Scheme 3) can be prepared by nitration of compounds of general formula IV followed by reduction. Compounds of general formula XI can be prepared by reaction of compounds of general formula VIII with methyl 3-chloro-3-oxopropanoate followed by ring-closure in the presence of a base such as sodium ethoxide or sodium methoxide. Hydrolysis and decarboxylation of compounds of general formula XI followed by treatment with phosphoryl trichloride or phosphoryl tribromide gives compounds of general formula XIII.

Method 4:

Scheme 4

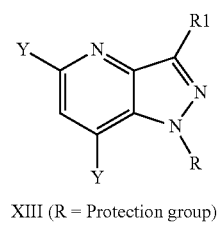
XIII (R = Protection group)

↓

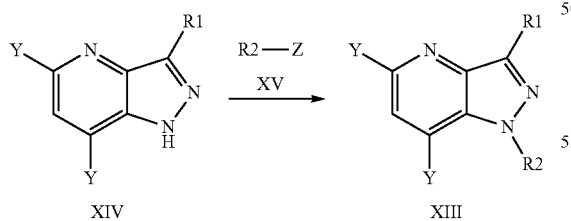
XIV → XIII where R1 and R2 are as described for formula I, R is a protection group such as para-methoxy benzyl, Y is a halogen such as chlorine or bromine and Z is a leaving group such as chlorine, bromine, iodine or a methanesulfonate group or Z is a hydroxy group.

Compounds of general formula XIV (Scheme 4) can be prepared by the deprotection of compounds of general formula XIII where R is a protection group. If the protection group is para-methoxy benzyl, the deprotection can be performed by treatment with an acid such as trifluoroacetic acid. Compounds of general formula XIII can be prepared by reaction of compounds of general formula XIV with compounds of general formula XV in the presence of a base such as cesium carbonate or using Mitsunobu reaction conditions when Z is a hydroxy group.

Method 5:

Scheme 5

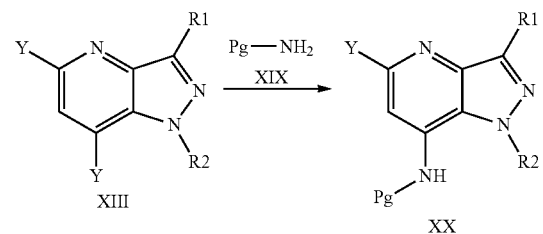
XIII → XX where R1, R2, R3 and R4 are as described for formula I, R are hydroxy groups or R together with the boron atom form a 4,4,5,5-tetramethyl-1,3,2-dioxaborolane group and Pg is a protection group such as para-methoxy benzyl. Y is a halogen such as chlorine or bromine.

Compounds of general formula XX (Scheme 6) can be prepared by treatment of compounds of general formula XIII with compounds of general formula XIX in the presence of a base such as but not limited to cesium fluoride or N,N-diisopropylethylamine.

Method 6:

Scheme 6:

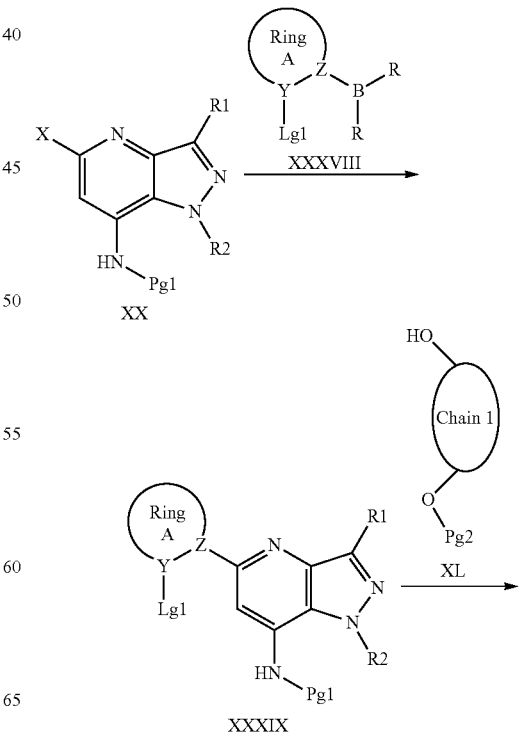
XX → XXXIX

-continued

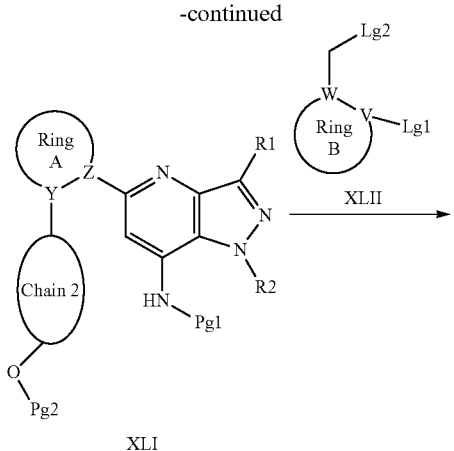

XLI

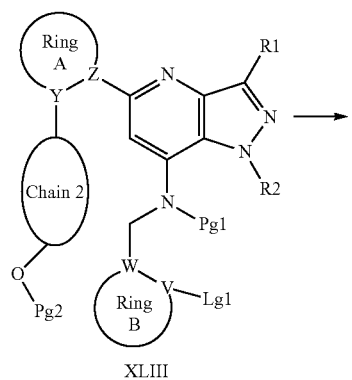

XLIII

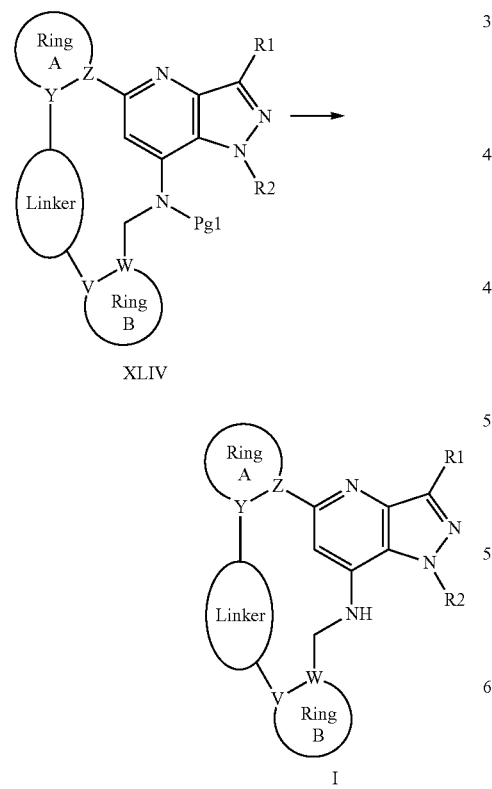

XLIV

I where R1, R2, V, W, Y, Z, Ring A, Ring B and Linker are as described formula I, R are hydroxy groups or R together with the boron atom form a 4,4,5,5-tetramethyl-1,3,2-dioxaborolane group, X is a halogen such as chlorine or bromine, Lg1 and Lg2 are leaving groups such as halogen (F, Cl, Br or I), $CF_3SO_3$—, $C_4F_9SO_3$—, $CH_3SO_3$ or p-toluenesulfonate, Pg1 and Pg2 are protecting groups such as p-methoxybenzyl, allyl, tert-butyldimethylsilyl or tert-butyldiphenylsilyl. Chain 1 and Chain 2 consists of atoms, that together with the terminal oxygen atoms will form Linker as described for formula I.

Compounds of general formula XXXIX (Scheme 7) can be prepared from compounds of general formulae XX and XXXVIII in the presence of a palladium catalyst such as [1,1'-bis(diphenylphosphino)ferrocene]palladium(II) dichloride and a base such as potassium carbonate or other Suzuki-Miyaura coupling reaction conditions known to chemists skilled in the art of organic synthesis. Compounds of general formula XLI can be prepared by treatment of compounds of general formula XL with a base such as sodium hydride followed by reaction with compounds of general formula XXXIX. Alkylation of compounds of general formula XLI with compounds of general formula XLII in the presence of a base such as sodium hydride gives compounds of general formula XLIII. Removal of the protection group (Pg2) and treatment with a base such as sodium hydride gives compounds of general formula XLIV. Removal of the protection group (Pg1) on compounds of general formula XLIV gives compounds of general formula I.

Method 7:

Scheme 7:

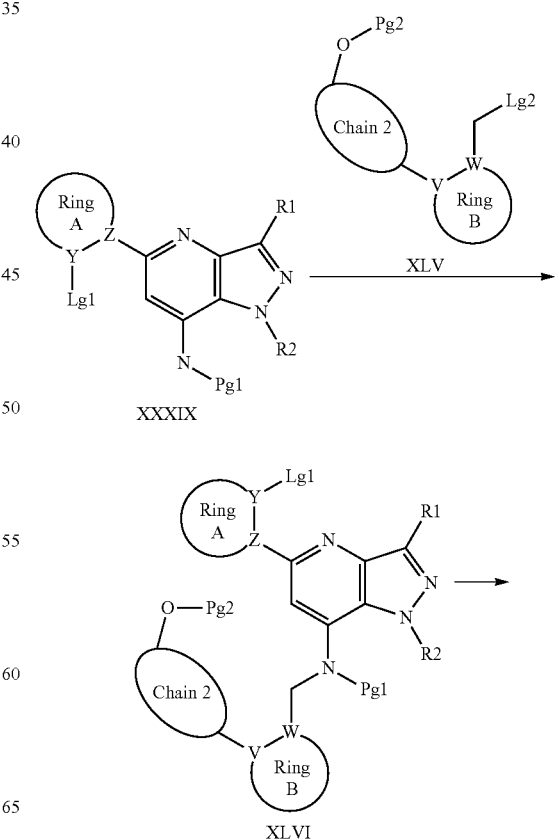

XXXIX

XLVI

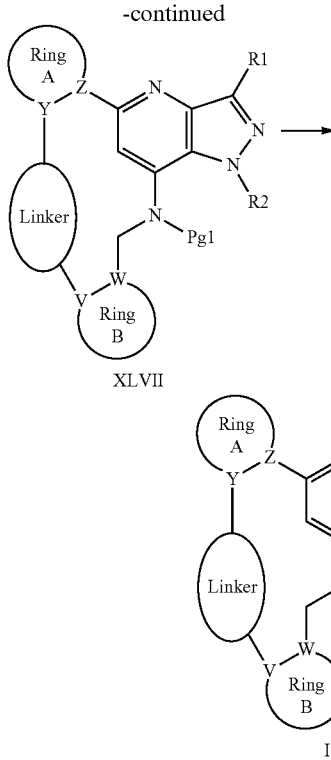

XLVII

I where R1, R2, V, W, Y, Z, Ring A, Ring B and Linker are as described formula I, R are hydroxy groups or R together with the boron atom form a 4,4,5,5-tetramethyl-1,3,2-dioxaborolane group, X is a halogen such as chlorine or bromine, Lg1 and Lg2 are leaving groups such as halogen (F, Cl, Br or I), $CF_3SO_3—$, $C_4F_9SO_3—$, $CH_3SO_3$ or p-toluenesulfonate, Pg1 and Pg2 are protecting groups such as p-methoxybenzyl, allyl, tert-butyldimethylsilyl or tert-butyldiphenylsilyl. Chain 2 consists of atoms, that together with the terminal oxygen atoms will form Linker as described for formula I.

Compounds of general formula XLVI (Scheme 15) can be prepared by alkylation of compounds of general formula XXXIX with compounds of general formula XLV in the presence of a base such as sodium hydride. Removal of the protection group (Pg2) and treatment with a base such as sodium hydride gives compounds of general formula XLVII. Removal of the protection group (Pg1) on compounds of general formula XLVII gives compounds of general formula I.

LC-MS Methods

Method A: An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method B: An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Method C: An Agilent 1200 LCMS system with ELS detector was used. Phenomenex Luna-C18, 5 μm; 2.0×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method D: A Waters Acquity UPLC-MS was used. Column: Acquity UPLC BEH C18 1.7 μm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method E: A Waters Acquity UPLC-MS was used. Column: Acquity UPLC BEH C18 1.7 μm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/min.

Method F: An Agilent 1200 LCMS system with ELS detector was used. Column: Waters XBridge ShieldRP18, 2.1×50 mm, 5 μm; Column temperature: 40° C.; Solvent system: A=water/ammonia (99.95:0.05) and B=acetonitrile; Method: Linear gradient elution with A:B=85:15 to 0:100 in 3.4 minutes and with a flow rate of 0.8 mL/min.

Method G: An Agilent 1200 LCMS system with ELS detector was used. Column: Agilent TC-C18 5 μm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=99:1 to 0:100 in 4.0 minutes and with a flow rate of 0.8 mL/min.

Method L: An Agilent 1200 LCMS system with ELS detector was used. Waters Xbridge-C18, 50×2 mm; Column temperature: 50° C.; Solvent system: A=water/trifluoroacetic acid (99.96:0.04) and B=acetonitrile/trifluoroacetic acid (99.98:0.02); Method: Linear gradient elution with A:B=90:10 to 0:100 in 3.4 minutes and with a flow rate of 0.8 mL/min.

Method M: An Agilent 1200 LCMS system with ELS detector was used. Waters Xbridge-C18, 50×2 mm; Column temperature: 50° C.; Solvent system: A=water/trifluoroacetic acid (99.96:0.04) and B=acetonitrile/trifluoroacetic acid (99.98:0.02); Method: Linear gradient elution with A:B=99:1 to 0:100 in 3.4 minutes and with a flow rate of 0.8 mL/min.

INTERMEDIATES (FOR COMPOUNDS OF THE INVENTION AND SUPPORTING EXAMPLES)

Preparation of ethyl 3-methyl-1H-pyrazole-5-carboxylate

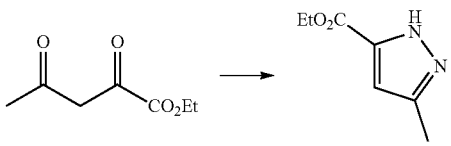

A solution of ethyl 2,4-dioxopentanoate (20 g, 126 mmol, 18 mL) and hydrazine hydrate (6.96 g, 139 mmol, 6.76 mL) in ethanol (400 mL) was stirred at 0° C. for 1 hour. The mixture was concentrated to give ethyl 3-methyl-1H-pyrazole-5-carboxylate (19 g, 123 mmol, 97% yield).

Preparation of ethyl 1,3-dimethyl-1H-pyrazole-5-carboxylate

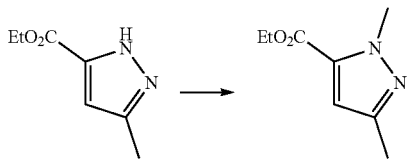

To a solution of ethyl 3-methyl-1H-pyrazole-5-carboxylate (19.5 g, 126 mmol) in DMF (200 mL) was added Me$_2$SO$_4$ (23.8 g, 189 mmol, 17.9 mL). The mixture was stirred at 80° C. for 18 hours. After cooling to 0° C., the mixture was diluted with ice, then aqueous ammonia (25%) was added to adjust the pH to 8. Then the mixture was extracted with ethyl acetate (300 mL×3), the combined organic layers were washed with brine (50 mL), dried, and concentrated. The crude mixture was purified by flash chromatography with petroleum ether: ethyl acetate=5:1 to give ethyl 1,3-dimethyl-1H-pyrazole-5-carboxylate (15 g, 89 mmol, 71% yield).

Preparation of ethyl 2-(methoxyimino)-4-oxopentanoate

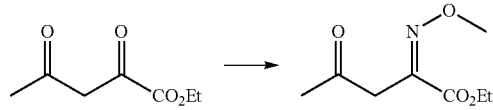

A mixture of ethyl 2,4-dioxopentanoate (27 g, 171 mmol, 24 mL) and methoxylamine (15 g, 179 mmol, 13.6 mL) in ethanol (150 mL) was stirred at 25° C. for 18 hours under a nitrogen atmosphere. The mixture was concentrated. The crude mixture was purified by flash silica gel chromatography with petroleum ether:ethyl acetate=10:1 to give ethyl 2-(methoxyimino)-4-oxopentanoate (19.9 g, 103 mmol, 60% yield). $^1$H NMR (chloroform-d 400 MHz): δ 4.34 (q, J=6.8 Hz, 2H), 4.07 (s, 3H), 3.71 (s, 2H), 2.21 (s, 3H), 1.35 (d, J=7.6 Hz, 3H).

Preparation of ethyl 1-isopropyl-3-methyl-1H-pyrazole-5-carboxylate

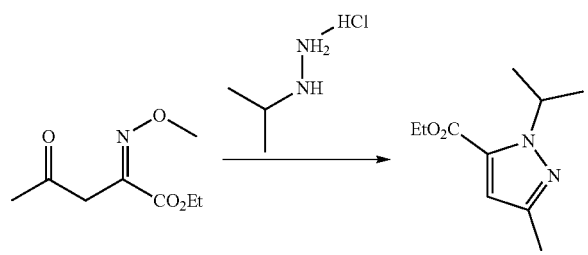

To a solution of ethyl 2-(methoxyimino)-4-oxopentanoate (14.6 g, 78.0 mmol) in ethanol (200 mL) was added isopropylhydrazine hydrochloride (17.25 g, 156 mmol). The mixture was stirred at 80° C. for 18 hours. The mixture was concentrated. Saturated aqueous NaHCO$_3$ was added into the residue to adjust the pH to 7. Then the mixture was extracted with dichloromethane (100 mL×3), the combined organic layers were washed with brine, dried over Na$_2$SO$_4$ and concentrated. The crude mixture was purified by flash silica gel chromatography with petroleum ether:ethyl acetate=10:1 to give ethyl 1-isopropyl-3-methyl-1H-pyrazole-5-carboxylate (12.3 g, 62.7 mmol, 80% yield). $^1$H NMR (chloroform-d 400 MHz): δ 6.59 (s, 1H), 5.41-5.44 (m, 1H), 4.35-4.29 (m, 2H), 2.29 (s, 3H), 1.48 (d, J=6.8 Hz, 6H), 1.39-1.35 (m, 3H).

Preparation of ethyl 1-isopropyl-3-methyl-4-nitro-1H-pyrazole-5-carboxylate

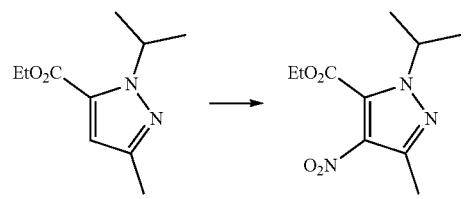 [SMILES: CCOC(=O)c1cc(C)nn1C(C)C ; CCOC(=O)c1c([N+](=O)[O-])c(C)nn1C(C)C]

To a solution of ethyl 1-isopropyl-3-methyl-1H-pyrazole-5-carboxylate (8 g, 40.8 mmol) and (2,2,2-trifluoroacetyl) 2,2,2-trifluoroacetate (59.9 g, 285.4 mmol, 39.7 mL) in TFA (80 mL) was added ammonium nitrate (6.5 g, 81.5 mmol, 3.8 mL) slowly at 0° C. The mixture was stirred at 20° C. for 18 hours. The solution was cooled to 0° C. and then neutralized with aqueous K$_2$CO$_3$ and the product was extracted with ethyl acetate:dichloromethane=40:1 (205 mL×4). The combined organic layers were washed with brine (150 mL), dried over Na$_2$SO$_4$ and concentrated to give ethyl 1-isopropyl-3-methyl-4-nitro-1H-pyrazole-5-carboxylate (9.8 g).

Ethyl 1-ethyl-3-methyl-4-nitro-1H-pyrazole-5-carboxylate was prepared in a similar way from ethylhydrazine.

Ethyl 1-cyclopropyl-3-methyl-4-nitro-1H-pyrazole-5-carboxylate was prepared in a similar way from cyclopropylhydrazine.

(±)-Ethyl 1-(sec-butyl)-3-methyl-1H-pyrazole-5-carboxylate was prepared in a similar way from (±)-sec-butylhydrazine hydrochloride.

Preparation of ethyl 3-methyl-4-nitro-1H-pyrazole-5-carboxylate

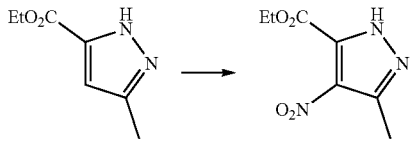

Ethyl 3-methyl-1H-pyrazole-5-carboxylate (12 g, 78 mmol) was added in portions to fuming nitric acid (140 g, 2.2 mol, 100 mL) at 0° C. The mixture was stirred at 15° C. for 16 hours. The mixture was poured into ice (200 g) and adjusted to pH 7 by saturated aqueous K$_2$CO$_3$. The mixture was extracted with ethyl acetate (500 mL×2). The organic layer was washed with H$_2$O (500 mL), brine (500 mL), dried over Na$_2$SO$_4$, filtered and concentrated to give ethyl 3-methyl-4-nitro-1H-pyrazole-5-carboxylate (13 g, 65 mmol, 84% yield). ¹H NMR (chloroform-d 400 MHz) δ 11.41 (brs, 1H), 4.47-4.42 (m, 2H), 2.64 (s, 3H), 1.39 (t, J=7.2 Hz, 3H).

Preparation of ethyl 1-(4-methoxybenzyl)-3-methyl-4-nitro-1H-pyrazole-5-carboxylate and ethyl 1-(4-methoxybenzyl)-5-methyl-4-nitro-1H-pyrazole-3-carboxylate

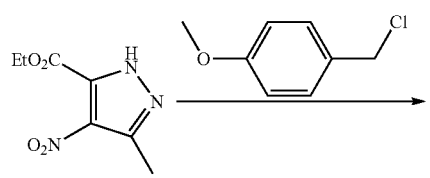

To a solution of ethyl 3-methyl-4-nitro-1H-pyrazole-5-carboxylate (4.40 g, 22.1 mmol) in dry DMF (50 mL) was added 1-(chloromethyl)-4-methoxybenzene (4.15 g, 26.5 mmol, 3.6 mL) and $K_2CO_3$ (6.11 g, 44.2 mmol). The mixture was stirred at 15° C. for 16 hours. The mixture was concentrated and water (20 mL) was added. The mixture was extracted with ethyl acetate (20 mL×2). The combined organic layers were washed with $H_2O$ (20 mL×2), brine (20 mL), dried over $Na_2SO_4$, filtered and concentrated. The residue was purified by flash chromatography on silica gel (0% to 50% ethyl acetate in petroleum ether) to give ethyl 1-(4-methoxybenzyl)-3-methyl-4-nitro-1H-pyrazole-5-carboxylate (2.80 g, 8.77 mmol, 40% yield) and ethyl 1-(4-methoxybenzyl)-5-methyl-4-nitro-1H-pyrazole-3-carboxylate (3.50 g, 11 mmol, 50% yield).

Preparation of ethyl 4-amino-1-isopropyl-3-methyl-1H-pyrazole-5-carboxylate

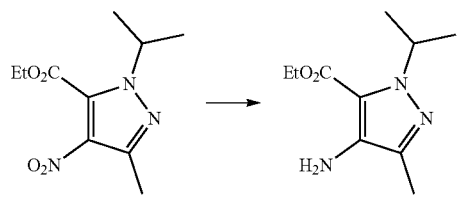 [SMILES: CCOC(=O)c1c([N+](=O)[O-])c(C)nn1C(C)C ; CCOC(=O)c1c(N)c(C)nn1C(C)C]

To a solution of ethyl 1-isopropyl-3-methyl-4-nitro-1H-pyrazole-5-carboxylate (10.23 g, 42.41 mmol) in ethyl acetate (200 mL) was added Pd—C (10%, 2.0 g, wet) under nitrogen. The suspension was degassed under vacuo and purged with hydrogen several times. The mixture was stirred under hydrogen (30 psi) at 40° C. for 18 hours. The mixture was filtered and the residue was washed with ethyl acetate (150 ml×3), the combined filtrates were concentrated to give ethyl 4-amino-1-isopropyl-3-methyl-1H-pyrazole-5-carboxylate (8.96 g).

Ethyl 4-amino-1-(4-methoxybenzyl)-3-methyl-1H-pyrazole-5-carboxylate was prepared in a similar way from ethyl 1-(4-methoxybenzyl)-3-methyl-4-nitro-1H-pyrazole-5-carboxylate.

Ethyl 4-amino-1-ethyl-3-methyl-1H-pyrazole-5-carboxylate was prepared in a similar way from ethyl 1-ethyl-3-methyl-4-nitro-1H-pyrazole-5-carboxylate.

Ethyl 4-amino-1-cyclopropyl-3-methyl-1H-pyrazole-5-carboxylate was prepared in a similar way from ethyl 1-cyclopropyl-3-methyl-4-nitro-1H-pyrazole-5-carboxylate.

Ethyl 4-amino-1,3-dimethyl-1H-pyrazole-5-carboxylate was prepared in a similar way from ethyl 1,3-dimethyl-4-nitro-1H-pyrazole-5-carboxylate.

(±)-Ethyl 4-amino-1-(sec-butyl)-3-methyl-1H-pyrazole-5-carboxylate was prepared in a similar way from (±)-ethyl 1-(sec-butyl)-3-methyl-1H-pyrazole-5-carboxylate.

Preparation of ethyl 1-isopropyl-4-(3-methoxy-3-oxopropanamido)-3-methyl-1H-pyrazole-5-carboxylate

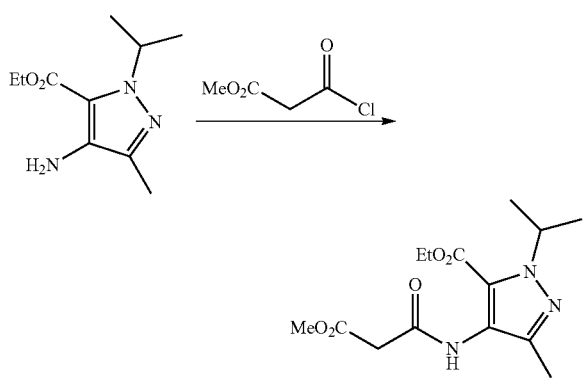

To a solution of ethyl 4-amino-1-isopropyl-3-methyl-1H-pyrazole-5-carboxylate (7.96 g, 37.7 mmol) in dichloromethane (150 mL) was added methyl 3-chloro-3-oxopropanoate (5.14 g, 37.7 mmol, 4.02 mL). The mixture was stirred at 50° C. for 45 minutes. After the reaction mixture had cooled to room temperature, the mixture was partitioned between dichloromethane (200 mL) and saturated aqueous $NaHCO_3$ (100 mL), the aqueous phase was extracted with dichloromethane (100 mL×2), the combined organic layers were washed with brine (50 mL), dried over $MgSO_4$ and concentrated to give ethyl 1-isopropyl-4-(3-methoxy-3-oxopropanamido)-3-methyl-1H-pyrazole-5-carboxylate (11.7 g, 37 mmol, >95% yield).

Ethyl 4-(3-methoxy-3-oxopropanamido)-1-(4-methoxybenzyl)-3-methyl-1H-pyrazole-5-carboxylate was prepared in a similar way from ethyl 4-amino-1-(4-methoxybenzyl)-3-methyl-1H-pyrazole-5-carboxylate.

Ethyl 1-ethyl-4-(3-methoxy-3-oxopropanamido)-3-methyl-1H-pyrazole-5-carboxylate was prepared in a similar way from ethyl 4-amino-1-ethyl-3-methyl-1H-pyrazole-5-carboxylate.

Ethyl 1-cyclopropyl-4-(3-methoxy-3-oxopropanamido)-3-methyl-1H-pyrazole-5-carboxylate was prepared in a similar way from ethyl 4-amino-1-cyclopropyl-3-methyl-1H-pyrazole-5-carboxylate.

Ethyl 4-(3-methoxy-3-oxopropanamido)-1,3-dimethyl-1H-pyrazole-5-carboxylate was prepared in a similar way from ethyl 4-amino-1,3-dimethyl-1H-pyrazole-5-carboxylate.

(±)-Ethyl 1-(sec-butyl)-4-(3-methoxy-3-oxopropanamido)-3-methyl-1H-pyrazole-5-carboxylate was prepared in a similar way from (±)-ethyl 4-amino-1-(sec-butyl)-3-methyl-1H-pyrazole-5-carboxylate.

Preparation of methyl 5,7-dihydroxy-1-isopropyl-3-methyl-1H-pyrazolo[4,3-b]pyridine-6-carboxylate

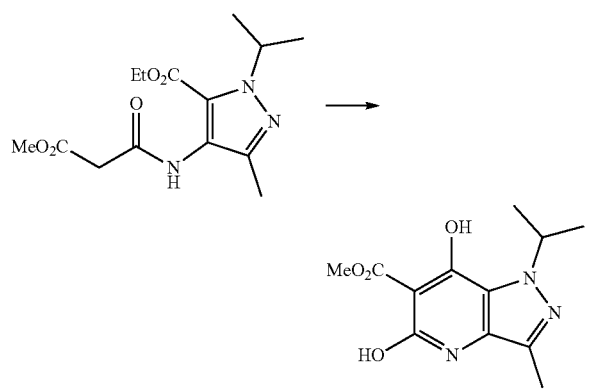

To a solution of ethyl 1-isopropyl-4-(3-methoxy-3-oxopropanamido)-3-methyl-1H-pyrazole-5-carboxylate (12.5 g, 40 mmol) in ethanol (200 mL) was added NaOEt (5.45 g, 80 mmol). The mixture was stirred at 20° C. for 1 hour. The mixture was concentrated. The crude product (10.62 g) was used into the next step without further purification.

Methyl 5,7-dihydroxy-1-(4-methoxybenzyl)-3-methyl-1H-pyrazolo[4,3-b]pyridine-6-carboxylate was prepared in a similar way from ethyl 4-(3-methoxy-3-oxopropanamido)-1-(4-methoxybenzyl)-3-methyl-1H-pyrazole-5-carboxylate.

Methyl 1-ethyl-5,7-dihydroxy-3-methyl-1H-pyrazolo[4,3-b]pyridine-6-carboxylate was prepared in a similar way from ethyl 1-ethyl-4-(3-methoxy-3-oxopropanamido)-3-methyl-1H-pyrazole-5-carboxylate.

Methyl 1-cyclopropyl-5,7-dihydroxy-3-methyl-1H-pyrazolo[4,3-b]pyridine-6-carboxylate was prepared in a similar way from ethyl 1-cyclopropyl-4-(3-methoxy-3-oxopropanamido)-3-methyl-1H-pyrazole-5-carboxylate.

Methyl 5,7-dihydroxy-1,3-dimethyl-1H-pyrazolo[4,3-b]pyridine-6-carboxylate was prepared in a similar way from ethyl 4-(3-methoxy-3-oxopropanamido)-1,3-dimethyl-1H-pyrazole-5-carboxylate.

(±)-Methyl 1-(sec-butyl)-5,7-dihydroxy-3-methyl-1H-pyrazolo[4,3-b]pyridine-6-carboxylate was prepared in a similar way from (±)-ethyl 1-(sec-butyl)-4-(3-methoxy-3-oxopropanamido)-3-methyl-1H-pyrazole-5-carboxylate.

Preparation of 1-isopropyl-3-methyl-1H-pyrazolo[4,3-b]pyridine-5,7-diol

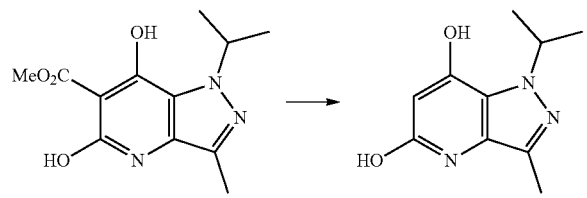 [SMILES: COC(=O)c1c(O)nc2c(C)nn(C(C)C)c2c1O ; Cc1nn(C(C)C)c2c(O)cc(O)nc12]

A mixture of methyl 5,7-dihydroxy-1-isopropyl-3-methyl-1H-pyrazolo[4,3-b]pyridine-6-carboxylate (10.62 g, 40.04 mmol) in aqueous NaOH (2 N, 150 mL) was stirred at 110° C. for 6 hours. The mixture was cooled to 0° C., then saturated aqueous KHSO₄ was added to adjust the pH to 218 3. The resulting mixture was filtered and the residue was washed with water (50 mL×3), then dried to give 1-isopropyl-3-methyl-1H-pyrazolo[4,3-b]pyridine-5,7-diol (7 g, 32.43 mmol, 81% yield). $^1$H NMR (DMSO-$d_6$ 400 MHz) δ 11.02 (brs, 1H), 5.50 (s, 1H), 5.11-5.08 (m, 1H), 2.24 (s, 3H), 1.37 (d, J=6.8 Hz, 6H).

1-(4-Methoxybenzyl)-3-methyl-1H-pyrazolo[4,3-b]pyridine-5,7-diol was prepared in a similar way from methyl 5,7-dihydroxy-1-(4-methoxybenzyl)-3-methyl-1H-pyrazolo[4,3-b]pyridine-6-carboxylate.

1-ethyl-3-methyl-1H-pyrazolo[4,3-b]pyridine-5,7-diol was prepared in a similar way from methyl 1-ethyl-5,7-dihydroxy-3-methyl-1H-pyrazolo[4,3-b]pyridine-6-carboxylate.

1-cyclopropyl-3-methyl-1H-pyrazolo[4,3-b]pyridine-5,7-diol was prepared in a similar way from methyl 1-cyclopropyl-5,7-dihydroxy-3-methyl-1H-pyrazolo[4,3-b]pyridine-6-carboxylate.

1,3-dimethyl-1H-pyrazolo[4,3-b]pyridine-5,7-diol was prepared in a similar way from 1-cyclopropyl-3-methyl-1H-pyrazolo[4,3-b]pyridine-5,7-diol.

(±)-1-(sec-Butyl)-3-methyl-1H-pyrazolo[4,3-b]pyridine-5,7-diol was prepared in a similar way from (±)-methyl 1-(sec-butyl)-5,7-dihydroxy-3-methyl-1H-pyrazolo[4,3-b]pyridine-6-carboxylate.

Preparation of 5,7-dichloro-1-isopropyl-3-methyl-1H-pyrazolo[4,3-b]pyridine

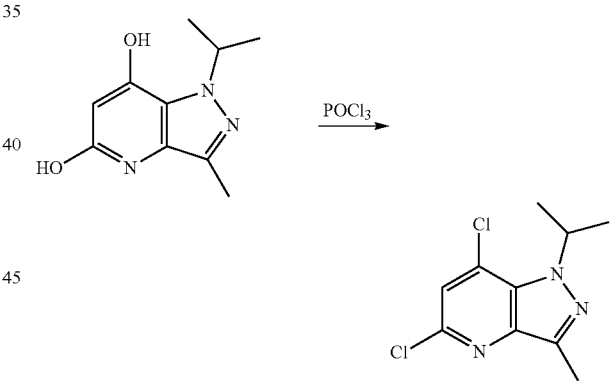

A mixture of 1-isopropyl-3-methyl-1H-pyrazolo[4,3-b]pyridine-5,7-diol (3.50 g, 16.9 mmol) in phosphoryl trichloride (30 mL) was stirred at 80° C. for 18 hours. The mixture was stirred at 85° C. for another 1 hour. The mixture was concentrated and then water (50 mL) was added slowly, followed by saturated aqueous NaHCO₃ to adjust pH to 7. The aqueous phase was extracted with ethyl acetate (70 mL×3), the combined organic layers were washed with brine (50 mL), dried over Na₂SO₄ and concentrated. The crude product was purified by flash chromatography with petroleum ether:ethyl acetate=20:1 to give 5,7-dichloro-1-isopropyl-3-methyl-1H-pyrazolo[4,3-b]pyridine (3.50 g, 14.3 mmol, 85% yield). $^1$H NMR (chloroform-d 400 MHz) δ 7.28 (s, 1H), 5.48-5.41 (m, 1H), 2.62 (s, 3H), 1.57 (d, J=4.8 Hz, 6H).

The following compounds were prepared in a similar manner:

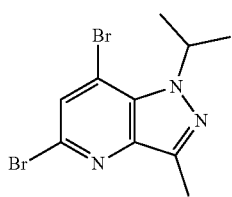

5,7-dibromo-1-isopropyl-3-methyl-1H-pyrazolo[4,3-b]pyridine from 1-isopropyl-3-methyl-1H-pyrazolo[4,3-b]pyridine-5,7-diol and phosphoryl tribromide. $^1$H NMR (chloroform-d 400 MHz) δ 7.60 (s, 1H), 5.61-5.55 (m, 1H), 2.63 (s, 3H), 1.57 (d, J=6.4 Hz, 6H).

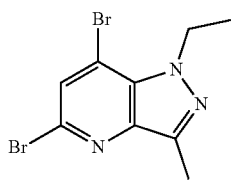

5,7-dibromo-1-ethyl-3-methyl-1H-pyrazolo[4,3-b]pyridine from 1-ethyl-3-methyl-1H-pyrazolo[4,3-b]pyridine-5,7-diol and phosphoryl tribromide

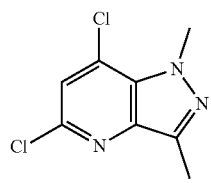

5,7-dichloro-1,3-dimethyl-1H-pyrazolo[4,3-b]pyridine from 1,3-dimethyl-1H-pyrazolo[4,3-b]pyridine-5,7-diol and phosphoryl trichloride. $^1$H NMR (chloroform-d 400 MHz) δ 7.29 (s, 1H), 4.29 (s, 3H), 2.60 (s, 3H).

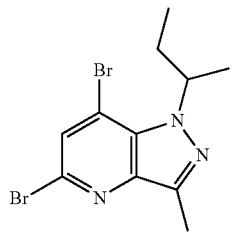 [SMILES: CCC(C)n1nc(C)c2nc(Br)cc(Br)c21]

(±)-5,7-Dibromo-1-(sec-butyl)-3-methyl-1H-pyrazolo[4,3-b]pyridine from (±)-1-(sec-butyl)-3-methyl-1H-pyrazolo[4,3-b]pyridine-5,7-diol and phosphoryl tribromide

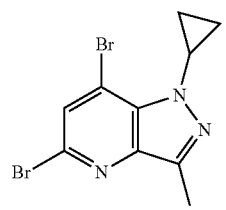

5,7-dibromo-1-cyclopropyl-3-methyl-1H-pyrazolo[4,3-b]pyridine from 1-cyclopropyl-3-methyl-1H-pyrazolo[4,3-b]pyridine-5,7-diol and phosphoryl tribromide. $^1$H NMR (chloroform-d 400 MHz) δ 7.63 (s, 1H), 3.99-3.88 (m, 1H), 2.57 (s, 3H), 1.41-1.38 (m, 2H), 1.22-1.19 (m, 2H).

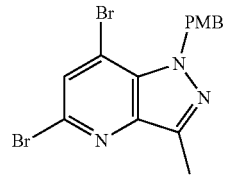

5,7-Dibromo-1-(4-methoxybenzyl)-3-methyl-1H-pyrazolo[4,3-b]pyridine from 1-(4-methoxybenzyl)-3-methyl-1H-pyrazolo[4,3-b]pyridine-5,7-diol and phosphoryl tribromide Preparation of 5,7-dibromo-3-methyl-1H-pyrazolo[4,3-b]pyridine

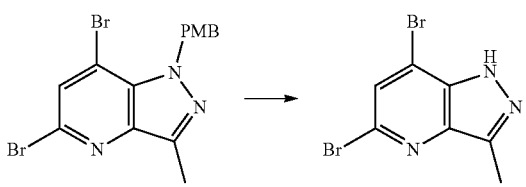

A solution of 5,7-dibromo-1-(4-methoxybenzyl)-3-methyl-1H-pyrazolo[4,3-b]pyridine (650 mg, 1.58 mmol) in TFA (5 mL) was heated at 80° C. for 2 hours. The mixture was concentrated and the residue was dissolved in H$_2$O (5 mL). The mixture was adjusted to pH 7 by saturated aqueous. NaHCO$_3$ and extracted with ethyl acetate (20 mL×2). The combined organic layers were washed with H$_2$O (20 mL), brine (20 mL), dried over Na$_2$SO$_4$, filtered and concentrated to give 5,7-dibromo-3-methyl-1H-pyrazolo[4,3-b]pyridine (450 mg, 1.55 mmol, 98% yield).

Preparation of 5,7-dibromo-3-methyl-1-(oxetan-3-yl)-1H-pyrazolo[4,3-b]pyridine

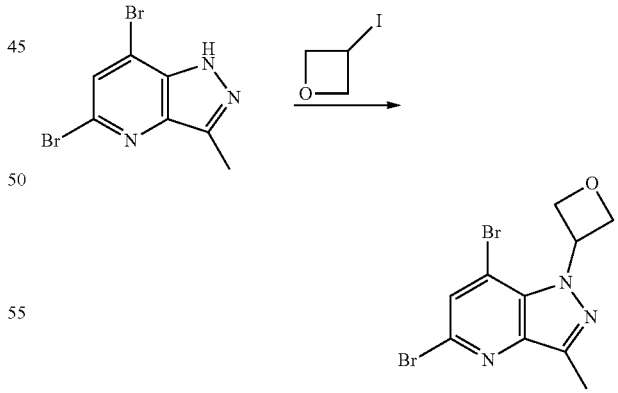

To a solution of 5,7-dibromo-3-methyl-1H-pyrazolo[4,3-b]pyridine (340 mg, 1.17 mmol) in dry DMF (10 mL) was added 3-iodooxetane (323 mg, 1.76 mmol) and Cs$_2$CO$_3$ (762 mg, 2.34 mmol). The mixture was heated under microwave at 100° C. for 1 hour. The mixture was concentrated and water (20 mL) was added. The mixture was extracted with ethyl acetate (20 mL×2). The combined organic layers were washed with H$_2$O (20 mL×2), brine (20 mL), dried over Na₂SO₄, filtered and concentrated. The residue was purified by flash chromatography on silica gel (0% to 50% ethyl acetate in petroleum ether) to give 5,7-dibromo-3-methyl-1-(oxetan-3-yl)-1H-pyrazolo[4,3-b]pyridine (200 mg, 49% yield).

Preparation of (+5,7-dibromo-1-(sec-butyl)-3-methyl-1H-pyrazolo[4,3-b]pyridine and (+)-5,7-dibromo-1-(sec-butyl)-3-methyl-1H-pyrazolo[4,3-b]pyridine

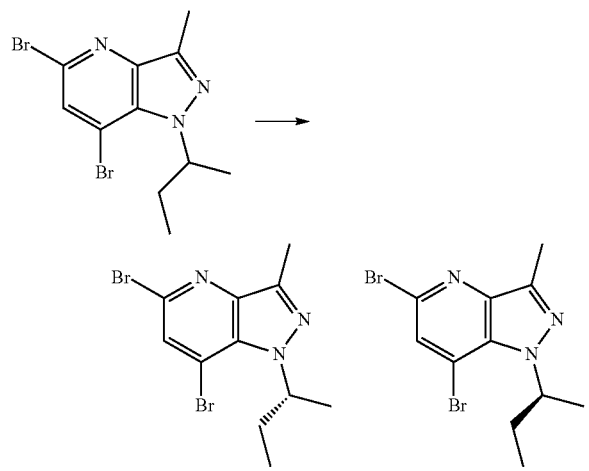

(±)-5,7-dibromo-1-(sec-butyl)-3-methyl-1H-pyrazolo[4,3-b]pyridine (2.2 g, 6.34 mmol) was purified by SFC twice to give (+)-5,7-dibromo-1-(sec-butyl)-3-methyl-1H-pyrazolo[4,3-b]pyridine (800 mg) (Rt=6.25 min) and (+5,7-dibromo-1-(sec-butyl)-3-methyl-1H-pyrazolo[4,3-b]pyridine (900 mg) (Rt=6.28 min).

(+)-5,7-dibromo-1-(sec-butyl)-3-methyl-1H-pyrazolo[4,3-b]pyridine ¹H NMR (Chloroform-d, 400 MHz): δ 7.60 (s, 1H), 5.41-5.32 (m, 1H), 2.63 (s, 3H), 2.13-2.07 (m, 1H), 1.87-1.83 (m, 1H), 1.54 (d, J=6.4 Hz, 3H), 0.79 (t, J=7.6 Hz, 3H). SFC-MS: $t_R$=6.25 min, ee %=100%; $[\alpha]_D^{20}$=2.60 (c=1.0, dichloromethane).

(−)-5,7-dibromo-1-(sec-butyl)-3-methyl-1H-pyrazolo[4,3-b]pyridinel-H NMR (Chloroform-d, 400 MHz): δ 7.60 (s, 1H), 5.41-5.32 (m, 1H), 2.63 (s, 3H), 2.13-2.07 (m, 1H), 1.87-1.83 (m, 1H), 1.55 (d, J=6.8 Hz, 3H), 0.79 (t, J=7.6 Hz, 3H). SFC-MS: $t_R$=6.5 min, ee %=97.87%; $[\alpha]_D^{20}$=−2.90 (c=1.0, dichloromethane).

SFC Condition 1:

Instrument: Thar SFC 1; Column: (s,s) WHELK-01 (250 mm×30 mm, 5 μm); Mobile phase: A: Supercritical CO₂, B: isopropyl alcohol (0.1% NH₃H₂O), A:B=85:15 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm SFC Condition 2:

Instrument: Thar SFC-13; Column: (s,s) WHELK-01 (250 mm×30 mm, 5 μm); Mobile phase: A: Supercritical CO₂, B: isopropyl alcohol (0.1% NH₃H₂O), A:B=85:15 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm Preparation of 4,6-dibromo-2-methylpyridin-3-amine

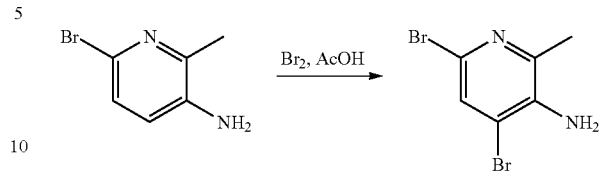

A solution of 6-bromo-2-methylpyridin-3-amine (24 g, 128 mmol) and AcOH (14.7 mL 257 mmol) in MeOH (200 mL) was cooled to 0° C., Br₂ (36.9 g, 230.9 mmol, 11.9 mL) was added and stirred at 0° C. for 5 hours. The mixture was quenched with saturated aqueous Na₂SO₃ (500 mL), extracted with ethyl acetate (300 mL×3). The organic layer was washed with brine (200 mL), dried over Na₂SO₄, and concentrated in vacuo. The residue was purified by silica gel chromatography (petroleum ether:ethyl acetate=2:1) to afford 4,6-dibromo-2-methylpyridin-3-amine (30 g, 87% yield).

Preparation of 5,7-dibromo-1H-pyrazolo[4,3-b]pyridine

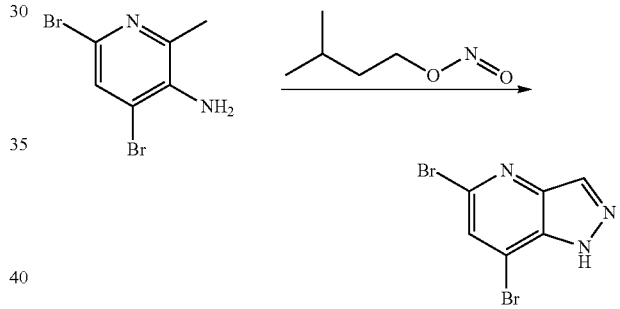

To a mixture of 4,6-dibromo-2-methylpyridin-3-amine (15.0 g, 56.4 mmol) and AcOK (13.8 g, 141 mmol) in AcOH (30 mL) and toluene (200 mL) was added isopentyl nitrite (13.2 g, 112.8 mmol). The mixture was stirred at 25° C. for 1 hour then at 60° C. for 19 hours. The mixture was concentrated in vacuo, diluted with water (300 mL) and extracted with ethyl acetate (200 mL×2). The organic layer was washed with brine (100 mL), dried over Na₂SO₄ and concentrated in vacuo to give 5,7-dibromo-1H-pyrazolo[4,3-b]pyridine (5.4 g, 30% yield).

Preparation of 5,7-dibromo-1-ethyl-1H-pyrazolo[4,3-b]pyridine

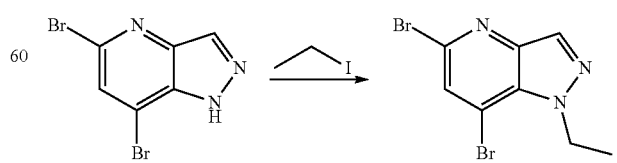

To a mixture of 5,7-dibromo-1H-pyrazolo[4,3-b]pyridine (1 g, 3.6 mmol) and Cs₂CO₃ (12.4 g, 7.2 mmol) in anhydrous DMF (10 mL) was added iodoethane (0.8 g, 5.4 mmol). The mixture was stirred at 0° C. for 0.5 hours. The mixture was diluted with water (20 mL), extracted with ethyl acetate (30 mL×2). The organic layer was washed with water (20 mL), brine (20 mL) and dried with $Na_2SO_4$, concentrated in vacuo. The residue was purified by silica gel chromatography (petroleum ether:ethyl acetate=10:1-5:1) to give 5,7-dibromo-1-ethyl-1H-pyrazolo[4,3-b]pyridine (0.56 g, 51% yield). $^1$H NMR (DMSO-$d_6$ 400 MHz) δ 8.37 (s, 1H), 7.98 (s, 1H), 4.72 (q, J=7.2 Hz, 2H), 1.42 (t, J=7.2 Hz, 3H).

The following compounds were prepared in a similar manner:

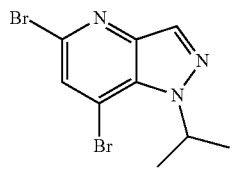

5,7-Dibromo-1-isopropyl-1H-pyrazolo[4,3-b]pyridine from 5,7-dibromo-1H-pyrazolo[4,3-b]pyridine and 2-iodopropane. $^1$H NMR (DMSO-$d_6$ 400 MHz) δ 8.36 (s, 1H), 7.94 (s, 1H), 5.62-5.55 (m, 1H), 1.49 (d, J=6.0 Hz, 6H).

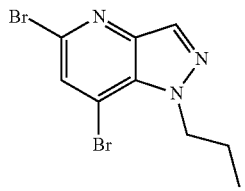

5,7-Dibromo-1-propyl-1H-pyrazolo[4,3-b]pyridine from 5,7-dibromo-1H-pyrazolo[4,3-b]pyridine and 1-iodopropane. $^1$H NMR (chloroform-d 400 MHz) δ 8.14 (s, 1H), 7.64 (s, 1H), 4.67 (t, J=7.2 Hz, 2H), 1.98-1.89 (m, 2H), 0.94 (t, J=7.6 Hz, 3H).

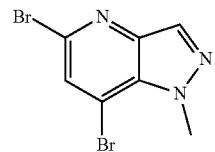

5,7-Dibromo-1-methyl-1H-pyrazolo[4,3-b]pyridine from 5,7-dibromo-1H-pyrazolo[4,3-b]pyridine and iodomethane. $^1$H NMR (chloroform-d 400 MHz) δ 8.13 (s, 1H), 7.64 (s, 1H), 4.38 (s, 3H).

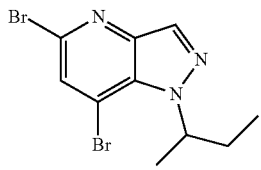

(±)-5,7-Dibromo-1-(sec-butyl)-3-methyl-1H-pyrazolo[4,3-b]pyridine from 5,7-dibromo-1H-pyrazolo[4,3-b]pyridine and (±)-2-iodobutane.

Preparation of (+)-5,7-dibromo-1-(sec-butyl)-1H-pyrazolo[4,3-b]pyridine and (−)-5,7-dibromo-1-(sec-butyl)-1H-pyrazolo[4,3-b]pyridine

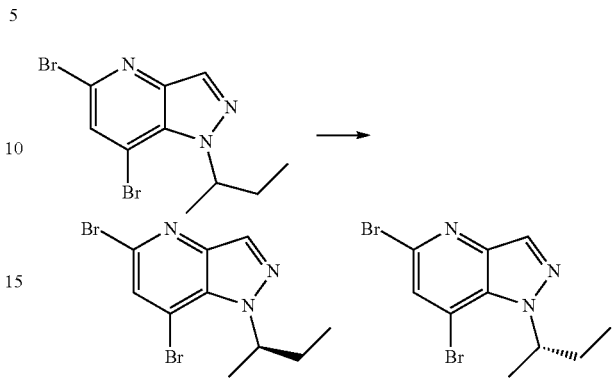

(±)-5,7-dibromo-1-sec-butyl-pyrazolo[4,3-b]pyridine (5.2 g, 15.6 mmol) was separated by SFC with column: AD (250 mm*50 mm, 10 μm); mobile phase: [0.1% $NH_3H_2O$ in isopropyl alcohol]; B %: 20%-20%, min.

(+)-5,7-dibromo-1-(sec-butyl)-1H-pyrazolo[4,3-b]pyridine (2.5 g) (Rt=3.137 min) ($[α]_D^{20}$=1.40) (c=1.0, ethanol).

(−)-5,7-dibromo-1-(sec-butyl)-1H-pyrazolo[4,3-b]pyridine (2.5 g) (Rt=2.808 min) ($[α]_D^{20}$=−1.60) (c=1.0, ethanol).

Preparation of 5-chloro-1-isopropyl-N-(4-methoxybenzyl)-3-methyl-1H-pyrazolo[4,3-b]pyridin-7-amine

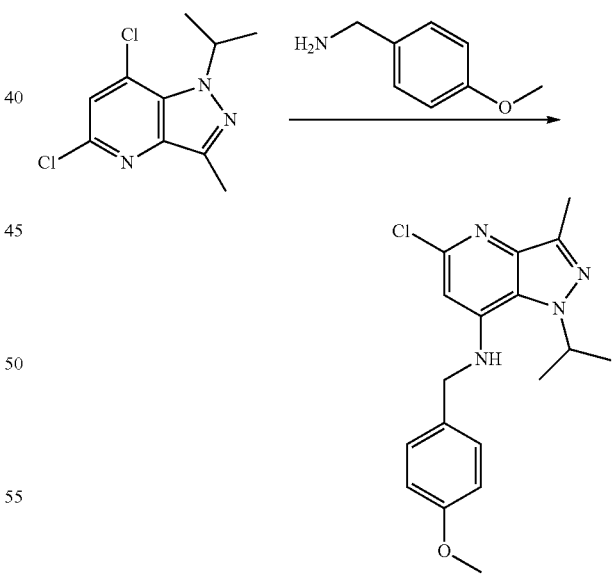

To a solution of 5,7-dichloro-1-isopropyl-3-methyl-1H-pyrazolo[4,3-b]pyridine (100 mg, 410 μmol) and (4-methoxyphenyl)methanamine (67 mg, 492 μmol, 64 μL) in NMP (5 mL) was added CsF (124 mg, 819 μmol, 30 μL). The mixture was stirred at 100° C. for 18 hours. Water (20 mL) was added and the mixture was filtered and concentrated in vacuo. The crude mixture was purified by flash chromatography with petroleum ether:ethyl acetate=3:1 to give 5-chloro-1-isopropyl-N-(4-methoxybenzyl)-3-methyl-1H-pyrazolo[4,3-b]pyridin-7-amine (80 mg, 215 μmol, 53% yield). ¹H NMR (chloroform-d 400 MHz) δ 7.32 (d, J=8.4 Hz, 2H), 6.95 (d, J=8.4 Hz, 2H), 6.39 (s, 1H), 4.79 (brs, 1H), 4.70-4.63 (m, 1H), 4.39 (d, J=4.4 Hz, 2H), 3.85 (s, 3H), 2.56 (s, 3H), 1.57 (d, J=6.4 Hz, 6H).

Preparation of 5-(2-ethoxypyridin-3-yl)-1-isopropyl-N-(4-methoxybenzyl)-3-methyl-1H-pyrazolo[4,3-b]pyridin-7-amine

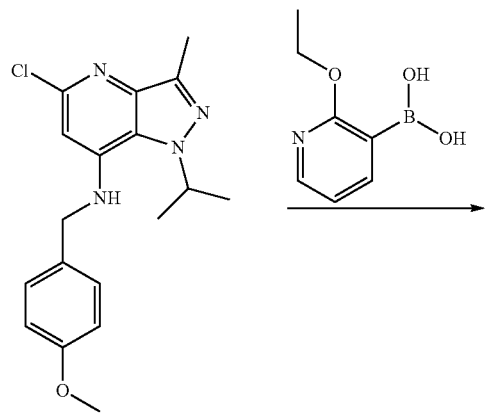

To a solution of 5-chloro-1-isopropyl-N-(4-methoxybenzyl)-3-methyl-1H-pyrazolo[4,3-b]pyridin-7-amine (60 mg, 174 μmop in dioxane (2 mL) and H₂O (0.5 mL) was added Pd(1,1'-bis(diphenylphosphino)ferrocene)Cl₂ (25 mg, 35 μmop and Cs₂CO₃ (141.72 mg, 435 μmol) and (2-ethoxypyridin-3-yl)boronic acid (52 mg, 313 μmol). The mixture was stirred at 100° C. for 1 hour under microwave irradiation. Water (30 mL) was added and the mixture was extracted with ethyl acetate (30 mL×3). The combined organic layers were washed with brine (20 mL), dried over Na₂SO₄ and concentrated. The crude mixture was purified by flash chromatography with petroleum ether:ethyl acetate=1:1 to 0:1 to give 5-(2-ethoxypyridin-3-yl)-1-isopropyl-N-(4-methoxybenzyl)-3-methyl-1H-pyrazolo[4,3-b]pyridin-7-amine (50 mg, 67% yield). ¹H NMR (chloroform-d 400 MHz) δ 8.27-8.25 (m, 1H), 8.17-8.16 (m, 1H), 7.32 (d, J=8.8 Hz, 2H), 7.22 (s, 1H), 7.03-7.00 (m, 1H), 6.95 (d, J=8.4 Hz, 2H), 4.81-4.76 (m, 1H), 4.65 (brs, 1H), 4.47-4.41 (m, 4H), 3.84 (s, 3H), 2.65 (s, 3H), 1.60 (d, J=6.4 Hz, 6H), 1.36 (t, J=7.2 Hz, 3H).

The following compounds were prepared in a similar manner:

5-(2-Fluoropyridin-3-yl)-1-isopropyl-N-(4-methoxybenzyl)-3-methyl-1H-pyrazolo[4,3-b]pyridin-7-amine

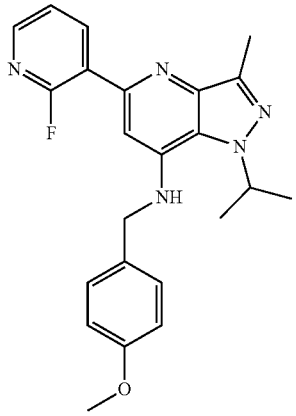 [SMILES: COc1ccc(CNc2cc(-c3cccnc3F)nc3c(C)nn(C(C)C)c23)cc1]

Prepared from 5-bromo-1-isopropyl-N-(4-methoxybenzyl)-3-methyl-1H-pyrazolo[4,3-b]pyridin-7-amine and (2-fluoropyridin-3-yl)boronic acid Preparation of 5-(2-ethoxypyridin-3-yl)-1-isopropyl-3-methyl-1H-pyrazolo[4,3-b]pyridin-7-amine

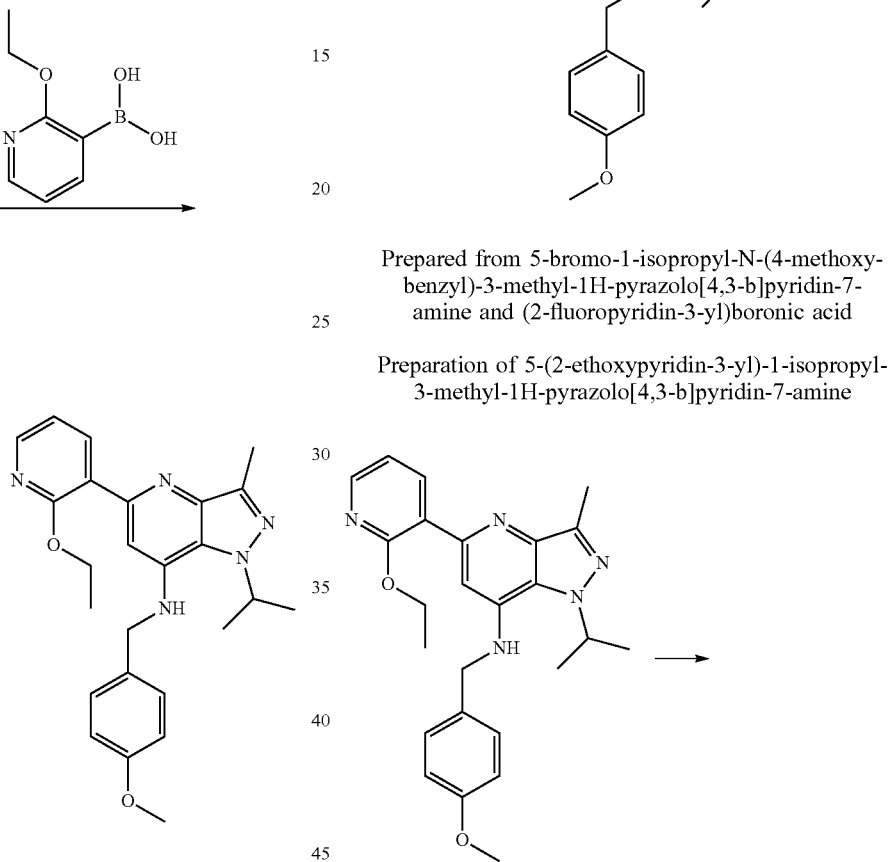

A solution of 5-(2-ethoxypyridin-3-yl)-1-isopropyl-N-(4-methoxybenzyl)-3-methyl-1H-pyrazolo[4,3-b]pyridin-7-amine (1.25 g, 2.90 mmol) in TFA (15 mL) was stirred at 60° C. for 18 hours. The mixture was concentrated and the residue was dissolved in ethyl acetate (200 mL). The resulting mixture was washed with saturated aqueous NaHCO₃ (30 mL), brine (20 mL), dried over Na₂SO₄ and concentrated. The crude mixture was purified by flash chromatography with petroleum ether:ethyl acetate=3:1 to 2:1 to give 5-(2-ethoxypyridin-3-yl)-1-isopropyl-3-methyl-1H-pyrazolo[4,3-b]pyridin-7-amine (900 mg, 96% yield).

The following compounds were prepared in a similar manner:

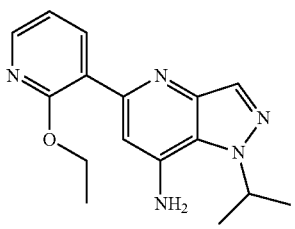 [SMILES: CCOc1ncccc1-c1cc(N)c2c(cnn2C(C)C)n1]

5-(2-Ethoxypyridin-3-yl)-1-isopropyl-1H-pyrazolo[4,3-b]pyridin-7-amine

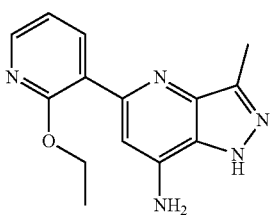 [SMILES: CCOc1ncccc1-c1cc(N)c2[nH]nc(C)c2n1]

5-(2-Ethoxypyridin-3-yl)-3-methyl-1H-pyrazolo[4,3-b]pyridin-7-amine

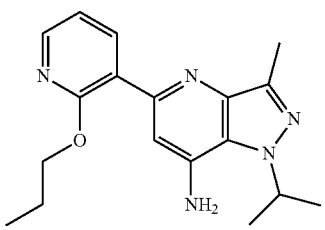 [SMILES: CCCOc1ncccc1-c1cc(N)c2c(n1)c(C)nn2C(C)C]

1-Isopropyl-3-methyl-5-(2-propoxypyridin-3-yl)-1H-pyrazolo[4,3-b]pyridin-7-amine

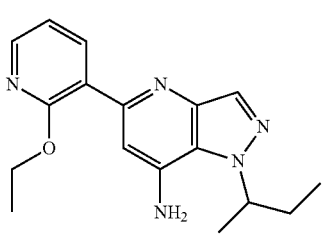

1-(sec-Butyl)-5-(2-ethoxypyridin-3-yl)-1H-pyrazolo[4,3-b]pyridin-7-amine, enantiomer 1, prepared from (+)-5,7-dibromo-1-(sec-butyl)-1H-pyrazolo[4,3-b]pyridine

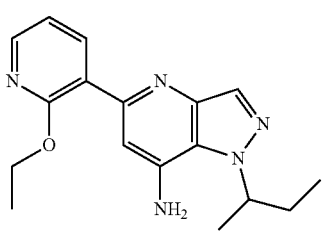 [SMILES: CCOc1ncccc1-c1cc(N)c2c(cnn2C(C)CC)n1]

1-(sec-Butyl)-5-(2-ethoxypyridin-3-yl)-1H-pyrazolo[4,3-b]pyridin-7-amine, enantiomer 2, prepared from (+5,7-dibromo-1-(sec-butyl)-1H-pyrazolo[4,3-b]pyridine

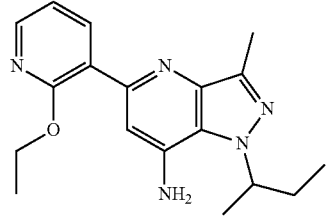 [SMILES: CCOc1ncccc1-c1cc(N)c2c(n1)c(C)nn2C(C)CC]

1-(sec-Butyl)-5-(2-ethoxypyridin-3-yl)-3-methyl-1H-pyrazolo[4,3-b]pyridin-7-amine, enantiomer 1, prepared from (+)-5,7-dibromo-1-(sec-butyl)-3-methyl-1H-pyrazolo[4,3-b]pyridine

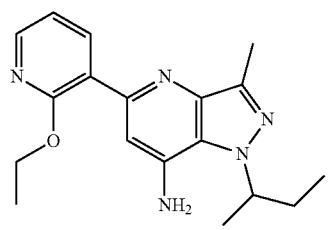

1-(sec-Butyl)-5-(2-ethoxypyridin-3-yl)-3-methyl-1H-pyrazolo[4,3-b]pyridin-7-amine, enantiomer 2, prepared from (+5,7-dibromo-1-(sec-butyl)-3-methyl-1H-pyrazolo[4,3-b]pyridine 1-Isopropyl-5-(2-methoxypyridin-3-yl)-3-methyl-1H-pyrazolo[4,3-b]pyridin-7-amine

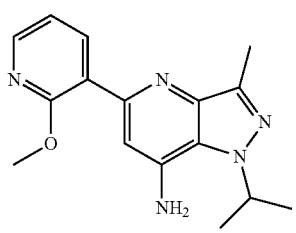 [SMILES: COc1ncccc1-c1cc(N)c2c(n1)c(C)nn2C(C)C]

Prepared from 1-isopropyl-N-(4-methoxybenzyl)-5-(2-methoxypyridin-3-yl)-3-methyl-1H-pyrazolo[4,3-b]pyridin-7-amine Preparation of 1-methyl-1H-1,2,4-triazole-3-carbaldehyde

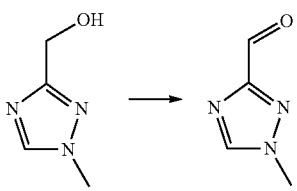

To a mixture of (1-methyl-1H-1,2,4-triazol-3-yl)methanol (400 mg, 3.54 mmol) and iodobenzene diacetate (1.25 g, 3.89 mmol) in dichloromethane (10 mL) was added TEMPO ((2,2,6,6-tetramethylpiperidin-1-yl)oxyl) (56 mg, 354 μmop. The mixture was stirred at 15-20° C. for 2 h. The mixture was concentrated in vacuo. The residue was purified by silica gel chromatography (petroleum ether:ethyl acetate=1: 2) to give 1-methyl-1H-1,2,4-triazole-3-carbaldehyde (300 mg, 2.70 mmol, 76% yield). $^1$H NMR (chloroform-d 400 MHz) δ 10.01 (s, 1H), 8.19 (s, 1H), 4.06 (s, 3H).

Preparation of (5-methylthiophen-3-yl)methanol

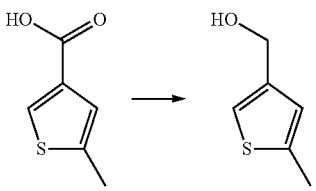

To a solution of 5-methylthiophene-3-carboxylic acid (300 mg, 2.11 mmol) in THF (10 mL) was added LiAlH$_4$ (120 mg, 3.17 mmol) slowly at 0° C. The mixture was stirred at 20° C. for 2 hours. Water (0.3 mL) was added at 0° C. to quench the reaction mixture followed by addition of 15% aqueous NaOH (0.3 mL). Ethyl acetate (50 mL) was added to the mixture, the mixture was filtered and the residue was washed with ethyl acetate (20 mL×2). The combined filtrates were dried over Na$_2$SO$_4$ and concentrated to give (5-methylthiophen-3-yl)methanol (270 mg).

Preparation of 5-methylthiophene-3-carbaldehyde

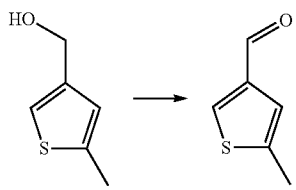

To a solution of (5-methylthiophen-3-yl)methanol (270 mg, 2.11 mmol) in dichloromethane (10 mL) was added Dess-Martin reagent (1,1,1-triacetoxy-1,1-dihydro-1,2-benziodoxol-3(1H)-one) (1.07 g, 2.53 mmol). The mixture was stirred at 20° C. for 1 hour. The mixture was filtered and the residue was washed with dichloromethane (30 mL), the combined organic layers were concentrated. The crude mixture was purified by flash chromatography with petroleum ether: ethyl acetate=5:1 to give 5-methylthiophene-3-carbaldehyde (180 mg, 1.43 mmol, 68% yield). $^1$H NMR (chloroform-d 400 MHz) δ 9.81 (s, 1H), 7.89 (s, 1H), 7.20 (s, 1H), 2.51 (s, 3H).

The following compound was prepared in a similar manner:

5-methyl-1,2,4-oxadiazole-3-carbaldehyde from (5-methyl-1,2,4-oxadiazol-3-yl)methanol Preparation of 1-((1-aminoethyl)thio)-3-chloropropan-2-one

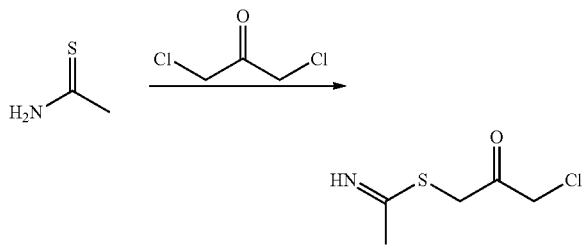

A solution of ethanethioamide (1 g, 13.3 mmol) in acetone (7 mL) was added dropwise to a solution of 1,3-dichloropropan-2-one (1.69 g, 13.3 mmol, 1.66 mL) in acetone (5 mL) at 20° C. and stirred at 20° C. for 12 hours. The mixture was filtered and the filter cake was washed with acetone (10 mL×3) to give 1-((1-aminoethyl)thio)-3-chloropropan-2-one.

Preparation of 4-(chloromethyl)-2-methylthiazole

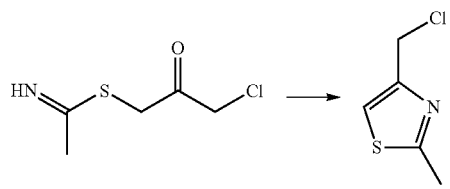

A mixture of 1-((1-aminoethyl)thio)-3-chloropropan-2-one (3 g, 17.9 mmol) in ethanol (30 mL) was stirred at 80° C. for 2 h. The mixture was concentrated in vacuo to give 4-(chloromethyl)-2-methylthiazole (2.9 g).

Preparation of 2-((2-methylthiazol-4-yl)methyl) isoindoline-1,3-dione

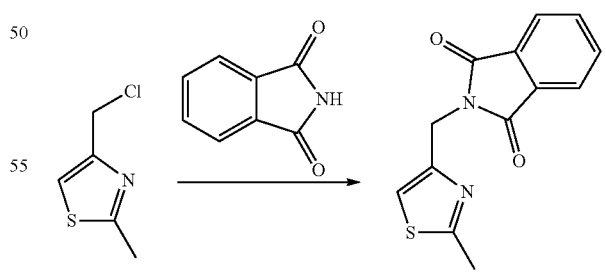

To a mixture of 4-(chloromethyl)-2-methylthiazole (2.80 g, 19.0 mmol) and isoindoline-1,3-dione in anhydrous DMF (30 mL) was added K$_2$CO$_3$ (1.31 g, 9.49 mmol). The mixture stirred at 100° C. for 0.5 hour. The mixture was diluted with water (50 mL), extracted with ethyl acetate (50 mL×2). The organic layer was washed with water (30 mL), brine (30 mL), dried with Na$_2$SO$_4$ and concentrated in vacuo. The residue was purified by silica gel chromatography (petroleum ether:ethyl acetate=10:1-2:1) to give 2-((2-methylthiazol-4-yl)methyl)isoindoline-1,3-dione (3.29 g).

Preparation of (2-methylthiazol-4-yl)methanamine

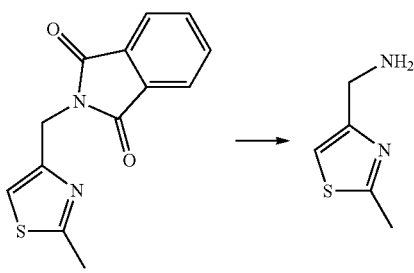

A mixture of 2-((2-methylthiazol-4-yl)methyl)isoindoline-1,3-dione (1 g, 3.87 mmol) and hydrazine hydrate (291 mg, 5.81 mmol, 282 μL) in ethanol (10 mL) was stirred at 20° C. for 0.5 hour. The mixture was concentrated in vacuo. The residue was purified by silica gel chromatography (dichloromethane:methanol=0:1 to 10:1) to give (2-methylthiazol-4-yl)methanamine (330 mg).

Preparation of m-tolylmethanamine hydrochloride

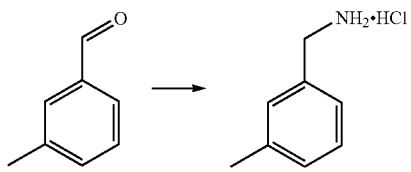

A mixture 3-methylbenzaldehyde (500 mg, 4.16 mmol, 490.20 μL) in NH$_3$/MeOH (7 M, 1 mL) was stirred at 80° C. for 14 hours. Then NaBH$_4$ (315 mg, 8.32 mmol) was added and the reaction mixture was stirred at 20° C. for 1 hour. The mixture was diluted with water (20 mL) and extracted with ethyl acetate (20 mL×2). The organic layers were washed with water (10 mL), brine (10 mL), dried with Na$_2$SO$_4$ and concentrated in vacuo. The residue was purified by preparative HPLC to give m-tolylmethanamine (370 mg) as the HCl salt.

Preparation of 4-bromo-6-chloro-2-methylpyridin-3-amine

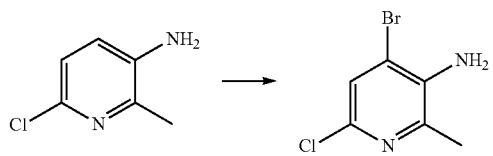

To an ice cold solution of 6-chloro-2-methylpyridin-3-amine (12 g, 84 mmol) and AcOH (5.1 g, 84 mmol) in MeOH (198 g, 250 mL) was dropwise added bromine (13.5 g, 84 mmol). The resulting solution was stirred at ice bath temperature overnight after which it was concentrated under vacuo. The obtained residue was dissolved in EtOAc and sequentially washed with saturated aqueous NaHCO$_3$ solution, 10% Na$_2$S$_2$O$_3$ aqueous solution, brine and dried (Na$_2$SO$_4$). The solvent was removed under vacuo and the obtained crude material was purified by flash chromatography to afford 4-bromo-6-chloro-2-methylpyridin-3-amine (12.6 g). $^1$H NMR (500 MHz, Chloroform-d) δ 7.30 (s, 1H), 4.04 (brs, 2H), 2.46 (s, 3H).

Preparation of 7-bromo-5-chloro-1H-pyrazolo[4,3-b]pyridine

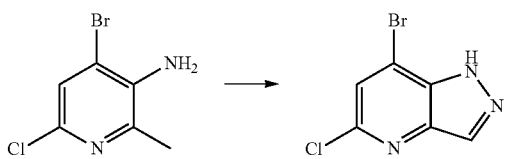

Isopentyl nitrite (3.97 g, 33.9 mmol) was dropwise added to an ice cold suspension of 4-bromo-6-chloro-2-methylpyridin-3-amine (5 g, 22.6 mmol), KOAc (4.43 g, 45.2 mmol) and AcOH (44.1 g, 734 mmol) in toluene (125 mL) under an inert atmosphere. A reflux condenser was inserted and the reaction mixture was heated at 30° C. over 4 h, after which most of the solvent was removed under vacuo. The obtained residue was dissolved in ethyl acetate and carefully washed with saturated aqueous NaHCO$_3$ solution ensuring that pH 8-9 was obtained. The organic layer was washed with brine, dried (Na$_2$SO$_4$) and concentrated to a crude material which was purified by flash chromatography (SiO$_2$) to deliver 7-bromo-5-chloro-1H-pyrazolo[4,3-b]pyridine (2.3 g, 44% yield). $^1$H NMR (500 MHz, Chloroform-d) δ 10.61 (brs, 1H), 8.35 (s, 1H), 7.60 (s, 1H)

Preparation of 7-bromo-5-chloro-1-(oxetan-3-yl)-1H-pyrazolo[4,3-b]pyridine

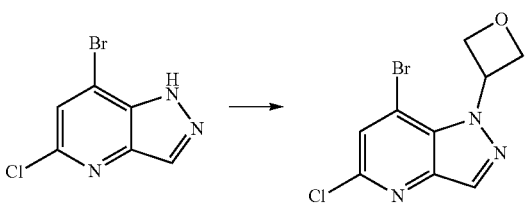 [SMILES: Clc1cc(Br)c2[nH]ncc2n1 ; Clc1cc(Br)c2c(cnn2C2COC2)n1]

Diisopropyl azodicarboxylate (979 mg, 4.84 mmol) was dropwise added to an ice cold solution of 7-bromo-5-chloro-1H-pyrazolo[4,3-b]pyridine (250 mg, 1.08 mmol), triphenylphosphine (1.27 g, 4.84 mmol) and oxetan-3-ol (319 mg, 4.30 mmol) in THF (10 mL) under an inert atmosphere. The ice bath was allowed to warm to room temperature and stirring continued at room temperature overnight. Most of the solvent was removed under vacuo and the crude material obtained was purified by flash chromatography delivering 7-bromo-5-chloro-1-(oxetan-3-yl)-1H-pyrazolo[4,3-b]pyridine (130 mg, 38% yield). $^1$H NMR (Chloroform-d, 500 MHz) δ 8.31 (s, 1H), 7.56 (s, 1H), 6.48 (p, J=6.9 Hz, 1H), 5.35 (t, J=6.5 Hz, 2H), 5.11 (t, J=7.1 Hz, 2H).

Preparation of 5-bromo-1-isopropyl-3-methyl-1H-pyrazolo[4,3-b]pyridine-7-carbaldehyde

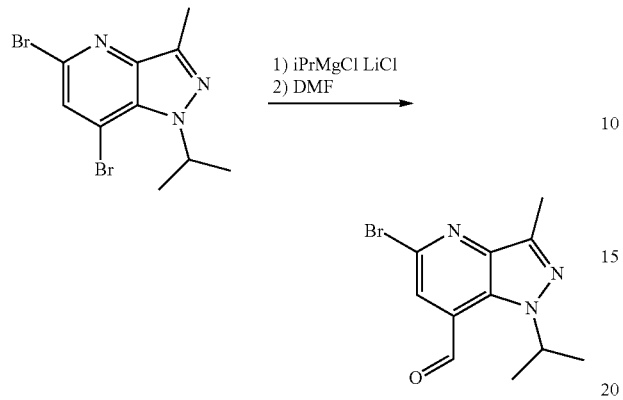

A solution of i-PrMgCl—LiCl (1.3 M, 3.6 mL) in THF was dropwise added into a mixture of 5,7-dibromo-1-isopropyl-3-methyl-pyrazolo[4,3-b]pyridine (1.3 g, 3.9 mmol) in THF (25 mL) at 0° C. The mixture was stirred at room temperature for 30 min. Then the mixture was recooled to 0° C. and DMF (1.4 g, 19.5 mmol, 1.5 mL) was added and the resulting mixture was stirred at room temperature for another 2.5 hours. $NH_4Cl$ (aq. 2 mL) was added to quench the reaction, then water (20 mL) was added and the mixture was extracted with ethyl acetate (20 mL×3). The combined organic layer was washed with brine (10 mL), dried over $Na_2SO_4$ and concentrated. The crude mixture was purified by flash chromatography with petroleum ether:ethyl acetate=30:1~20:1 to give 5-bromo-1-isopropyl-3-methyl-1H-pyrazolo[4,3-b]pyridine-7-carbaldehyde (800 mg).

Preparation of N-((5-bromo-1-isopropyl-3-methyl-1H-pyrazolo[4,3-b]pyridin-7-yl)methyl)-5-methoxy-pyridin-3-amine To a solution of 5-bromo-1-isopropyl-3-methyl-pyrazolo[4,3-b]pyridine-7-carbaldehyde (50 mg, 0.18 mmol) in dioxane (3 mL) was added Ti(i-PrO)$_4$ (101 mg, 0.35 mmol) and 5-methoxypyridin-3-amine (44 mg, 0.35 mmol). The mixture was stirred at 80° C. for 14 hours. After the reaction mixture had cooled to room temperature, EtOH (3 mL) was added followed by addition of NaBH$_4$ (35 mg, 0.9 mmol). The mixture was stirred at room temperature for 15 minutes. Water (0.5 mL) was added to quench the reaction at 0° C. And the resulting mixture was stirred at room temperature for 10 minutes, then filtered and the residue was washed with ethyl acetate (30 mL×3). The combined organic layers was dried and concentrated. The crude product N-[(5-bromo-1-isopropyl-3-methyl-pyrazolo[4,3-b]pyridin-7-yl)methyl]-5-methoxy-pyridin-3-amine (69 mg) was used into the next step without further purification.

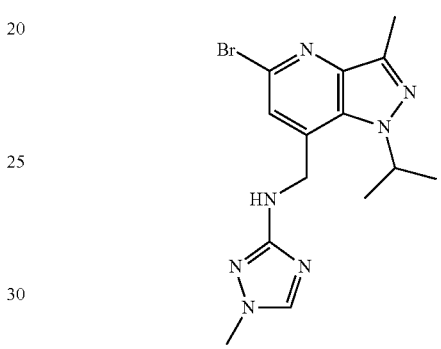

N-((5-bromo-1-isopropyl-3-methyl-1H-pyrazolo[4,3-b]pyridin-7-yl)methyl)-1-methyl-1H-1,2,4-triazol-3-amine was prepared in similar manner from 5-bromo-1-isopropyl-3-methyl-pyrazolo[4,3-b]pyridine-7-carbaldehyde and 1-methyl-1,2,4-triazol-3-amine.

Preparation of 5-(2-ethoxypyridin-3-yl)-1-isopropyl-3-methyl-1H-pyrazolo[4,3-b]pyridine-7-carbaldehyde

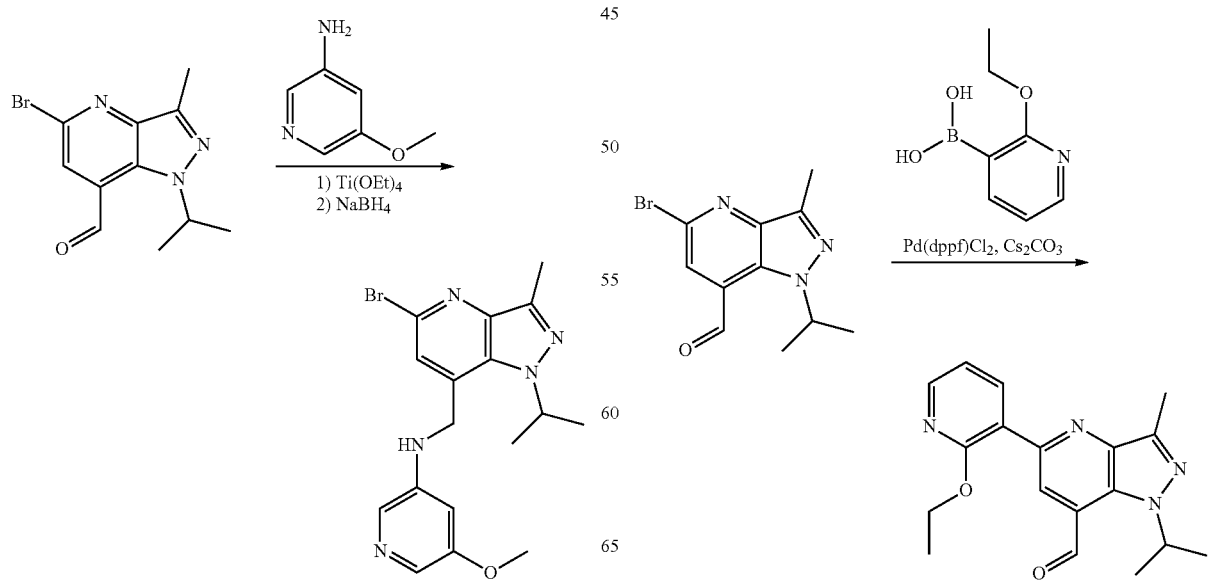

A mixture of 5-bromo-1-isopropyl-3-methyl-1H-pyrazolo[4,3-b]pyridine-7-carbaldehyde (0.56 g, 1.98 mmol), (2-ethoxy-3-pyridyl)boronic acid (497 mg, 2.98 mmol), Pd(dppf)Cl$_2$ (145 mg, 0.2 mmol), Cs$_2$CO$_3$ (1.94 g, 5.95 mmol) in dioxane (8 mL), water (2 mL) was stirred at 100° C. for 2 hours. The mixture was concentrated under reduced pressure. The residue was extracted with ethyl acetate (30 mL×2). The combined organic layers were washed with brine (20 mL), dried over Na$_2$SO$_4$, filtered and concentrated under reduced pressure to give a residue. The residue was purified by column chromatography (SiO$_2$, Petroleum ether/Ethyl acetate=10:1 to 3:1) to give 5-(2-ethoxypyridin-3-yl)-1-isopropyl-3-methyl-1H-pyrazolo[4,3-b]pyridine-7-carbaldehyde (0.55 g).

Preparation of 6-methylheptyl 3-((5-bromo-1-isopropyl-3-methyl-1H-pyrazolo[4,3-b]pyridin-7-yl)thio)propanoate

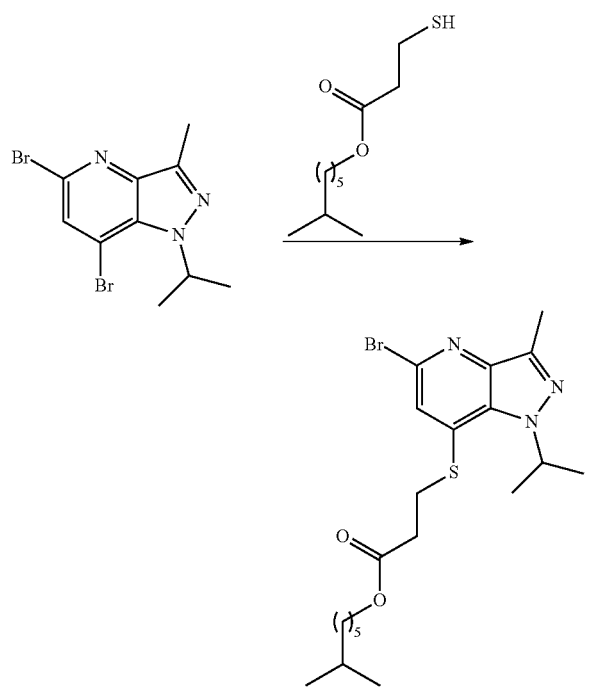

A solution of 5,7-dibromo-1-isopropyl-3-methyl-1H-pyrazolo[4,3-b]pyridine (150 mg, 0.45 mmol), 6-methylheptyl 3-mercaptopropanoate (124 mg, 0.57 mmol), DIPEA (116 mg, 157 µL, 0.90 mmol) in NMP (2 mL) was stirred at rt under inert atmosphere over 15 minutes after which it was inserted in an oil bath at 50° C. and stirred overnight. Partitioned between water (25 mL) and a solution of pentane:ethyl acetate (1:1) (50 mL). The aq. layer was extracted with fresh pentane:ethyl acetate (1:1) (20 mL). The combined org. layers were dried (Na$_2$SO$_4$) and concentrated. The crude material was purified by flash chromatography with heptane:ethyl acetate 1:0 to 0:1 to give 6-methylheptyl 3-((5-bromo-1-isopropyl-3-methyl-1H-pyrazolo[4,3-b]pyridin-7-yl)thio)propanoate (194 mg).

Preparation of methyl 1-(difluoromethyl)-1H-pyrazole-4-carboxylate

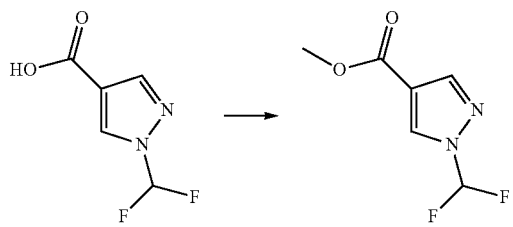

To a solution of 1-(difluoromethyl)-1H-pyrazole-4-carboxylic acid (100 mg, 0.62 mmol) in DCM (4 mL) was added (diazomethyl)trimethylsilane (0.62 mL, 1.23 mmol, 2 M in hexane). The mixture was stirred at room temperature for 2 hours. Acetic acid (0.2 mL) was added and the mixture was co-evaporated with toluene (2×20 mL) to give methyl 1-(difluoromethyl)-1H-pyrazole-4-carboxylate (99.0 mg, 0.56 mmol).

Preparation of (1-(difluoromethyl)-1H-pyrazol-4-yl)methanol

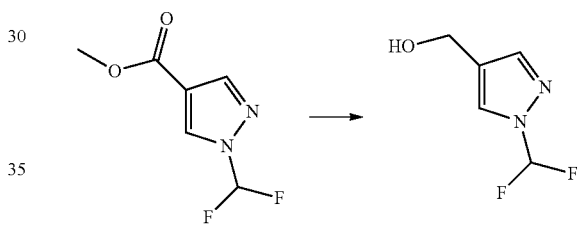

To a solution of methyl 1-(difluoromethyl)-1H-pyrazole-4-carboxylate (120 mg, 0.68 mmol) in THF (4 mL) at 0° C. was added lithium aluminum hydride (1.0 mL, 1.0 mmol, 1 M in THF). The mixture was stirred at 0° C. for 1 hour. A half saturated solution of sodium potassium tartarate (5 mL) was added and the mixture was stirred vigorously for 30 minutes. The mixture was then extracted with ethyl acetate (10 mL×3). The combined organic layers were washed with brine (10 mL), dried over Na$_2$SO$_4$ and concentrated. The crude mixture was purified by flash chromatography with heptane:ethyl acetate=1:0 to 0:1 to give (1-(difluoromethyl)-1H-pyrazol-4-yl)methanol (101 mg, 0.68 mmol).

Preparation of 4-(bromomethyl)-1-(difluoromethyl)-1H-pyrazole

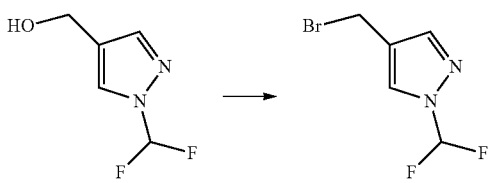 [SMILES: OCc1cnn(C(F)F)c1 ; FC(F)n1cc(CBr)cn1]

To a solution of (1-(difluoromethyl)-1H-pyrazol-4-yl)methanol (30 mg, 0.20 mmol) in MeCN (1.5 mL) was added triphenylphosphine (106 mg, 0.41 mmol), 2,6-lutidine (21.7 mg, 23.6 µl, 0.20 mmol) and CBr₄ (134 mg, 0.41 mmol). The reaction mixture was stirred at room temperature for 1 hour. The mixture is concentrated and purified directly by flash chromatography with heptane:ethyl acetate=1:0 to 0:1 to give 4-(bromomethyl)-1-(difluoromethyl)-1H-pyrazole (29 mg).

Preparation of N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine

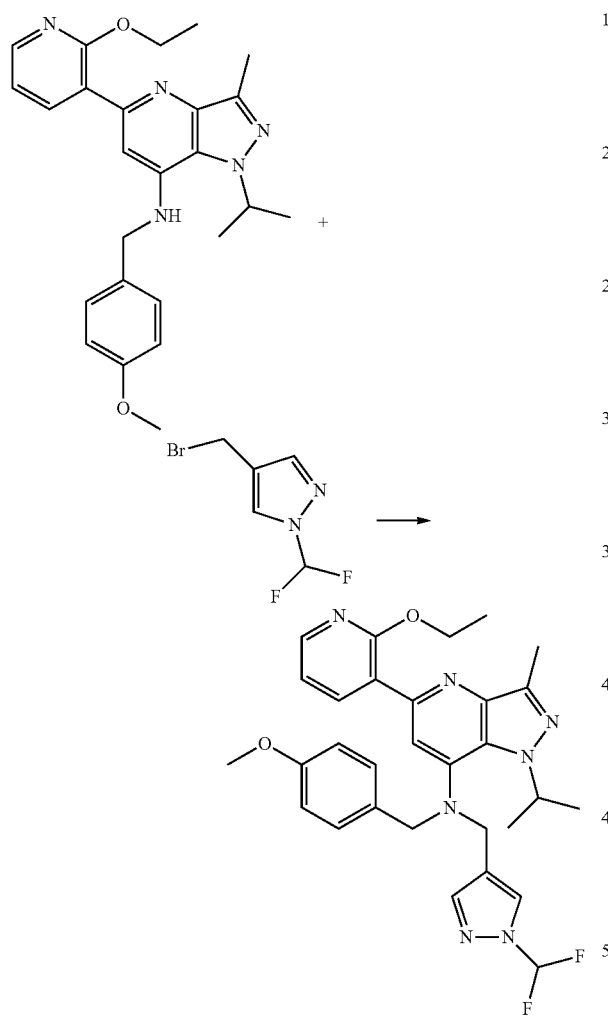

To a suspension of NaH (3.79 mg, 0.095 mmol, 60% w/w) in THF (1 mL) at 0° C. was added 5-(2-ethoxypyridin-3-yl)-1-isopropyl-N-(4-methoxybenzyl)-3-methyl-1H-pyrazolo[4,3-b]pyridin-7-amine (20.5 mg, 0.05 mmol). The mixture was stirred at 0° C. for 15 minutes before 4-(bromomethyl)-1-(difluoromethyl)-1H-pyrazole (10 mg, 0.05 mmol) in THF (1 mL) was added. The reaction mixture was slowly allowed to reach room temperature and stirred for 2 hours. Water (5 mL) was added and the mixture was extracted with ethyl acetate (5 mL×3). The combined organic layers were washed with brine (10 mL), dried over Na₂SO₄ and concentrated. The crude mixture was purified by flash chromatography with heptane:ethyl acetate=1:0 to 0:1 to give N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine (23 mg, 0.04 mmol).

Preparation of 3-bromo-2-ethoxypyridine

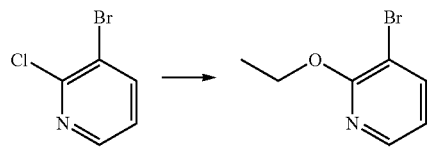

To a mixture of 3-bromo-2-chloropyridine (200 mg, 1 mmol) in EtOH (5 mL) was added t-BuOK (233 mg, 2 mmol). The mixture was stirred at 80° C. for 12 hours. The reaction mixture was filtered and the filtrate was concentrated in vacuo to give the crude product. The residue was purified by flash chromatography on silica gel (0%~40% ethyl acetate in petroleum ether) to afford 3-bromo-2-ethoxypyridine.

Preparation of 2-ethoxynicotinonitrile

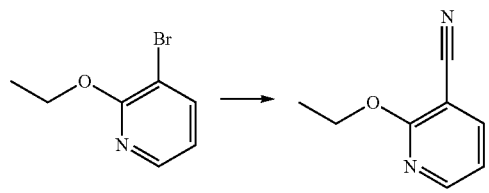

To a solution of 3-bromo-2-ethoxy-pyridine (350 mg, 1.7 mmol) in NMP (2 mL) was added Zn(CN)₂ (244 mg, 2.1 mmol) and Pd(dppf)Cl₂ (127 mg, 0.17 mmol). The mixture was degassed with N₂ and heated at 140° C. under microwave irradiation for 1 hour. The mixture was cooled to room temperature and filtered through celite. The filtered cake was washed with ethyl acetate (30 mL). The filtrate was washed with water (20 mL×2) and brine (20 mL), dried over Na₂SO₄, filtered and concentrated. The residue was purified by flash chromatography on silica gel (0%~20% ethyl acetate in petroleum ether) to give 2-ethoxynicotinonitrile.

Preparation of tert-butyl ((2-ethoxypyridin-3-yl)methyl)carbamate

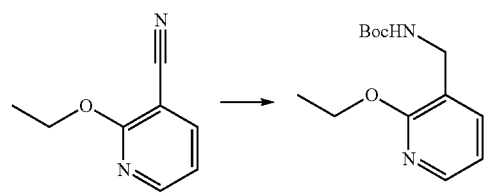 [SMILES: CCOc1ncccc1C#N ; CCOc1ncccc1CNC(=O)OC(C)(C)C]

To a solution of Raney-Ni (24 mg, 0.28 mmol) in EtOH (5 mL) was added 2-ethoxynicotinonitrile (210 mg, 1.4 mmol) and Boc₂O (371 mg, 1.7 mmol). The reaction mixture was stirred at room temperature under H₂ (45 psi) for 2 hours. The reaction mixture was filtered through celite and washed with EtOH (20 mL×2), then the filtrate was concentrated under reduced pressure to give a residue. The residue was purified by preperative HPLC to afford tert-butyl ((2-ethoxypyridin-3-yl)methyl)carbamate.

Preparation of (2-ethoxypyridin-3-yl)methanamine

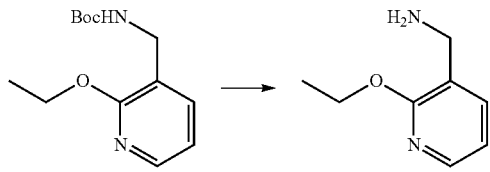 [SMILES: CCOc1ncccc1CNC(=O)OC(C)(C)C ; CCOc1ncccc1CN]

A solution of tert-butyl ((2-ethoxypyridin-3-yl)methyl) carbamate (85 mg, 0.34 mmol) in HCl/dioxane (4 M, 2 mL) was stirred at room temperature for 12 hours. The reaction mixture was concentrated under reduced pressure to afford 2-ethoxypyridin-3-yl)methanamine.

Preparation of 2'-ethoxy-6-methyl-[2,3'-bipyridin]-5-amine

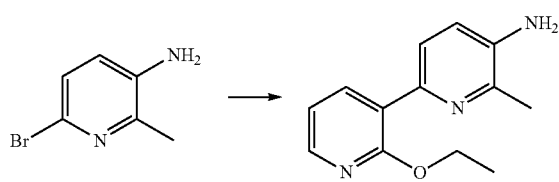

N₂ was bubbled through a mixture of 6-bromo-2-methyl-pyridin-3-amine (2.5 g, 13.4 mmol), 2-ethoxy-3-(4,4,5,5-tetramethyl-1,3,2-dioxaborolan-2-yl)pyridine (5.0 g, 20.1 mmol), PdCl₂(dppf)-CH₂Cl₂ (2.18 g, 2.67 mmol) and potassium carbonate (3.69 g, 26.7 mmol) in 1,4-dioxane (126 ml) and water (12 ml) for 10 minutes. A reflux condenser was inserted and the reaction mixture was heated at 105° C. for 2.5 hours under an inert atmosphere after which most of the solvent was removed under vacuo. The obtained residue was taken into ethyl acetate (150 ml) and filtered through a short pad of Celite which was rinsed with ethyl acetate (2×50 ml). Concentration and purification by flash chromatography on silica gel (elution with heptane to heptane/dichloromethane (1:1) to heptane/dichloromethane/ethyl acetate (1:1:1.5)) delivered 2'-ethoxy-6-methyl-[2,3'-bipyridin]-5-amine.

Preparation of 4-chloro-2'-ethoxy-6-methyl-[2,3'-bipyridin]-5-amine

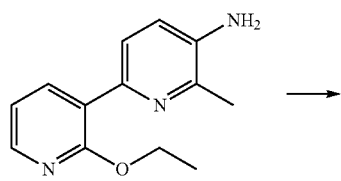

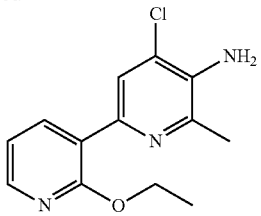

A solution of 2'-ethoxy-6-methyl-[2,3'-bipyridin]-5-amine (7.40 g, 22.6 mmol) and N-chloro succinimde (3.77 g, 28.2 mmol) in NMP (104 ml) was stirred at room temperature for 15 minutes under an inert atmosphere. A reflux condenser was inserted and the solution was heated to 80° C. for 3.5 hours after which it was allowed to reach room temperature and partitioned between ethyl acetate (300 ml) and aqueous saturated NaHCO₃ (3×200 ml). The combined aqueous layers were extracted with ethyl acetate (50 ml). The combined organic layers were further washed with brine (2×100 ml), dried (Na₂SO₄) and concentrated. The residue was purified by flash chromatography on silica gel (heptane/ethyl acetate) to give 4-chloro-2'-ethoxy-6-methyl-[2,3'-bipyridin]-5-amine.

Preparation of 7-chloro-5-(2-ethoxypyridin-3-yl)-1H-pyrazolo[4,3-b]pyridine

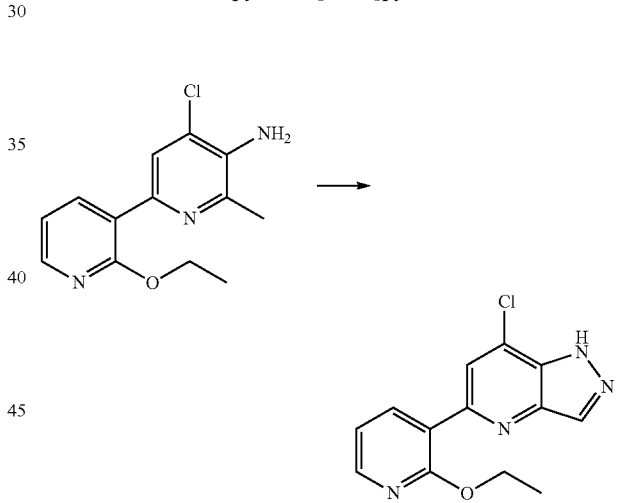

A suspension of 4-chloro-2'-ethoxy-6-methyl-[2,3'-bipyridin]-5-amine (4.01 g, 12.2 mmol) and potassium acetate (2.98 g, 30.4 mmol) in toluene (84 ml) and acetic acid (28 ml) was stirred at ice bath temperature for 5 minutes under an inert atmosphere. Isopentyl nitrite (2.71 g, 23.11 mmol) was added dropwise for 5 minutes. After stirring at ice bath temperature over 10 minutes a reflux condenser was inserted and the mixture was heated to 35° C. for 2.5 hours. Most of the solvent was removed under vacuo. The obtained residue was suspended in ethyl acetate (350 ml) and washed with aqueous saturated NaHCO₃ (2×250 ml), brine (200 ml), dried (Na₂SO₄) and concentrated. The residue was purified by flash chromatography on silica gel (heptane/ethyl acetate) to give 7-chloro-5-(2-ethoxypyridin-3-yl)-1H-pyrazolo[4,3-b]pyridine.

Preparation of 7-chloro-5-(2-ethoxypyridin-3-yl)-3-iodo-1H-pyrazolo[4,3-b]pyridine

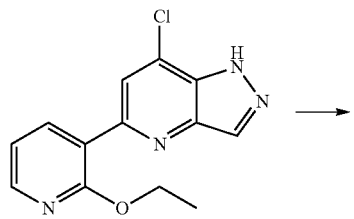

A solution of 7-chloro-5-(2-ethoxypyridin-3-yl)-1H-pyrazolo[4,3-b]pyridine (1.0 g, 3.64 mmol) and N-iodo succinimide (1.11 g, 4.91 mmol) in DMF (50.0 ml) was stirred at room temperature for 15 minutes under an inert atmosphere after which a reflux condenser was inserted and stirring continued at 35° C. for 11 hours. The solution was diluted with ethyl acetate (350 ml) and washed with aqueous 10% $Na_2S_2O_3$ (100 ml), aqueous ½ saturated $NaHCO_3$ (2×150 ml) and brine (50 ml). The organic layer was dried ($Na_2SO_4$) and concentrated to deliver 7-chloro-5-(2-ethoxypyridin-3-yl)-3-iodo-1H-pyrazolo[4,3-b]pyridine which was used without further purification.

Preparation of 7-chloro-5-(2-ethoxypyridin-3-yl)-3-iodo-1-isopropyl-1H-pyrazolo[4,3-b]pyridine

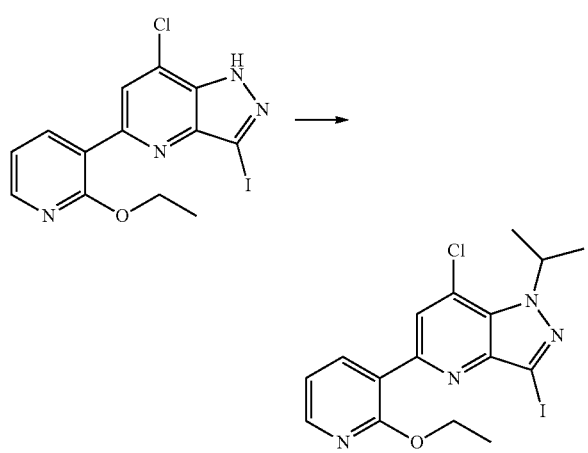

A solution of diisopropyl azodicarboxylate (1.59 g, 7.86 mmol) in THF (3.0 ml) was dropwise added to an ice cold solution of 7-chloro-5-(2-ethoxypyridin-3-yl)-3-iodo-1H-pyrazolo[4,3-b]pyridine (1.0 g, 2.25 mmol), isopropanol (0.60 ml, 7.86 mmol) and triphenylphosphine (2.06 g, 7.86 mmol) in THF (25 ml) under an inert atmosphere. After stirring at ice bath temperature for 0.5 hours, the solution was allowed to reach room temperature and stirring continued for 4.5 hours. Most of the solvent was removed under vacuo and the obtained residue was dissolved in ethyl acetate (150 ml) and washed with aqueous saturated $NaHCO_3$ (150 ml), brine (100 ml), dried ($Na_2SO_4$) and concentrated. Purification by flash chromatography on silica gel (elution gradient from heptane to ethyl acetate) delivered 7-chloro-5-(2-ethoxypyridin-3-yl)-3-iodo-1-isopropyl-1H-pyrazolo[4,3-b]pyridine.

Preparation of 7-chloro-5-(2-ethoxypyridin-3-yl)-1-isopropyl-3-vinyl-1H-pyrazolo[4,3-b]pyridine

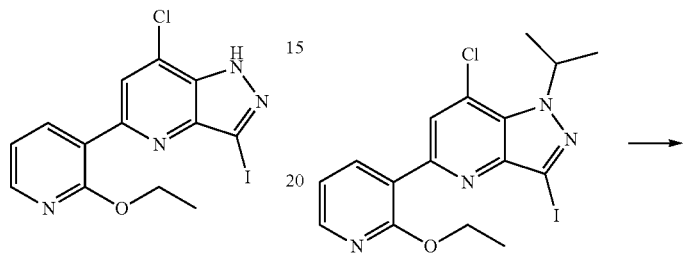

$N_2$ was bubbled through a suspension of 7-chloro-5-(2-ethoxypyridin-3-yl)-3-iodo-1-isopropyl-1H-pyrazolo[4,3-b]pyridine (10 mg, 0.023 mmol), tributyl(vinyl)stannane (9.9 µl, 0.034 mmol), bis(triphenylphosphine) palladiumI(II) dichloride (4 mg, 5.7 µmol) in 1,4-dioxane (0.30 ml) over 2 minutes. The mixture was stirred at 105° C. for 6.5 hours after which additional tributyl(vinyl)stannane (5.0 µl, 0.017 mmol), bis(triphenylphosphine) palladiumI(II) dichloride (1.6 mg, 2.3 µmop and 1,4-dioxane (0.15 ml) were added. The mixture was degassed by bubbling $N_2$ over 2 minutes and reheated to 105° C. for 5 hours. Most of the solvent was removed under vacuo. The obtained residue was dissolved in ethyl acetate (20 ml), washed with brine (10 ml) and dried ($Na_2SO_4$). Concentration under vacuo delivered a residue which was purified by flash chromatography on silica gel (elution gradient from heptane to ethyl acetate) to deliver 7-chloro-5-(2-ethoxypyridin-3-yl)-1-isopropyl-3-vinyl-1H-pyrazolo[4,3-b]pyridine.

Preparation of 1-(7-chloro-5-(2-ethoxypyridin-3-yl)-1-isopropyl-1H-pyrazolo[4,3-b]pyridin-3-yl)ethane-1,2-diol

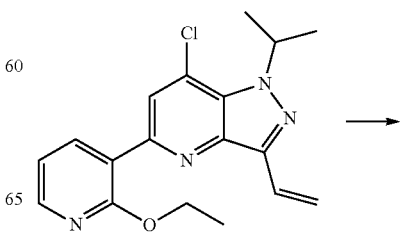

-continued

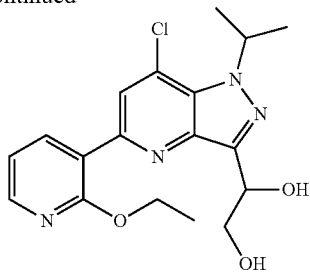

A mixture of 7-chloro-5-(2-ethoxypyridin-3-yl)-1-isopropyl-3-vinyl-1H-pyrazolo[4,3-b]pyridine (10 mg, 0.03 mmol), osmium tetraoxide (as a 2.5 wt % in 2-methyl-2-propanol) (37 µl, 2.9 µmol), N-methylmorpholine (as a 50% aqueous solution) (14 mg, 0.06 mmol) in THF (0.29 ml) and water (0.10 ml) was stirred at room temperature for 24 hours. The reaction was quenched at room temperature with aqueous 10% Na$_2$S$_2$O$_3$ (0.2 ml) and the resulting mixture was stirred for 5 minutes, diluted with brine (0.3 ml) and extracted with ethyl acetate (2×5 ml). The combined organic layers were dried (Na$_2$SO$_4$) and concentrated to deliver crude 1-(7-chloro-5-(2-ethoxypyridin-3-yl)-1-isopropyl-1H-pyrazolo[4,3-b]pyridin-3-yl)ethane-1,2-diol which was used without further purification.

Preparation of 7-chloro-5-(2-ethoxypyridin-3-yl)-1-isopropyl-1H-pyrazolo[4,3-b]pyridine-3-carbaldehyde

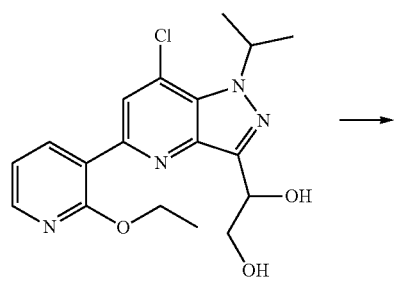

A mixture of 1-(7-chloro-5-(2-ethoxypyridin-3-yl)-1-isopropyl-1H-pyrazolo[4,3-b]pyridin-3-yl)ethane-1,2-diol (9.0 mg, 0.024 mmol) and sodium periodate (7.7 mg, 0.04 mmol) in THF (0.25 ml) and water (55 µl) was stirred at room temperature for 40 minutes after which sodium periodate (10.0 mg, 0.05 mmol) and 3 drops of water were added. After stirring for further 15 minutes, the resulting suspension was diluted with ethyl acetate (5 ml) and stirred for 3 minutes. The mixture was filtered through a short pad of Celite which was rinsed with ethyl acetate (2×5 ml). The combined filtrates were washed with brine (5 ml), dried (Na$_2$SO$_4$) and concentrated to deliver 7-chloro-5-(2-ethoxypyridin-3-yl)-1-isopropyl-1H-pyrazolo[4,3-b]pyridine-3-carbaldehyde which was used without further purification.

Preparation of (7-chloro-5-(2-ethoxypyridin-3-yl)-1-isopropyl-1H-pyrazolo[4,3-b]pyridin-3-yl)methanol

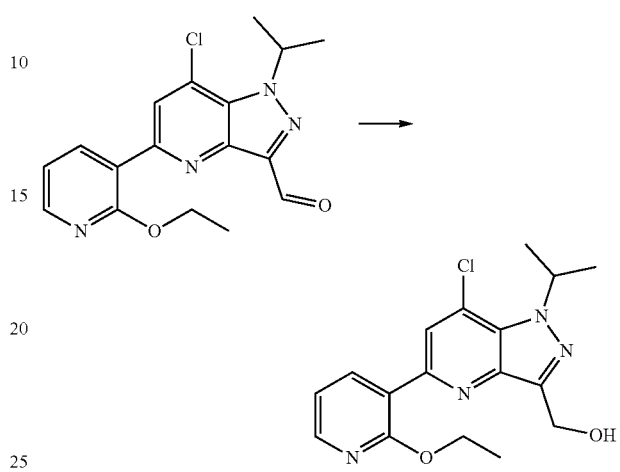

NaBH$_4$ (2.0 mg, 0.05 mmol) was added to an ice cold solution of 7-chloro-5-(2-ethoxypyridin-3-yl)-1-isopropyl-1H-pyrazolo[4,3-b]pyridine-3-carbaldehyde (4.0 mg, 0.01 mmol) in methanol (0.1 ml) under an inert atmosphere. After stirring for 5 minutes at ice bath temperature the resulting solution was allowed to reach room temperature and stirring continued for 1 hour Recooled to ice bath temperature and quenched with a few drops of water. Most of the solvent was removed under vacuo. The obtained residue was partitioned between ethyl acetate (15 ml) and brine (10 ml). The aqueous layer was back-extracted with ethyl acetate (5 ml). The combined organic layers were dried (Na$_2$SO$_4$) and concentrated. The residue was purified by flash chromatography on silica gel (heptane/ethyl acetate) to give (7-chloro-5-(2-ethoxypyridin-3-yl)-1-isopropyl-1H-pyrazolo[4,3-b]pyridin-3-yl)methanol.

Preparation of 7-chloro-5-(2-ethoxypyridin-3-yl)-3-(fluoromethyl)-1-isopropyl-1H-pyrazolo[4,3-b]pyridine

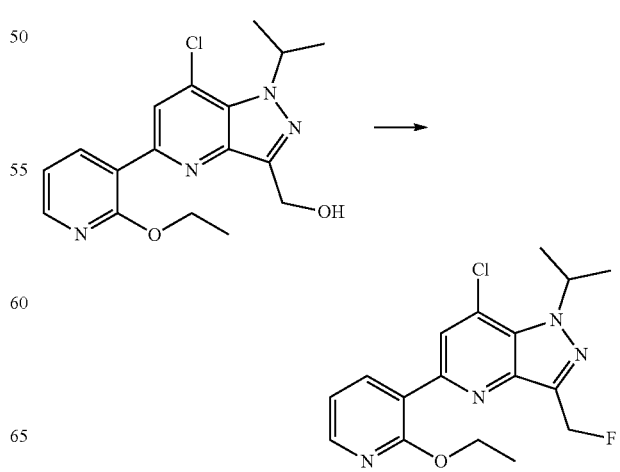

Diethylaminosulfur trifluoride (5 μl, 0.04 mmol) was added to an ice cold solution of (7-chloro-5-(2-ethoxypyridin-3-yl)-1-isopropyl-1H-pyrazolo[4,3-b]pyridin-3-yl)methanol (4.0 mg, 0.01 mmol) in CHCl$_3$ (0.2 ml). The reaction vial was capped and the solution was stirred at 0° C. for 5 minutes after which the cooling bath was removed and stirring continued at room temperature for 12 hours. The solution was diluted with ethyl acetate (25 ml) and washed with aqueous saturated NaHCO$_3$ (2×15 ml), brine (10 ml), dried (Na$_2$SO$_4$) and concentrated. The residue was purified by flash chromatography on silica gel (heptane/ethyl acetate) to give 7-chloro-5-(2-ethoxypyridin-3-yl)-3-(fluoromethyl)-1-isopropyl-1H-pyrazolo[4,3-b]pyridine.

Preparation of 7-chloro-3-(difluoromethyl)-5-(2-ethoxypyridin-3-yl)-1-isopropyl-1H-pyrazolo[4,3-b]pyridine

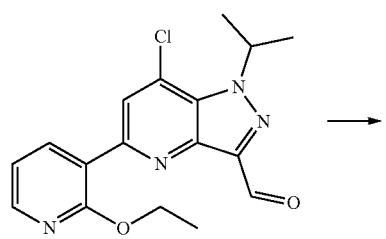

A solution of 7-chloro-5-(2-ethoxypyridin-3-yl)-1-isopropyl-1H-pyrazolo[4,3-b]pyridine-3-carbaldehyde (5.0 mg, 0.01 mmol) and diethylaminosulfur trifluoride (10 μl, 0.08 mmol) in dichloromethane (0.15 ml) was stirred at room temperature for 4.5 hours. under an inert atmosphere. The mixture was diluted with ethyl acetate (20 ml) and washed with aqueous saturated NaHCO$_3$ (10 ml) and brine (10 ml). The organic layer was dried (Na$_2$SO$_4$) and concentrated. The residue was purified by flash chromatography on silica gel (heptane/ethyl acetate) to give 7-chloro-3-(difluoromethyl)-5-(2-ethoxypyridin-3-yl)-1-isopropyl-1H-pyrazolo[4,3-b]pyridine.

Preparation of 5-((tert-butyldimethylsilyl)oxy)pentan-1-ol

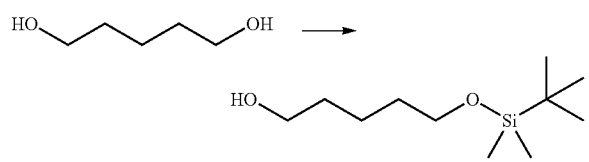

To a solution of pentane-1,5-diol (518 mg 4.98 mmol) in DCM (15 mL) was added imidazole (339 mg, 4.98 mmol) and tert-butylchlorodimethylsilane (500 mg, 3.32 mmol). The reaction mixture was stirred at room temperature for 16 hours. Water (10 mL) was added and the mixture was extracted with ethyl acetate (30 mL×3). The combined organic layers were washed with brine (20 mL), dried over Na$_2$SO$_4$ and concentrated. The crude mixture was purified by flash chromatography with heptane:ethyl acetate=1:0 to 0:1 to give 5-((tert-butyldimethylsilyl)oxy)pentan-1-ol.

The following intermediates was prepared in a similar manner:

Preparation of 2-(2-((tert-butyldimethylsilyl)oxy)ethoxy)ethan-1-ol

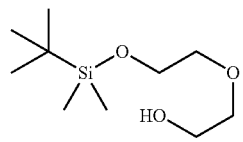

Prepared from 2,2'-oxybis(ethan-1-ol) and tert-butylchlorodimethylsilane.

Preparation of (4-bromobutoxy)(tert-butyl)dimethylsilane

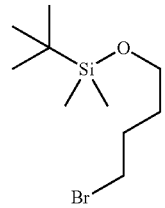

Prepared from 4-bromobutan-1-ol and tert-butylchlorodimethylsilane.

Preparation of 3-(bromomethyl)-2-fluoropyridine

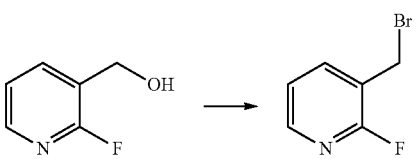 [SMILES: OCc1cccnc1F ; Fc1ncccc1CBr]

To a solution of (2-fluoropyridin-3-yl)methanol (500 mg 3.93 mmol) in DCM (15 mL) at 0° C. was added phosphorus tribromide (2.13 g, 7.87 mmol). The reaction mixture was stirred at room temperature for 16 hours. Water (10 mL) was added and the mixture was extracted with ethyl acetate (30 mL×3). The combined organic layers were washed with brine (20 mL), dried over Na$_2$SO$_4$ and concentrated to give 5-((tert-butyldimethylsilyl)oxy)pentan-1-ol.

Preparation of 1-(4-((tert-butyldimethylsilyl)oxy) butyl)-1H-pyrazole

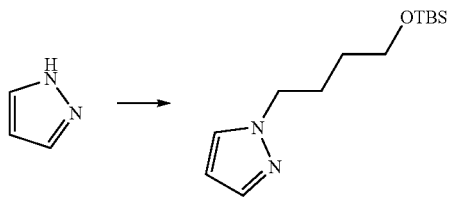 [SMILES: c1cn[nH]c1 ; CC(C)(C)[Si](C)(C)OCCCCn1cccn1]

To a solution of 1H-pyrazole (420 mg, 6.17 mmol) at 0° C. in DMF (16 mL) was added sodium hydride (412 mg, 10.3 mmol, 60% w/w) and (4-bromobutoxy)(tert-butyl)dimethylsilane (1.1 g, 4.12 mmol). The reaction mixture was stirred at room temperature for 16 hours. Water (10 mL) was added and the mixture was poured into a saturated, aqueous solution of $NH_4Cl$. The mixture was extracted with ethyl acetate (20 mL×3). The combined organic layers were washed with brine (20 mL), dried over $Na_2SO_4$ and concentrated. The crude mixture was purified by flash chromatography with heptane:ethyl acetate=1:0 to 0:1 to give 1-(4-((tert-butyldimethylsilyl)oxy)butyl)-1H-pyrazole.

Preparation of 1-(4-((tert-butyldimethylsilyl)oxy) butyl)-1H-pyrazole-5-carbaldehyde

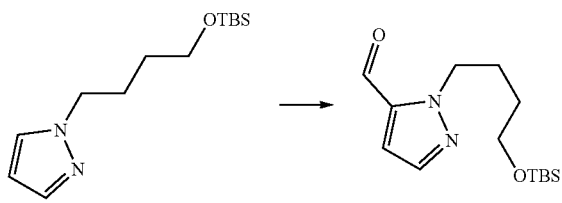 [SMILES: CC(C)(C)[Si](C)(C)OCCCCn1cccn1 ; CC(C)(C)[Si](C)(C)OCCCCn1nccc1C=O]

To a solution of 1-(4-((tert-butyldimethylsilyl)oxy)butyl)-1H-pyrazole (300 mg, 1.18 mmol) at −78° C. in THF (4.8 mL) was added n-butyllithium (873 μl, 2.36 mmol, 2.7 molar). The reaction mixture was stirred at −78° C. for 1 hour. DMF (215 mg, 2.95 mmol) was added and the reaction mixture was stirred at −78° C. for another hour. Water (10 mL) was added and the mixture was poured into a saturated, aqueous solution of $NH_4Cl$. The mixture was extracted with ethyl acetate (20 mL×3). The combined organic layers were washed with brine (20 mL), dried over $Na_2SO_4$ and concentrated. The crude mixture was purified by flash chromatography with heptane:ethyl acetate=1:0 to 0:1 to give 1-(4-((tert-butyldimethylsilyl)oxy)butyl)-1H-pyrazole-5-carbaldehyde.

Preparation of (1-(4-((tert-butyldimethylsilyl)oxy) butyl)-1H-pyrazol-5-yl)methanol

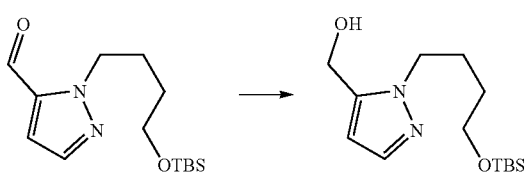 [SMILES: CC(C)(C)[Si](C)(C)OCCCCn1nccc1C=O ; CC(C)(C)[Si](C)(C)OCCCCn1nccc1CO]

To a solution of 1-(4-((tert-butyldimethylsilyl)oxy)butyl)-1H-pyrazole-5-carbaldehyde (310 mg, 1.10 mmol)) at 0° C. in ethanol (10 mL) was added sodium borohydride (83 mg, 2.20 mmol). The mixture was stirred at room temperature for 1 hour. The reaction mixture was concentrated and redissolved in 50 mL water. 5 mL 1N aqueous HCl was added. The mixture was extracted with ethyl acetate (20 mL×3). The combined organic layers were washed with brine (20 mL), dried over $Na_2SO_4$ and concentrated to give (1-(4-((tert-butyldimethylsilyl)oxy)butyl)-1H-pyrazol-5-yl) methanol.

Preparation of 1-(4-((tert-butyldimethylsilyl)oxy) butyl)-5-(chloromethyl)-1H-pyrazole

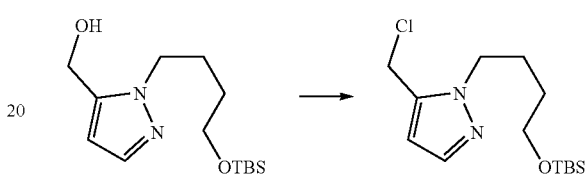

To a solution of (1-(4-((tert-butyldimethylsilyl)oxy)butyl)-1H-pyrazol-5-yl)methanol (130 mg, 0.46 mmol, in DCM (2.9 mL) was added triethylamine (231 mg, 2.29 mmol) and methanesulfonyl chloride (183 mg, 1.60 mmol). The reaction mixture was stirred at room temperature for 16 hours. Water (10 mL) was added and the mixture was extracted with ethyl acetate (30 mL×3). The combined organic layers were washed with brine (20 mL), dried over $Na_2SO_4$ and concentrated. The crude mixture was purified by flash chromatography with heptane:ethyl acetate=1:0 to 0:1 to give 1-(4-((tert-butyldimethylsilyl)oxy)butyl)-5-(chloromethyl)-1H-pyrazole.

The following intermediate was prepared in a similar manner:

1-(5-((tert-butyldimethylsilyl)oxy)pentyl)-5-(chloromethyl)-1H-pyrazole

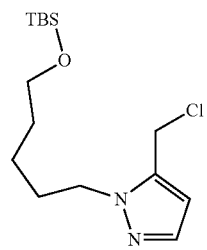

Prepared from ((5-bromopentyl)oxy)(tert-butyl)dimethylsilane and pyrazole

Preparation of 3-(4-((tert-butyldiphenylsilyl)oxy) butoxy)-2-methylpyrazine 1-oxide

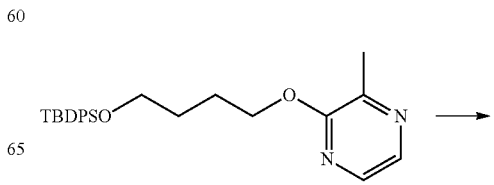

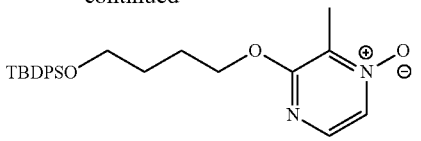

To a solution of 2-(4-((tert-butyldiphenylsilyl)oxy)butoxy)-3-methylpyrazine (470 mg, 1,117 mmol) in dichloromethane (7.2 mL) was added meta-chloroperoxybenzoic acid (289 mg, 1.68 mmol). The reaction mixture was stirred at 35° C. for 3 hours. The reaction mixture was poured into a saturated, aqueous solution of NaHCO$_3$. The mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give 3-(4-((tert-butyldiphenylsilyl)oxy)butoxy)-2-methylpyrazine 1-oxide.

Preparation of (3-(4-((tert-butyldiphenylsilyl)oxy) butoxy)pyrazin-2-yl)methyl acetate

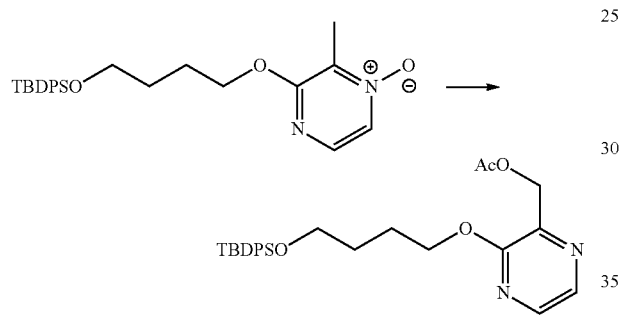

3-(4-((tert-butyldiphenylsilyl)oxy)butoxy)-2-methylpyrazine 1-oxide (200 mg, 0.46 mmol) was suspended in acetic anhydride (5 mL) and heated to 100° C. for 16 hours. The reaction mixture was poured into a saturated, aqueous solution of NaHCO$_3$. The mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give (3-(4-((tert-butyldiphenylsilyl)oxy)butoxy)pyrazin-2-yl) methyl acetate.

Preparation of (3-(4-((tert-butyldiphenylsilyl)oxy) butoxy)pyrazin-2-yl)methanol

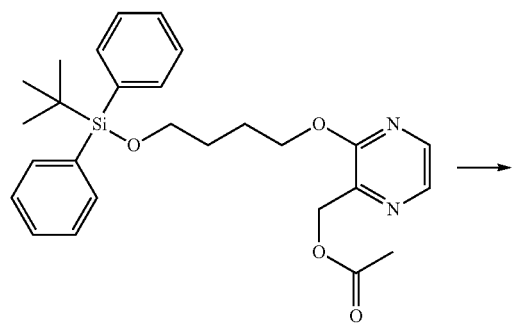

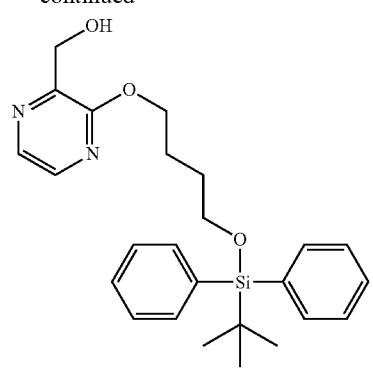

To a solution of (3-(4-((tert-butyldiphenylsilyl)oxy)butoxy)pyrazin-2-yl)methyl acetate (125 mg, 0.26 mmol) in MeOH (1 mL) was added sodium methoxide (3 μL, 0.013 mmol, 25% in MeOH). The reaction mixture was stirred at room temperature for 2 hours. Water (10 mL) was added and the mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give (3-(4-((tert-butyldiphenylsilyl) oxy)butoxy)pyrazin-2-yl)methanol.

Preparation of (3-(4-((tert-butyldimethylsilyl)oxy) butoxy)pyridin-2-yl)methanol

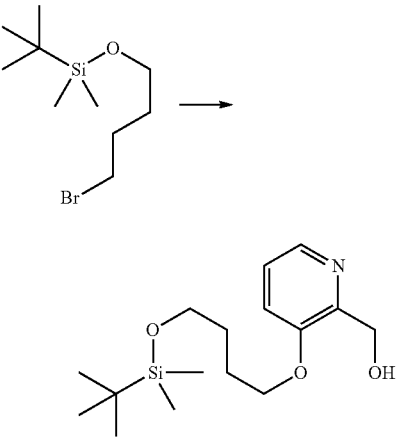

Potassium carbonate (103 mg, 0.748 mmol) was added to (4-bromobutoxy)(tert-butyl)dimethylsilane (200 mg, 0.748 mmol) and 2-(hydroxymethyl)pyridin-3-ol (94 mg, 0.748 mmol) in DMF (4 ml). The reaction mixture was stirred at 50° C. overnight. Water was added. The mixture was extracted with ethyl acetate. The organic phase was washed 3 times with brine/water 1/1, dried over MgSO$_4$ and concentrated in vacuo. The crude material was purified via flash chromatography on silica gel (ethyl acetate/heptane) to give 3-(4-((tert-butyldimethylsilyl)oxy)butoxy)pyridin-2-yl) methanol.

Preparation of 3-(4-((tert-butyldimethylsilyl)oxy)butoxy)-2-(chloromethyl)pyridine

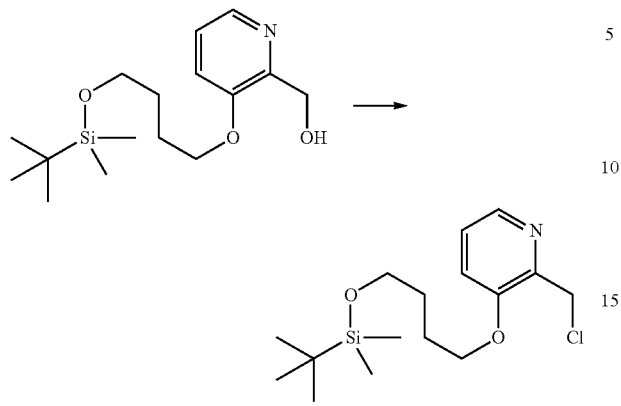

Triethylamine (60 μl, 0.430 mmol) was added to (3-(4-((tert-butyldimethylsilyl)oxy)butoxy)pyridin-2-yl)methanol (30 mg, 0.096 mmol) in dichloromethane (1 ml). Methanesulfonyl chloride (25 μl, 0.321 mmol) was added. The reaction mixture was stirred at room temperature overnight. The reaction mixture was poured into sat. NaHCO$_3$ (aq) and brine (1:1). The mixture was extracted with ethyl acetate. The organic phase was washed with brine, dried over MgSO$_4$ and concentrated in vacuo to give 3-(4-((tert-butyldimethylsilyl)oxy)butoxy)-2-(chloromethyl)pyridine. Used in the next step without further purification.

2-(4-((tert-butyldiphenylsilyl)oxy)butoxy)-3-(chloromethyl)pyrazine

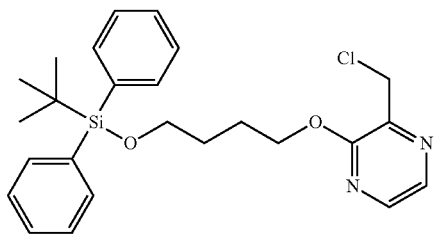 [SMILES: CC(C)(C)[Si](OCCCCOc1nccnc1CCl)(c1ccccc1)c1ccccc1]

Prepared in a similar way from (3-(4-((tert-butyldiphenylsilyl)oxy)butoxy)pyrazin-2-yl)methanol.

Preparation of 5-(2-(4-((tert-butyldimethylsilyl)oxy)butoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine

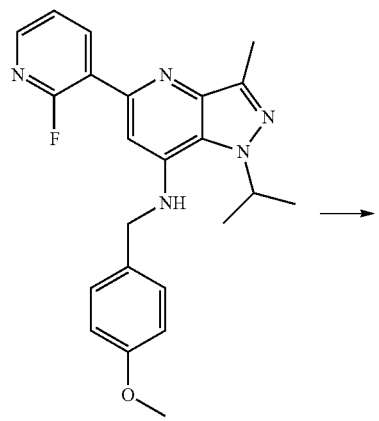

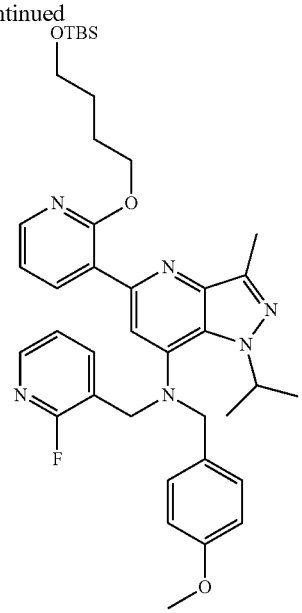

To a solution of 4-((tert-butyldimethylsilyl)oxy)butan-1-ol (176 mg, 0.86 mmol) in THF (5 mL) at 0° C. was added sodium hydride (49.3 mg, 1.23 mmol, 60% w/w). The mixture was stirred at 0° C. for 15 minutes before 5-(2-fluoropyridin-3-yl)-1-isopropyl-N-(4-methoxybenzyl)-3-methyl-1H-pyrazolo[4,3-b]pyridin-7-amine (100 mg, 0.25 mmol) was added. The reaction mixture was stirred at room temperature for 16 hours and then cooled to 0° C. Sodium hydride (19.7 mg, 0.49 mmol, 60% w/w) and 3-(bromomethyl)-2-fluoropyridine were added and the mixture was stirred at room temperature for 3 hours. Water (10 mL) was added and the mixture was extracted with ethyl acetate (30 mL×3). The combined organic layers were washed with brine (20 mL), dried over Na$_2$SO$_4$ and concentrated. The crude mixture was purified by flash chromatography with heptane:ethyl acetate=1:0 to 0:1 to give 5-(2-(4-((tert-butyldimethylsilyl)oxy)butoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine.

The following intermediates were prepared in a similar manner:

Preparation of 5-(2-(3-((tert-butyldimethylsilyl)oxy)propoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine

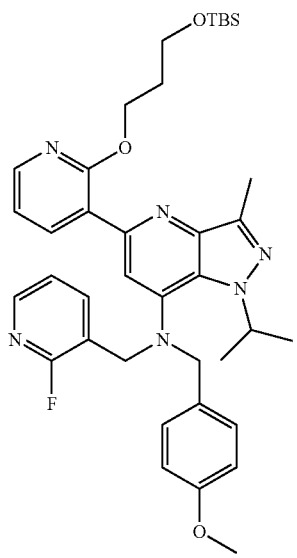 [SMILES: COc1ccc(CN(Cc2cccnc2F)c2cc(-c3cccnc3OCCCO[Si](C)(C)C(C)(C)C)nc3c(C)nn(C(C)C)c23)cc1]

Prepared from 5-(2-fluoropyridin-3-yl)-1-isopropyl-N-(4-methoxybenzyl)-3-methyl-1H-pyrazolo[4,3-b]pyridin-7-amine, 3-(bromomethyl)-2-fluoropyridine and 3-((tert-butyldimethylsilyl)oxy)propan-1-ol 5-(2-((5-((tert-butyldimethylsilyl)oxy)pentyl)oxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine

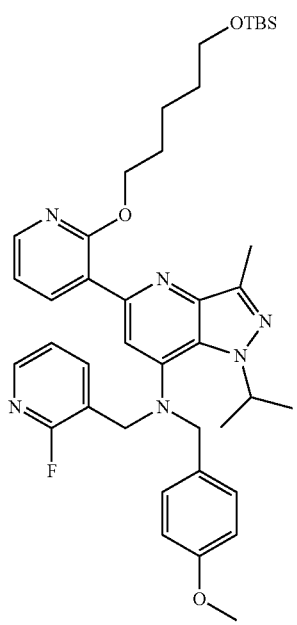 [SMILES: COc1ccc(CN(Cc2cccnc2F)c2cc(-c3cccnc3OCCCCCO[Si](C)(C)C(C)(C)C)nc3c(C)nn(C(C)C)c23)cc1]

Prepared from 5-(2-fluoropyridin-3-yl)-1-isopropyl-N-(4-methoxybenzyl)-3-methyl-1H-pyrazolo[4,3-b]pyridin-7-amine, 3-(bromomethyl)-2-fluoropyridine and 5-((tert-butyldimethylsilyl)oxy)pentan-1-ol 5-(2-(2-(2-((tert-butyldimethylsilyl)oxy)ethoxy)ethoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine

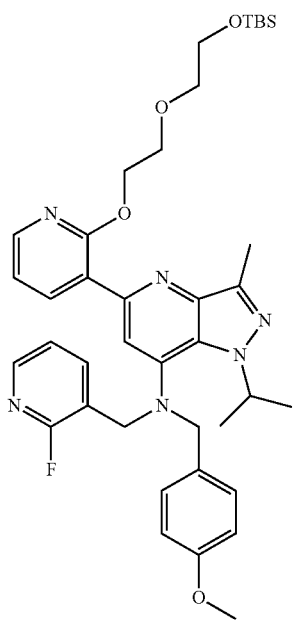 [SMILES: COc1ccc(CN(Cc2cccnc2F)c2cc(-c3cccnc3OCCOCCO[Si](C)(C)C(C)(C)C)nc3c(C)nn(C(C)C)c23)cc1]

Prepared from 5-(2-fluoropyridin-3-yl)-1-isopropyl-N-(4-methoxybenzyl)-3-methyl-1H-pyrazolo[4,3-b]pyridin-7-amine, 3-(bromomethyl)-2-fluoropyridine and 2-(2-((tert-butyldimethylsilyl)oxy)ethoxy)ethan-1-ol.

Preparation of N-((1-(4-(((tert-butyldimethylsilyl)oxy)butyl)-1H-pyrazol-5-yl)methyl)-5-(2-fluoropyridin-3-yl)-1-isopropyl-N-(4-methoxybenzyl)-3-methyl-1H-pyrazolo[4,3-b]pyridin-7-amine

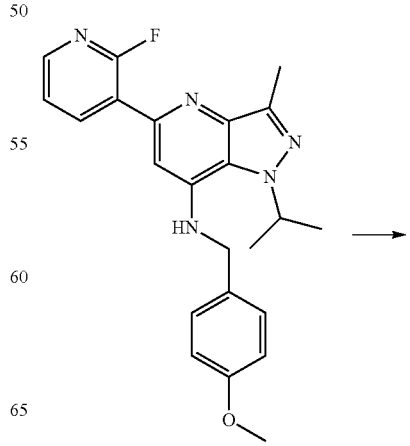

-continued

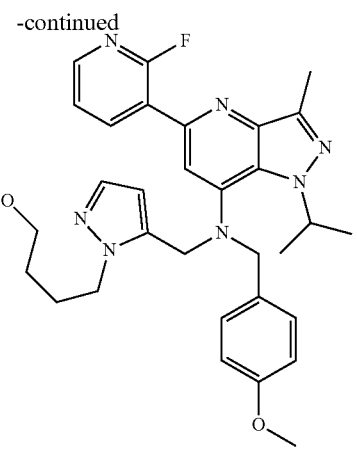

To a solution of 5-(2-fluoropyridin-3-yl)-1-isopropyl-N-(4-methoxybenzyl)-3-methyl-1H-pyrazolo[4,3-b]pyridin-7-amine (25 mg, 0.06 mmol) at 0° C. in THF (1 mL) was added sodium hydride (6.2 mg, 0.15 mmol, 60% w/w). The mixture was stirred at 0° C. for 15 minutes before 1-(4-((tert-butyldimethylsilyl)oxy)butyl)-5-(chloromethyl)-1H-pyrazole (37.4 mg, 0.12 mmol) and sodium iodide (4.62 mg, 0.03 mmol) were added. The reaction mixture was stirred at room temperature for 16 hours. Water (10 mL) was added and the mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give N-((1-(4-((tert-butyldimethylsilyl)oxy)butyl)-1H-pyrazol-5-yl)methyl)-5-(2-fluoropyridin-3-yl)-1-isopropyl-N-(4-methoxybenzyl)-3-methyl-1H-pyrazolo[4,3-b]pyridin-7-amine.

The following intermediates was prepared in a similar manner:

N-((1-(5-((tert-butyldimethylsilyl)oxy)pentyl)-1H-pyrazol-5-yl)methyl)-5-(2-fluoropyridin-3-yl)-1-isopropyl-N-(4-methoxybenzyl)-3-methyl-1H-pyrazolo[4,3-b]pyridin-7-amine

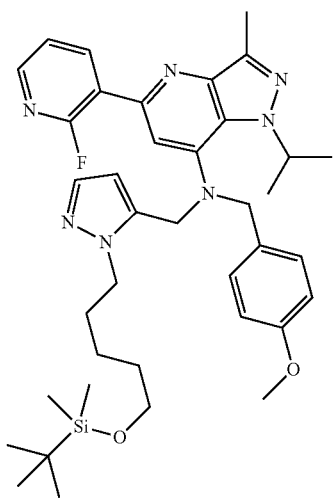 [SMILES: COc1ccc(CN(Cc2ccnn2CCCCCO[Si](C)(C)C(C)(C)C)c2cc(-c3cccnc3F)nc3c(C)nn(C(C)C)c23)cc1]

Prepared from 1-(5-((tert-butyldimethylsilyl)oxy)pentyl)-5-(chloromethyl)-1H-pyrazole and 5-(2-fluoropyridin-3-yl)-1-isopropyl-N-(4-methoxybenzyl)-3-methyl-1H-pyrazolo[4,3-b]pyridin-7-amine.

Preparation of N-((3-((4-((tert-butyldimethylsilyl)oxy)butyl)oxy)pyridin-2-yl)methyl)-5-(2-fluoropyridin-3-yl)-1-isopropyl-N-(4-methoxybenzyl)-3-methyl-1H-pyrazolo[4,3-b]pyridin-7-amine

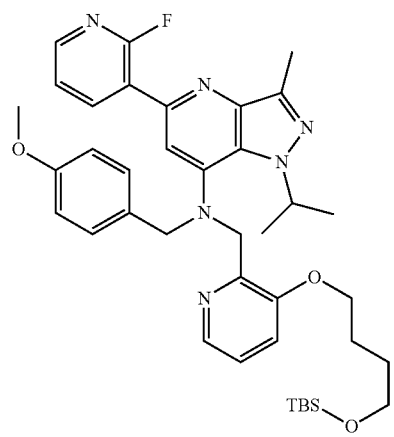

Prepared in a similar way from 3-(4-((tert-butyldimethylsilyl)oxy)butoxy)-2-(chloromethyl)pyridine and 5-(2-fluoropyridin-3-yl)-1-isopropyl-N-(4-methoxybenzyl)-3-methyl-1H-pyrazolo[4,3-b]pyridin-7-amine N-((3-(4-((tert-butyldiphenylsilyl)oxy)butoxy)pyrazin-2-yl)methyl)-5-(2-fluoropyridin-3-yl)-1-isopropyl-N-(4-methoxybenzyl)-3-methyl-1H-pyrazolo[4,3-b]pyridin-7-amine

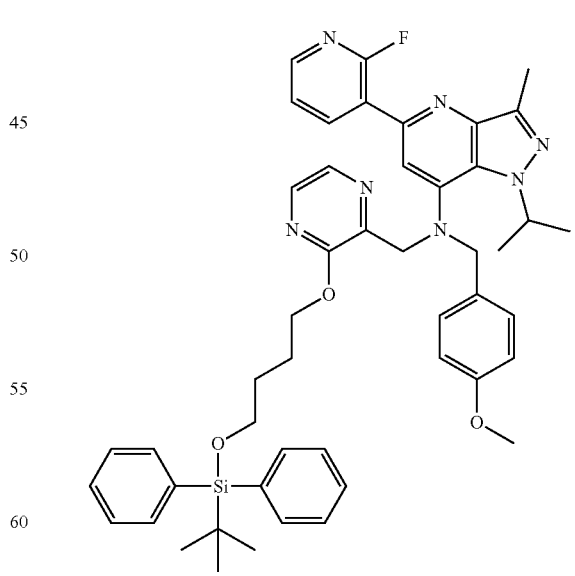

Prepared in a similar way from 2-(4-((tert-butyldiphenylsilyl)oxy)butoxy)-3-(chloromethyl)pyrazine and 5-(2-fluoropyridin-3-yl)-1-isopropyl-N-(4-methoxybenzyl)-3-methyl-1H-pyrazolo[4,3-b]pyridin-7-amine.

71

Preparation of 4-(5-(((5-(2-fluoropyridin-3-yl)-1-isopropyl-3-methyl-1H-pyrazolo[4,3-b]pyridin-7-yl)(4-methoxybenzyl)amino)methyl)-1H-pyrazol-1-yl)butan-1-ol

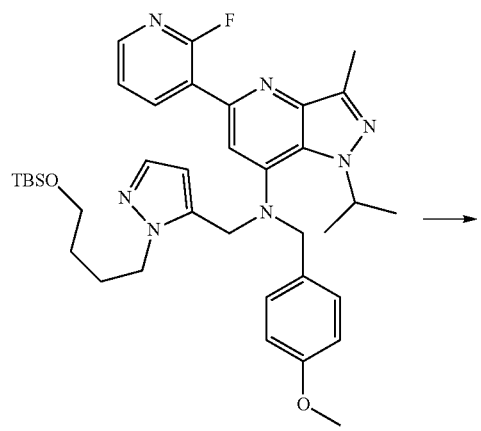

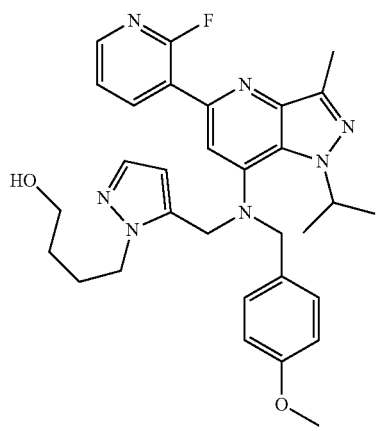

To a solution N-((1-(4-((tert-butyldimethylsilyl)oxy)butyl)-1H-pyrazol-5-yl)methyl)-5-(2-fluoropyridin-3-yl)-1-isopropyl-N-(4-methoxybenzyl)-3-methyl-1H-pyrazolo[4,3-b]pyridin-7-amine (35 mg, 0.05 mmol) in THF (1 mL) was added tetra-n-butylammonium fluoride (50.4 mg, 0.21 mmol). The mixture was stirred at room temperature for 16 hours. Water (10 mL) was added and the mixture was extracted with ethyl acetate (20 mL×3). The combined organic layers were washed with brine (20 mL), dried over Na$_2$SO$_4$ and concentrated. The crude mixture was purified by flash chromatography with heptane:ethyl acetate=1:0 to 0:1 to give 4-(5-(((5-(2-fluoropyridin-3-yl)-1-isopropyl-3-methyl-1H-pyrazolo[4,3-b]pyridin-7-yl)(4-methoxybenzyl)amino)methyl)-1H-pyrazol-1-yl)butan-1-ol.

The following intermediate was prepared in a similar manner:

72

4-((3-(((5-(2-fluoropyridin-3-yl)-1-isopropyl-3-methyl-1H-pyrazolo[4,3-b]pyridin-7-yl)(4-methoxybenzyl)amino)methyl)pyrazin-2-yl)oxy)butan-1-ol

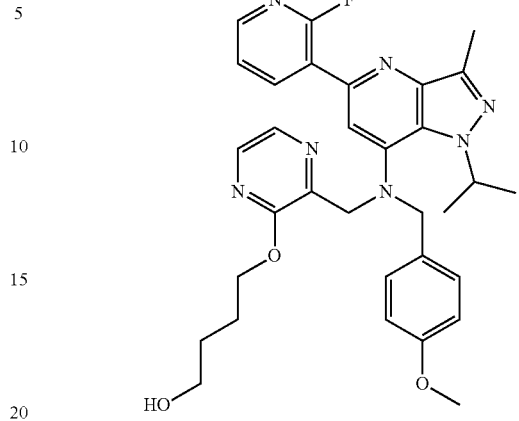

Prepared from N-((3-(4-(((tert-butyldiphenylsilyl)oxy)butoxy)pyrazin-2-yl)methyl)-5-(2-fluoropyridin-3-yl)-1-isopropyl-N-(4-methoxybenzyl)-3-methyl-1H-pyrazolo[4,3-b]pyridin-7-amine.

Preparation of 2$^1$-isopropyl-3-(4-methoxybenzyl)-2$^3$-methyl-2$^1$H,5$^1$H-10-oxa-3-aza-2(5,7)-pyrazolo[4,3-b]pyridina-1(3,2)-pyridina-5(5,1)-pyrazolacyclodecaphane

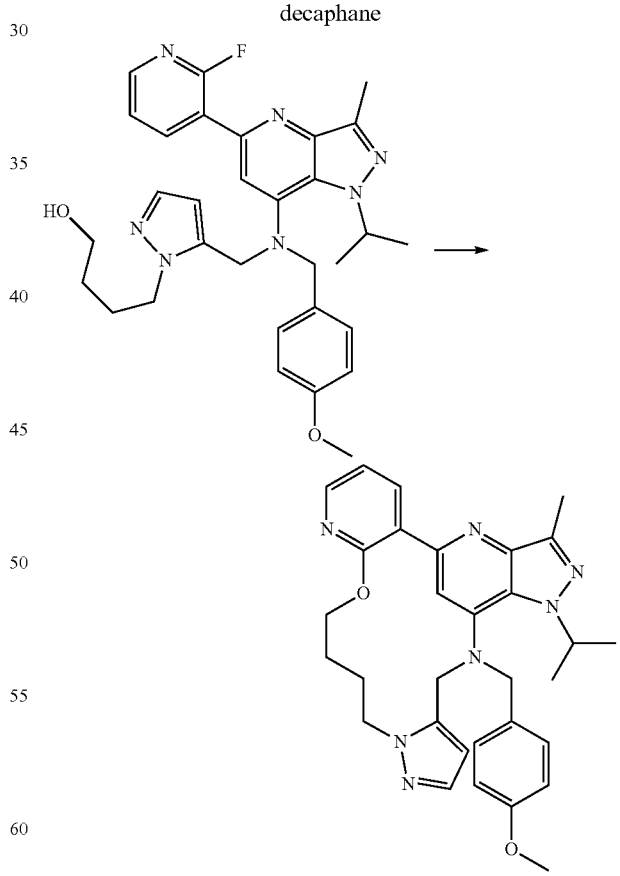

To a solution of 4-(5-(((5-(2-fluoropyridin-3-yl)-1-isopropyl-3-methyl-1H-pyrazolo[4,3-b]pyridin-7-yl)(4-methoxybenzyl)amino)methyl)-1H-pyrazol-1-yl)butan-1-ol (23 mg, 0.04 mmol) at 0° C. in THF (0.8 mL) was added sodium hydride (2.0 mg, 0.08 mmol, 60% w/w). The mixture was stirred at 60° C. for 16 hours. Water (10 mL) was added and the mixture was extracted with ethyl acetate (20 mL×3). The combined organic layers were washed with brine (20 mL), dried over Na₂SO₄ and concentrated. The crude mixture was purified by flash chromatography with heptane:ethyl acetate=1:0 to 0:1 to give 2¹-isopropyl-3-(4-methoxybenzyl)-2³-methyl-2¹H,5¹H-10-oxa-3-aza-2(5,7)-pyrazolo[4,3-b]pyridina-1(3,2)-pyridina-5(5,1)-pyrazolacyclodecaphane.

The following intermediate was prepared in a similar manner:

2¹-isopropyl-3-(4-methoxybenzyl)-2³-methyl-2¹H-6,11-dioxa-3-aza-2(5,7)-pyrazolo[4,3-b]pyridina-5(2,3)-pyrazina-1(3,2)-pyridinacycloundecaphane

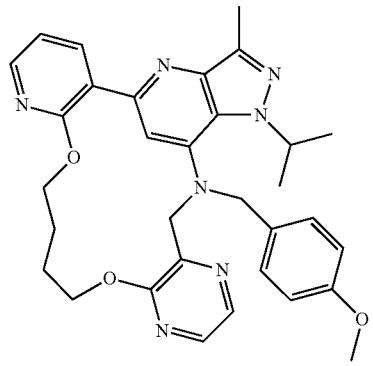 [SMILES: COc1ccc(CN2Cc3nccnc3OCCCCOc3ncccc3-c3cc2c2c(n3)c(C)nn2C(C)C)cc1]

Prepared from 4-((3-(((5-(2-fluoropyridin-3-yl)-1-isopropyl-3-methyl-1H-pyrazolo[4,3-b]pyridin-7-yl)(4-methoxybenzyl)amino)methyl)pyrazin-2-yl)oxy)butan-1-ol.

Preparation of 2¹-isopropyl-3-(4-methoxybenzyl)-2³-methyl-2¹H-6,11-dioxa-3-aza-2(5,7)-pyrazolo[4,3-b]pyridina-1,5(3,2)-dipyridinacycloundecaphane

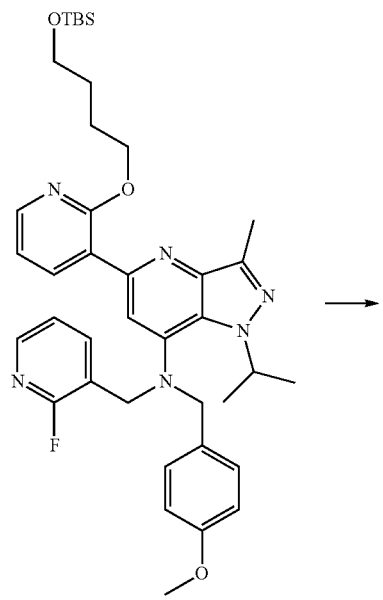

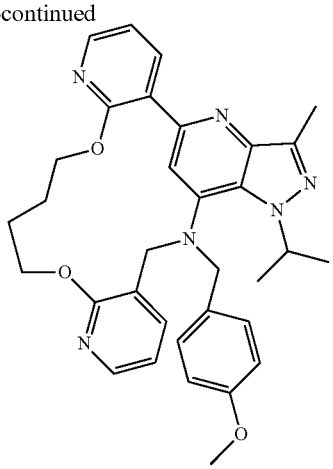

To a solution of 5-(2-(4-(((tert-butyldimethylsilyl)oxy)butoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine (128 mg, 0.18 mmol) in THF (3.8 mL) was added tetra-n-butylammonium fluoride (178 mg, 0.73 mmol). The mixture was stirred at room temperature for 3 hours before sodium hydride (36.6 mg, 0.92 mmol, 60% w/w) was added. The mixture was stirred at 60° C. for 3 hours. Water (10 mL) was added and the mixture was extracted with ethyl acetate (30 mL×3). The combined organic layers were washed with brine (20 mL), dried over Na₂SO₄ and concentrated. The crude mixture was purified by flash chromatography with heptane:ethyl acetate=1:0 to 0:1 to give 2¹-isopropyl-3-(4-methoxybenzyl)-2³-methyl-2¹H-6,11-dioxa-3-aza-2(5,7)-pyrazolo[4,3-b]pyridina-1,5(3,2)-dipyridinacycloundecaphane.

The following intermediates was prepared in a similar manner:

2¹-ethyl-3-(4-methoxybenzyl)-2³-methyl-2¹H-6,11-dioxa-3-aza-2(5,7)-pyrazolo[4,3-b]pyridina-1,5(3,2)-dipyridinacycloundecaphane

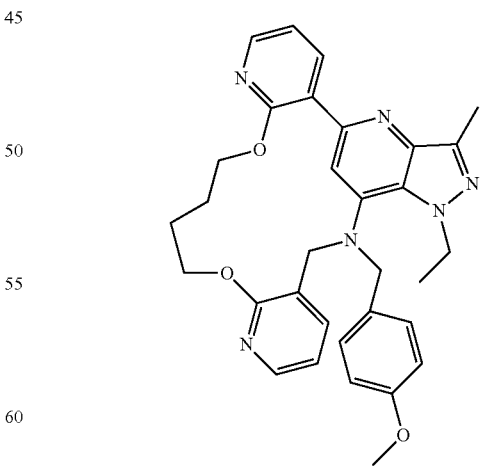

Prepared from 5,7-dibromo-1-ethyl-3-methyl-1H-pyrazolo[4,3-b]pyridine, (2-fluoropyridin-3-yl)boronic acid, 3-(chloromethyl)-2-fluoropyridine and 4-((tert-butyldimethylsilyl)oxy)butan-1-ol.

75

2¹-methyl-3-(4-methoxybenzyl)-2³-methyl-2¹H-6,
11-dioxa-3-aza-2(5,7)-pyrazolo[4,3-b]pyridina-1,5
(3,2)-dipyridinacycloundecaphane

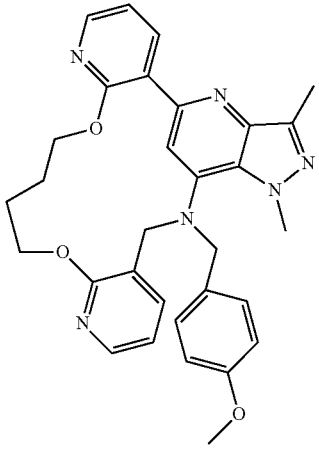 [SMILES: COc1ccc(CN2Cc3cccnc3OCCCCOc3ncccc3-c3cc2c2c(n3)c(C)nn2C)cc1]

Prepared from 5,7-dibromo-1,3-dimethyl-1H-pyrazolo[4,3-b]pyridine, (2-fluoropyridin-3-yl)boronic acid, 3-(chloromethyl)-2-fluoropyridine and 4-((tert-butyldimethylsilyl)oxy)butan-1-ol.

76

2¹-isopropyl-3-(4-methoxybenzyl)-2³-methyl-2¹H-6,
10-dioxa-3-aza-2(5,7)-pyrazolo[4,3-b]pyridina-1,5
(3,2)-dipyridinacyclodecaphane

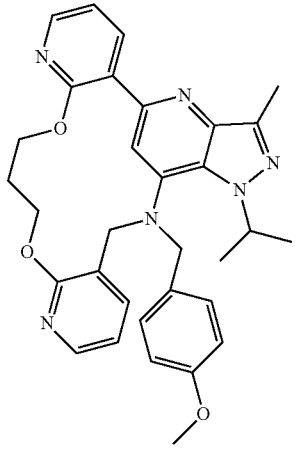

Prepared from 5-(2-(3-((tert-butyldimethylsilyl)oxy)propoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine 2¹-isopropyl-3-(4-methoxybenzyl)-2³-methyl-2¹H-6,
12-dioxa-3-aza-2(5,7)-pyrazolo[4,3-b]pyridina-1,5
(3,2)-dipyridinacyclododecaphane

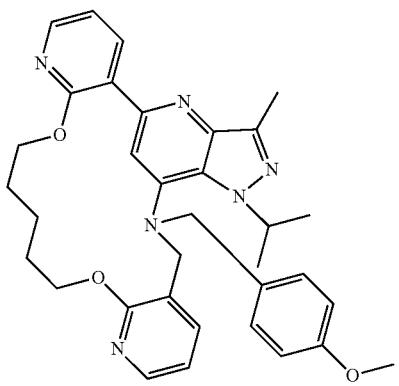 [SMILES: COc1ccc(CN2Cc3cccnc3OCCCCCOc3ncccc3-c3cc2c2c(n3)c(C)nn2C(C)C)cc1]

Prepared from 5-(2-((5-((tert-butyldimethylsilyl)oxy)pentyl)oxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine 2¹-isopropyl-3-(4-methoxybenzyl)-2³-methyl-2¹H-6,
9,12-trioxa-3-aza-2(5,7)-pyrazolo[4,3-b]pyridina-1,5
(3,2)-dipyridinacyclododecaphane

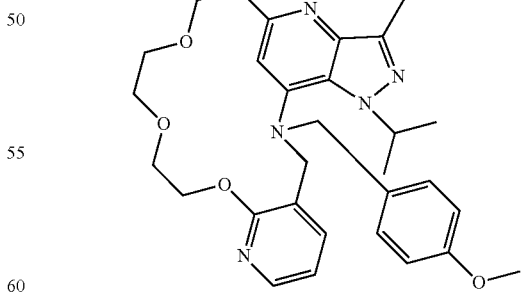

Prepared from 5-(2-(2-(2-((tert-butyldimethylsilyl)oxy)ethoxy)ethoxy)pyridin-3-yl)-N-((2-fluoropyridin-3-yl)methyl)-1-isopropyl-N-(4-methoxybenzyl)-3-methyl-1H-pyrazolo[4,3-b]pyridin-7-amine 2¹-isopropyl-3-(4-methoxybenzyl)-2³-methyl-2¹H,
5¹H-11-oxa-3-aza-2(5,7)-pyrazolo[4,3-b]pyridina-1
(3,2)-pyridina-5(5,1)-pyrazolacycloundecaphane

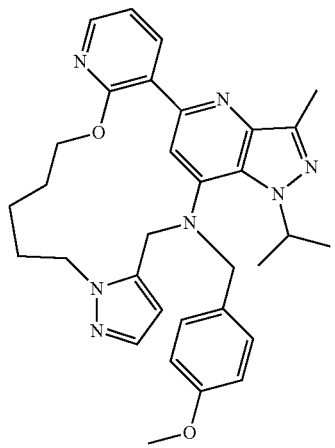 [SMILES: COc1ccc(CN2Cc3ccnn3CCCCCOc3ncccc3-c3cc2c2c(n3)c(C)nn2C(C)C)cc1]

Prepared from N-((1-(5-((tert-butyldimethylsilyl)oxy)
pentyl)-1H-pyrazol-5-yl)methyl)-5-(2-fluoropyridin-3-yl)-
1-isopropyl-N-(4-methoxybenzyl)-3-methyl-1H-pyrazolo
[4,3-b]pyridin-7-amine.

2¹-isopropyl-3-(4-methoxybenzyl)-2³-methyl-2¹H-6,
11-dioxa-3-aza-2(5,7)-pyrazolo[4,3-b]pyridina-1(3,
2),5(2,3)-dipyridinacycloundecaphane

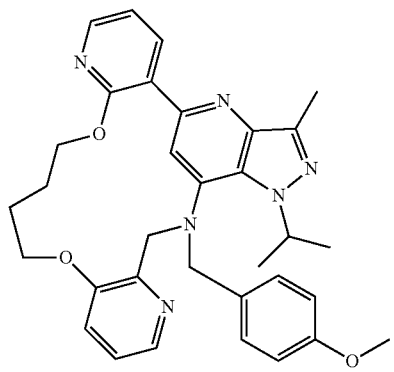 [SMILES: COc1ccc(CN2Cc3ncccc3OCCCCOc3ncccc3-c3cc2c2c(n3)c(C)nn2C(C)C)cc1]

Prepared from N-((3-((4-((tert-butyldimethylsilyl)oxy)
butyl)oxy)pyridin-2-yl)methyl)-5-(2-fluoropyridin-3-yl)-1-
isopropyl-N-(4-methoxybenzyl)-3-methyl-1H-pyrazolo[4,
3-b]pyridin-7-amine.

Compounds of the Invention

Example 1: 2¹-isopropyl-2³-methyl-2¹H-6,11-dioxa-
3-aza-2(5,7)-pyrazolo[4,3-b]pyridina-1,5(3,2)-
dipyridinacycloundecaphane

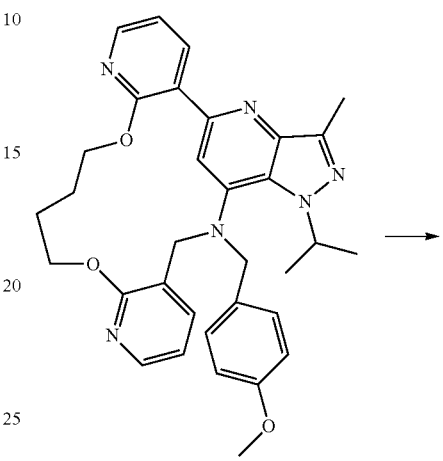

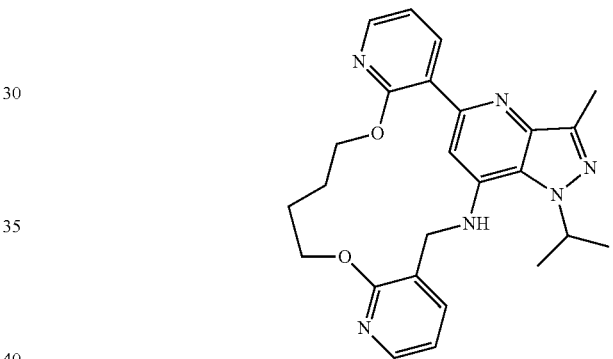

2¹-isopropyl-3-(4-methoxybenzyl)-2³-methyl-VH-6,11-
dioxa-3-aza-2(5,7)-pyrazolo[4,3-b]pyridina-1,5(3,2)-
dipyridinacycloundecaphane (17.0 mg, 0.03 mmol) was
suspended in trifluoroacetic acid (1.2 mL). The mixture was
stirred at 50° C. for 3 hours. Water (3 mL) was added and
the mixture was poured into a saturated, aqueous solution of
NaHCO₃. The mixture was extracted with ethyl acetate (20
mL×3). The combined organic layers were washed with
brine (20 mL), dried over Na₂SO₄ and concentrated. The
crude mixture was purified by flash chromatography with
heptane:ethyl acetate=1:0 to 0:1 to give 2¹-isopropyl-2³-
methyl-2¹H-6,11-dioxa-3-aza-2(5,7)-pyrazolo[4,3-b]
pyridina-1,5(3,2)-dipyridinacycloundecaphane. ¹H NMR
(600 MHz, Chloroform-d) δ 8.41 (dd, J=7.4, 2.0 Hz, 1H),
8.12 (dd, J=4.8, 2.0 Hz, 1H), 8.07 (dd, J=5.0, 1.9 Hz, 1H),
7.62 (dd, J=7.3, 1.9 Hz, 1H), 7.29 (s, 1H), 7.00 (dd, J=7.4,
4.9 Hz, 1H), 6.83 (dd, J=7.3, 5.0 Hz, 1H), 4.94 (t, J=5.7 Hz,
1H), 4.88 (hept, J=6.6 Hz, 1H), 4.68 (d, J=5.5 Hz, 2H),
4.58-4.47 (m, 4H), 2.62 (s, 3H), 2.25-2.14 (m, 2H), 2.00-
1.86 (m, 2H), 1.64 (d, J=6.6 Hz, 6H).

LC-MS: $t_R$=0.59 minutes (Method E), m/z=445.3
[M+H]⁺.

Example 2: 2¹-isopropyl-2³-methyl-2¹H-6,12-dioxa-3-aza-2(5,7)-pyrazolo[4,3-b]pyridina-1,5(3,2)-dipyridinacyclododecaphane

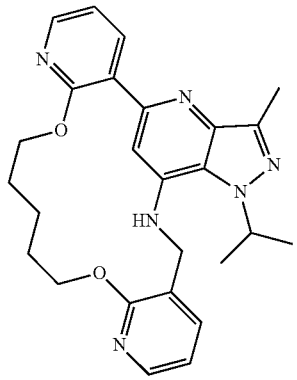 [SMILES: Cc1nn(C(C)C)c2c3cc(nc12)-c1cccnc1OCCCCCOc1ncccc1CN3]

Prepared in a way similar to example 1 from 2¹-isopropyl-3-(4-methoxybenzyl)-2³-methyl-2¹H-6,12-dioxa-3-aza-2(5,7)-pyrazolo[4,3-b]pyridina-1,5(3,2)-dipyridinacyclododecaphane.

¹H NMR (600 MHz, Chloroform-d) δ 8.20 (dd, J=7.4, 2.0 Hz, 1H), 8.13 (dd, J=4.9, 2.0 Hz, 1H), 8.09 (dd, J=5.0, 1.9 Hz, 1H), 7.57-7.50 (m, 1H), 6.98 (dd, J=7.4, 4.9 Hz, 1H), 6.96 (s, 1H), 6.83 (dd, J=7.3, 5.0 Hz, 1H), 4.91 (hept, J=6.6 Hz, 1H), 4.82 (t, J=5.7 Hz, 1H), 4.62 (d, J=5.6 Hz, 2H), 4.59-4.56 (m, 2H), 4.43 (t, J=5.3 Hz, 2H), 2.64 (s, 3H), 1.87-1.74 (m, 6H), 1.65 (d, J=6.5 Hz, 6H).

LC-MS: $t_R$=0.63 minutes (Method D), m/z=459.6 [M+H]⁺.

Example 3: 2¹-isopropyl-2³-methyl-2¹H-6,10-dioxa-3-aza-2(5,7)-pyrazolo[4,3-b]pyridina-1,5(3,2)-dipyridinacyclodecaphane

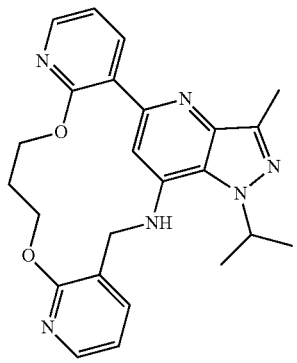 [SMILES: Cc1nn(C(C)C)c2c3cc(nc12)-c1cccnc1OCCCOc1ncccc1CN3]

Prepared in a way similar to example 1 from 2¹-isopropyl-3-(4-methoxybenzyl)-2³-methyl-2¹H-6,10-dioxa-3-aza-2(5,7)-pyrazolo[4,3-b]pyridina-1,5(3,2)-dipyridinacyclodecaphane. ¹H NMR (600 MHz, Chloroform-d) δ 8.59 (dd, J=7.5, 2.0 Hz, 1H), 8.14 (dd, J=4.8, 2.0 Hz, 1H), 8.05 (dd, J=4.9, 1.9 Hz, 1H), 7.69 (dd, J=7.3, 2.0 Hz, 1H), 7.66 (s, 1H), 7.01 (dd, J=7.5, 4.8 Hz, 1H), 6.85 (dd, J=7.4, 4.9 Hz, 1H), 5.23-5.15 (m, 1H), 4.92 (hept, J=6.6 Hz, 1H), 4.76-4.71 (m, 4H), 4.65 (d, J=5.8 Hz, 2H), 2.61 (s, 3H), 2.42-2.35 (m, 2H), 1.64 (d, J=6.5 Hz, 6H). LC-MS: $t_R$=0.59 minutes (Method D), m/z=431.6 [M+H]⁺.

Example 4: 2¹-isopropyl-2³-methyl-2¹H-6,9,12-trioxa-3-aza-2(5,7)-pyrazolo[4,3-b]pyridina-1,5(3,2)-dipyridinacyclododecaphane

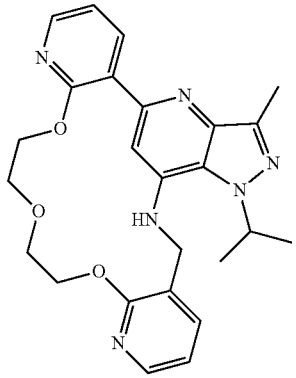 [SMILES: Cc1nn(C(C)C)c2c3cc(nc12)-c1cccnc1OCCOCCOc1ncccc1CN3]

Prepared in a way similar to example 1 from 2¹-isopropyl-3-(4-methoxybenzyl)-2³-methyl-2¹H-6,9,12-trioxa-3-aza-2(5,7)-pyrazolo[4,3-b]pyridina-1,5(3,2)-dipyridinacyclododecaphane.

¹H NMR (600 MHz, Chloroform-d) δ 8.27 (ddd, J=7.4, 2.0, 0.7 Hz, 1H), 8.09 (dd, J=4.8, 2.0 Hz, 1H), 8.04 (dd, J=5.0, 1.8 Hz, 1H), 7.49 (dd, J=7.3, 1.8 Hz, 1H), 7.06 (d, J=0.9 Hz, 1H), 6.99 (dd, J=7.4, 4.9 Hz, 1H), 6.80 (dd, J=7.3, 5.0 Hz, 1H), 5.02-4.93 (m, 2H), 4.74-4.70 (m, 2H), 4.68 (d, J=5.8 Hz, 2H), 4.60-4.55 (m, 2H), 3.88-3.83 (m, 2H), 3.82-3.78 (m, 2H), 2.64 (s, 3H), 1.68 (d, J=6.6 Hz, 6H).

LC-MS: $t_R$=0.5 minutes (Method D), m/z=461.6 [M+H]⁺.

Example 5: 2¹-isopropyl-2³-methyl-2¹H,5¹H-11-oxa-3-aza-2(5,7)-pyrazolo[4,3-b]pyridina-1(3,2)-pyridina-5(5,1)-pyrazolacycloundecaphane

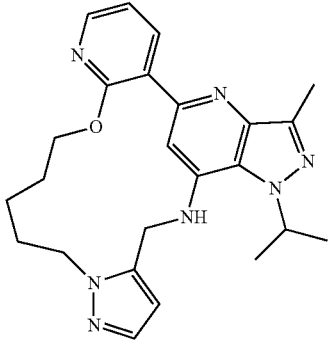 [SMILES: Cc1nn(C(C)C)c2c3cc(nc12)-c1cccnc1OCCCCCn1nccc1CN3]

Prepared in a way similar to example 1 from 2¹-isopropyl-3-(4-methoxybenzyl)-2³-methyl-2¹H,5¹H-10-oxa-3-aza-2(5,7)-pyrazolo[4,3-b]pyridina-1(3,2)-pyridina-5(5,1)-pyrazolacyclodecaphane. ¹H NMR (600 MHz, DMSO-$d_6$) δ 8.40-8.28 (m, 1H), 8.28-8.16 (m, 1H), 7.28 (d, J=1.8 Hz, 1H), 7.14 (dd, J=7.6, 4.8 Hz, 1H), 7.01 (s, 1H), 5.95 (s, 1H), 5.30 (hept, J=6.3 Hz, 1H), 4.83-4.72 (m, 2H), 4.53-4.43 (m, 2H), 4.24-4.16 (m, 2H), 2.53 (s, 3H), 2.03-1.96 (m, 2H), 1.74-1.65 (m, 2H), 1.51 (d, J=6.4 Hz, 6H), 1.33 (p, J=7.3 Hz, 2H).

LC-MS: $t_R$=0.5 minutes (Method D), m/z=432.6 [M+H]⁺.

Example 6: 2¹-isopropyl-2³-methyl-2¹H-6,11-dioxa-3-aza-2(5,7)-pyrazolo[4,3-b]pyridina-1(3,2),5(2,3)-dipyridinacycloundecaphane

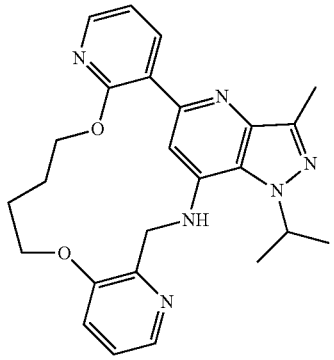 [SMILES: Cc1nn(C(C)C)c2c3cc(nc12)-c1cccnc1OCCCCOc1cccnc1CN3]

Prepared in a way similar to example 1 from 2¹-isopropyl-3-(4-methoxybenzyl)-2³-methyl-2¹H-6,11-dioxa-3-aza-2(5,7)-pyrazolo[4,3-b]pyridina-1(3,2),5(2,3)-dipyridinacycloundecaphane. $^1$H NMR (600 MHz, DMSO-$d_6$) δ 8.44-8.34 (m, 1H), 8.19-8.13 (m, 1H), 8.01 (dd, J=4.6, 1.2 Hz, 1H), 7.44 (dd, J=8.4, 1.3 Hz, 1H), 7.16 (dd, J=8.3, 4.6 Hz, 1H), 7.13 (s, 1H), 7.08 (dd, J=7.5, 4.8 Hz, 1H), 5.29 (hept, J=6.4 Hz, 1H), 4.73 (d, J=6.2 Hz, 2H), 4.54-4.48 (m, 2H), 4.20 (dd, J=6.0, 4.4 Hz, 2H), 2.46 (s, 3H), 2.22-2.14 (m, 2H), 1.94-1.87 (m, 2H), 1.47 (d, J=6.4 Hz, 6H).

LC-MS: $t_R$=0.51 minutes (Method D), m/z=445.6 [M+H]⁺.

Example 7: 2¹,2³-dimethyl-2¹H-6,11-dioxa-3-aza-2(5,7)-pyrazolo[4,3-b]pyridina-1,5(3,2)-dipyridinacycloundecaphane

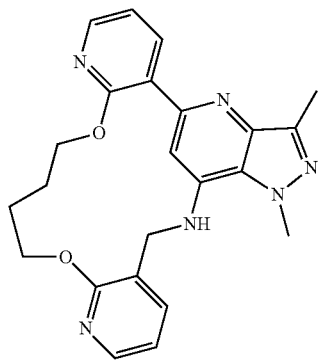 [SMILES: Cc1nn(C)c2c3cc(nc12)-c1cccnc1OCCCCOc1ncccc1CN3]

Prepared in a way similar to example 1 from 2¹-methyl-3-(4-methoxybenzyl)-2³-methyl-2¹H-6,11-dioxa-3-aza-2(5,7)-pyrazolo[4,3-b]pyridina-1,5(3,2)-dipyridinacycloundecaphane. $^1$H NMR (400 MHz, Chloroform-d) δ 8.41 (dd, J=2.0, 7.6 Hz, 1H), 8.14 (dd, J=2.0, 4.8 Hz, 1H), 8.09 (dd, J=1.6, 4.8 Hz, 1H), 7.63 (dd, J=1.6, 7.2 Hz, 1H), 7.34 (s, 1H), 7.01 (dd, J=4.8, 7.6 Hz, 1H), 6.85 (dd, J=4.8, 7.2 Hz, 1H), 4.98 (br s, 1H), 4.66 (d, J=5.6 Hz, 2H), 4.55-4.45 (m, 4H), 4.30 (s, 3H), 2.60 (s, 3H), 2.25-2.12 (m, 2H), 1.99-1.88 (m, 2H).

LC-MS: $t_R$=1.46 minutes (Method L), m/z=417.1 [M+H]⁺.

Example 8: 2¹-ethyl-2³-methyl-2¹H-6,11-dioxa-3-aza-2(5,7)-pyrazolo[4,3-b]pyridina-1,5(3,2)-dipyridinacycloundecaphane

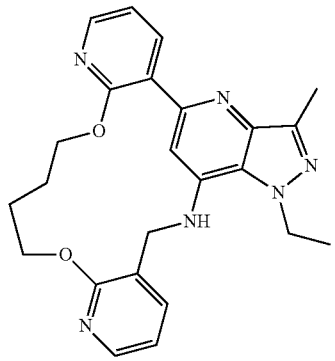 [SMILES: CCn1nc(C)c2nc3cc(c21)NCc1cccnc1OCCCCOc1ncccc1-3]

Prepared in a way similar to example 1 from 2¹-ethyl-3-(4-methoxybenzyl)-2³-methyl-2¹H-6,11-dioxa-3-aza-2(5,7)-pyrazolo[4,3-b]pyridina-1,5(3,2)-dipyridinacycloundecaphane. $^1$H NMR (400 MHz, Chloroform-d) δ 8.38 (dd, J=2.0, 7.6 Hz, 1H), 8.10 (dd, J=2.0, 4.8 Hz, 1H), 8.04 (dd, J=1.6, 5.2 Hz, 1H), 7.59 (dd, J=1.6, 7.2 Hz, 1H), 7.23 (s, 1H), 6.97 (dd, J=4.8, 7.6 Hz, 1H), 6.80 (dd, 1=5.2, 7.2 Hz, 1H), 4.89 (br s, 1H), 4.65 (br d, J=5.6 Hz, 2H), 4.58-4.42 (m, 6H), 2.58 (s, 3H), 2.24-2.11 (m, 2H), 1.94-1.84 (m, 2H), 1.47 (t, J=7.2 Hz, 3H). LC-MS: $t_R$=1.92 minutes (Method L), m/z=431.1 [M+H]⁺.

Example 9: 2¹-isopropyl-2³-methyl-2¹H,5¹H-10-oxa-3-aza-2(5,7)-pyrazolo[4,3-b]pyridina-1(3,2)-pyridina-5(5,1)-pyrazolacyclodecaphane

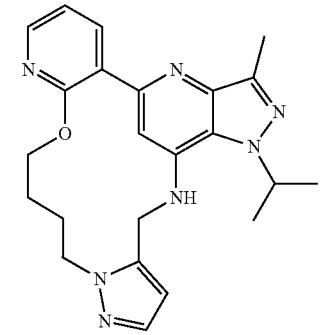 [SMILES: Cc1nn(C(C)C)c2c3cc(nc12)-c1cccnc1OCCCCn1nccc1CN3]

Prepared in a way similar to example 1 from 2¹-isopropyl-3-(4-methoxybenzyl)-2³-methyl-2¹H,5¹H-10-oxa-3-aza-2(5,7)-pyrazolo[4,3-b]pyridina-1(3,2)-pyridina-5(5,1)-pyrazolacyclodecaphane. $^1$H NMR (600 MHz, Chloroform-d) δ 8.65 (dd, J=7.5, 2.0 Hz, 1H), 8.13 (dd, J=4.8, 2.0 Hz, 1H), 7.52 (s, 1H), 7.38 (d, J=1.9 Hz, 1H), 7.03 (dd, J=7.5, 4.8 Hz, 1H), 6.21 (d, J=2.0 Hz, 1H), 4.99 (t, J=6.2 Hz, 1H), 4.88 (hept, J=6.5 Hz, 1H), 4.75 (d, J=6.2 Hz, 2H), 4.47-4.28 (m, 4H), 2.65 (s, 3H), 2.27 (p, J=7.1 Hz, 2H), 1.74 (td, J=10.9, 6.4 Hz, 2H), 1.66 (d, J=6.5 Hz, 6H).

LC-MS: $t_R$=0.48 minutes (Method D), m/z=418.6 [M+H]⁺.

Example 10: 2¹-isopropyl-2³-methyl-2¹H-6,11-dioxa-3-aza-2(5,7)-pyrazolo[4,3-b]pyridina-5(2,3)-pyrazina-1(3,2)-pyridinacycloundecaphane

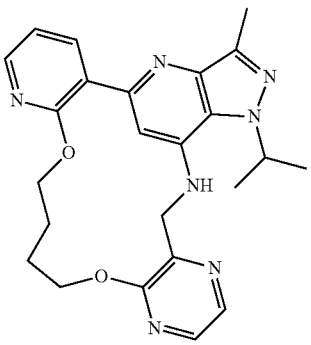 [SMILES: Cc1nn(C(C)C)c2c3cc(nc12)-c1cccnc1OCCCCOc1nccnc1CN3]

Prepared in a way similar to example 1 from 2¹-isopropyl-3-(4-methoxybenzyl)-2³-methyl-2¹H-6,11-dioxa-3-aza-2(5,7)-pyrazolo[4,3-b]pyridina-5(2,3)-pyrazina-1(3,2)-pyridinacycloundecaphane ¹H NMR (600 MHz, Chloroform-d) δ 8.51 (dd, J=7.5, 2.0 Hz, 1H), 8.14 (dd, J=4.8, 2.0 Hz, 1H), 8.03 (d, J=2.7 Hz, 1H), 7.98 (d, J=2.6 Hz, 1H), 7.47 (s, 1H), 7.02 (dd, J=7.4, 4.8 Hz, 1H), 5.29 (t, J=7.6 Hz, 1H), 4.99-4.89 (m, 1H), 4.80 (d, J=6.8 Hz, 2H), 4.59-4.54 (m, 2H), 4.51 (t, J=5.3 Hz, 2H), 2.61 (s, 3H), 2.24 (ddd, J=12.1, 8.5, 5.9 Hz, 2H), 2.03-1.97 (m, 2H), 1.63 (d, J=6.5 Hz, 6H).

LC-MS: $t_R$=0.56 minutes (Method D), m/z=446.3 [M+H]⁺.

SUPPORTING EXAMPLES

Supporting Example S1: 5-(2-ethoxypyridin-3-yl)-1-isopropyl-3-methyl-N-((5-methyl-1,3,4-oxadiazol-2-yl)methyl)-1H-pyrazolo[4,3-b]pyridin-7-amine

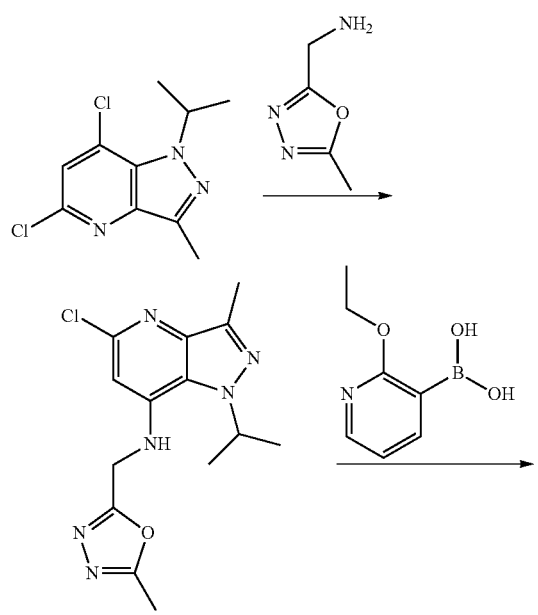

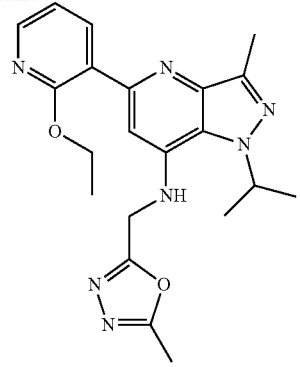

To a solution of 5,7-dichloro-1-isopropyl-3-methyl-1H-pyrazolo[4,3-b]pyridine (100 mg, 0.41 mmol) in NMP (2 mL) was added CsF (187 mg, 1.23 mmol, 45 μL) and (5-methyl-1,3,4-oxadiazol-2-yl)methanamine hydrochloride (74 mg, 0.49 mmol). The mixture was stirred at 100° C. for 18 hours. Water (30 mL) was added and the mixture was extracted with ethyl acetate (30 mL×3). The combined organic layers were washed with brine (20 mL), dried over Na₂SO₄ and concentrated. The crude mixture was purified by preparative HPLC to give 5-chloro-1-isopropyl-3-methyl-N-((5-methyl-1,3,4-oxadiazol-2-yl)methyl)-1H-pyrazolo[4,3-b]pyridin-7-amine (50 mg).

To a solution of 5-chloro-1-isopropyl-3-methyl-N-((5-methyl-1,3,4-oxadiazol-2-yl)methyl)-1H-pyrazolo[4,3-b]pyridin-7-amine (50 mg, 70 μmop and (2-ethoxypyridin-3-yl)boronic acid (21 mg, 0.13 mmol) in dioxane (2 mL) and H₂O (0.7 mL) was added Cs₂CO₃ (57 mg, 175 μmol) and Pd(1,1'-bis(diphenylphosphino)ferrocene)Cl₂ (10 mg, 14 μmol). The mixture was purged with nitrogen for 3 minutes then stirred at 100° C. for 30 minutes under microwave irradiation. Water (30 mL) was added and the mixture was extracted with ethyl acetate (30 mL×3). The combined organic layers were washed with brine (20 mL), dried over Na₂SO₄ and concentrated. The crude mixture was purified by preparative TLC with dichloromethane:methanol=20:1 twice, and then the crude product was further purified by preparative HPLC to give 5-(2-ethoxypyridin-3-yl)-1-isopropyl-3-methyl-N-((5-methyl-1,3,4-oxadiazol-2-yl)methyl)-1H-pyrazolo[4,3-b]pyridin-7-amine (6.1 mg).

¹H NMR (chloroform-d, 400 MHz) δ 8.28-8.26 (m, 1H), 8.19-8.18 (m, 1H), 7.23 (s, 1H), 7.05-7.02 (m, 1H), 5.27 (brs, 1H), 4.96-4.90 (m, 1H), 4.71 (d, J=1.2 Hz, 2H), 4.53-4.48 (m, 2H), 2.65 (s, 3H), 2.57 (s, 3H), 1.66 (d, J=6.4 Hz, 6H), 1.43 (t, J=6.8 Hz, 3H). LC-MS (m/z) 408.2 (MH⁺); $t_R$=2.08 minutes (Method B).

The following examples were prepared in a similar manner:

Supporting Example S12: 1-cyclopropyl-5-(2-ethoxy-3-pyridyl)-3-methyl-N-[(1-methylpyrazol-4-yl)methyl]pyrazolo[4,3-b]pyridin-7-amine

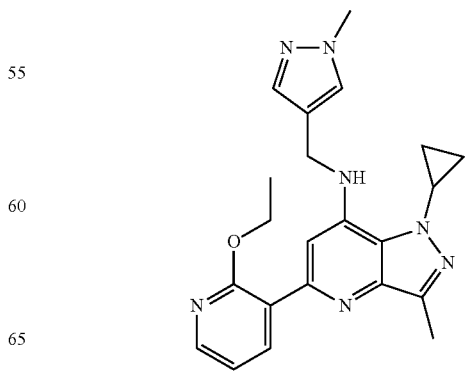

Prepared from (1-methyl-1H-pyrazol-4-yl)methanamine and 5,7-dibromo-1-cyclopropyl-3-methyl-1H-pyrazolo[4,3-b]pyridine.

$^1$H NMR (Cloroform-d, 400 MHz): δ 8.26-8.23 (m, 1H), 8.19-8.17 (m, 1H), 7.57 (s, 1H), 7.44 (s, 1H), 7.16 (s, 1H), 7.04-7.01 (m, 1H), 5.64 (brs, 1H), 4.50-4.45 (m, 2H), 4.39 (d, J=4.4 Hz, 2H), 3.93 (s, 3H), 3.72-3.70 (m, 1H), 2.61 (s, 3H), 1.46-1.38 (m, 5H), 1.16-1.11 (m, 2H). LC-MS (m/z) 404.1 (MH$^+$); $t_R$=1.88 minutes (Method C).

Supporting Example S13: 5-(2-ethoxy-3-pyridyl)-N-[(1-methylpyrazol-4-yl)methyl]-1-propyl-pyrazolo[4,3-b]pyridin-7-amine

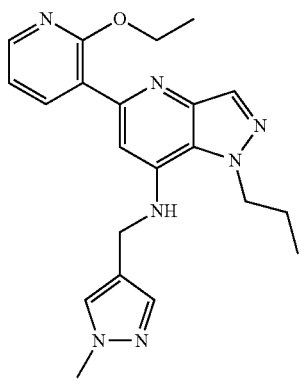 [SMILES: CCCn1ncc2nc(-c3cccnc3OCC)cc(NCc3cnn(C)c3)c21]

Prepared from (1-methyl-1H-pyrazol-4-yl)methanamine dihydrochloride and 5,7-dibromo-1-propyl-1H-pyrazolo[4,3-b]pyridine.

$^1$H NMR (Chloroform-d, 400 MHz) δ 8.16-8.11 (m, 2H), 8.04 (s, 1H), 7.49 (s, 1H), 7.37 (s, 1H), 7.17 (s, 1H), 6.97-6.94 (m, 1H), 4.42-4.32 (m, 7H), 3.86 (s, 3H), 1.85 (q, J=7.2 Hz, 2H), 1.33 (t, J=7.2 Hz, 3H), 0.86 (t, J=7.2 Hz, 3H). LC-MS (m/z) 392.2 (MH$^+$); $t_R$=1.87 minutes (Method C).

Supporting Example S14: 5-(2-ethoxypyridin-3-yl)-N-((1-methyl-1H-pyrazol-4-yl)methyl)-1-(oxetan-3-yl)-1H-pyrazolo[4,3-b]pyridin-7-amine

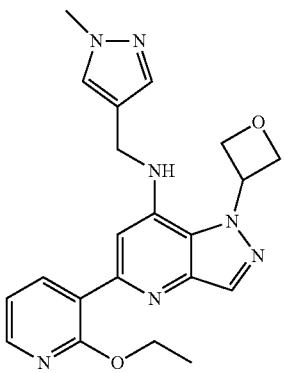 [SMILES: CCOc1ncccc1-c1cc(NCc2cnn(C)c2)c2c(cnn2C2COC2)n1]

Prepared from (1-methyl-1H-pyrazol-4-yl)methanamine and 7-bromo-5-chloro-1-(oxetan-3-yl)-1H-pyrazolo[4,3-b]pyridine.

$^1$H NMR (Methanol-d$_4$, 600 MHz) δ 8.18-8.14 (m, 2H), 7.95 (dd, J=7.3, 2.0 Hz, 1H), 7.62 (s, 1H), 7.51 (s, 1H), 7.08-7.04 (m, 2H), 6.24-6.17 (m, 1H), 5.24-5.18 (m, 2H), 5.15-5.08 (m, 2H), 4.45 (s, 2H), 4.38 (q, J=7.0 Hz, 2H), 3.85 (s, 3H), 1.26 (t, J=7.0 Hz, 3H). LC-MS (m/z) 406.2 (MH$^+$); $t_R$=0.41 minutes (Method D).

Supporting Example S17: 5-(2-ethoxy-3-pyridyl)-1-isopropyl-N-[(1-methylimidazol-2-yl)methyl]pyrazolo[4,3-b]pyridin-7-amine

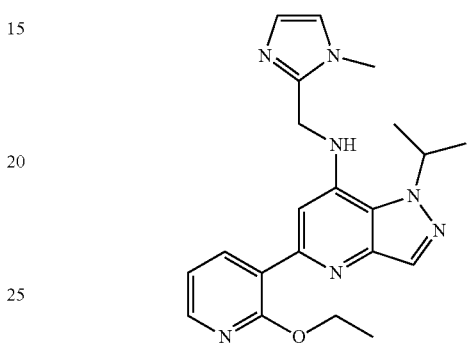

Prepared from (1-methyl-1H-imidazol-2-yl)methanamine and 5,7-dibromo-1-isopropyl-1H-pyrazolo[4,3-b]pyridine.

$^1$H NMR (DMSO-d$_6$, 600 MHz) δ 8.19 (dd, J=4.9, 2.0 Hz, 1H), 8.09-8.12 (m, 2H), 7.35 (s, 1H), 7.13-7.05 (m, 2H), 6.83-6.76 (m, 2H), 5.25 (hept, J=6.5 Hz, 1H), 4.56 (d, J=4.9 Hz, 2H), 4.42 (q, J=7.0 Hz, 2H), 3.71 (s, 3H), 1.51 (d, J=6.4 Hz, 6H), 1.38 (t, J=7.0 Hz, 3H). LC-MS (m/z) 392.1 (MH$^+$); $t_R$=0.35 minutes (Method D).

Supporting Example S23: 5-(2-ethoxy-3-pyridyl)-1-isopropyl-N-(m-tolylmethyl)pyrazolo[4,3-b]pyridin-7-amine

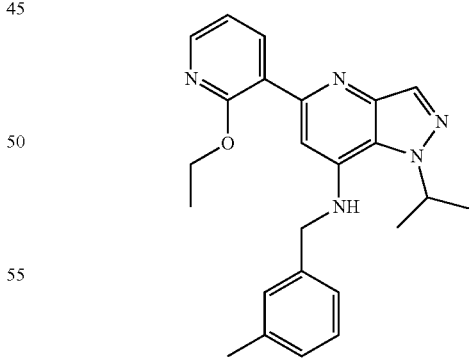

Prepared from m-tolylmethanamine hydrochloride and 5,7-dibromo-1-isopropyl-1H-pyrazolo[4,3-b]pyridine.

$^1$H NMR (Chloroform-d, 400 MHz) δ 8.22-8.17 (m, 3H), 7.33-7.19 (m, 5H), 7.03-7.00 (m, 1H), 4.89-4.86 (m, 2H), 4.53 (d, J=5.2 Hz, 2H), 4.42 (q, J=7.2 Hz, 2H), 2.39 (s, 3H), 1.65 (d, J=6.4 Hz, 6H), 1.33 (t, J=7.2 Hz, 3H). LC-MS (m/z) 402.1 (MH$^+$); $t_R$=2.57 minutes (Method F).

Supporting Example S26: 5-(2-ethoxy-3-pyridyl)-1-ethyl-N-[(1-methylpyrazol-4-yl)methyl]pyrazolo[4,3-b]pyridin-7-amine

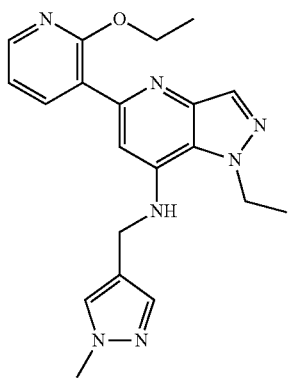 [SMILES: CCOc1ncccc1-c1cc(NCc2cnn(C)c2)c2c(cnn2CC)n1]

Prepared from (1-methyl-1H-pyrazol-4-yl)methanamine and 5,7-dibromo-1-ethyl-1H-pyrazolo[4,3-b]pyridine.

$^1$H NMR (Chloroform-d, 400 MHz) δ 8.22-8.11 (m, 3H), 7.56 (s, 1H), 7.43 (s, 1H), 7.23 (s, 1H), 7.03-7.00 (m, 1H), 4.56-4.39 (m, 7H), 3.92 (s, 3H), 1.51 (t, J=7.2 Hz, 3H), 1.38 (t, J=7.2 Hz, 3H). LC-MS (m/z) 378.2 (MH$^+$); $t_R$=1.79 minutes (Method G).

Supporting Example S28: 5-(2-ethoxy-3-pyridyl)-1,3-dimethyl-N-[(1-methylpyrazol-4-yl)methyl]pyrazolo[4,3-b]pyridin-7-amine

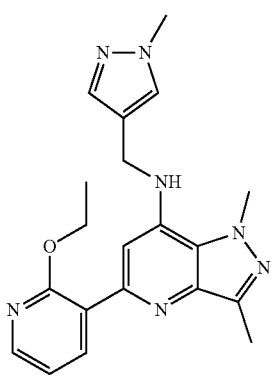 [SMILES: CCOc1ncccc1-c1cc(NCc2cnn(C)c2)c2c(n1)c(C)nn2C]

Prepared from (1-methyl-1H-pyrazol-4-yl)methanamine and 5,7-dichloro-1,3-dimethyl-1H-pyrazolo[4,3-b]pyridine.

$^1$H NMR (Chloroform-d, 400 MHz) δ 8.28-8.26 (m, 1H), 8.19-8.18 (m, 1H), 7.56 (s, 1H), 7.44 (s, 1H), 7.21 (s, 1H), 7.04-7.01 (m, 1H), 4.63 (brs, 1H), 4.47 (q, J=6.8 Hz, 2H), 4.38 (d, J=4.8 Hz, 2H), 4.23 (s, 3H), 3.92 (s, 3H), 2.62 (s, 3H), 1.39 (t, J=7.2 Hz, 3H). LC-MS (m/z) 378.2 (MH$^+$); $t_R$=1.93 minutes (Method B).

Supporting Example S29: 5-(2-ethoxypyridin-3-yl)-1-isopropyl-3-methyl-N-((4-methylthiazol-2-yl)methyl)-1H-pyrazolo[4,3-b]pyridin-7-amine

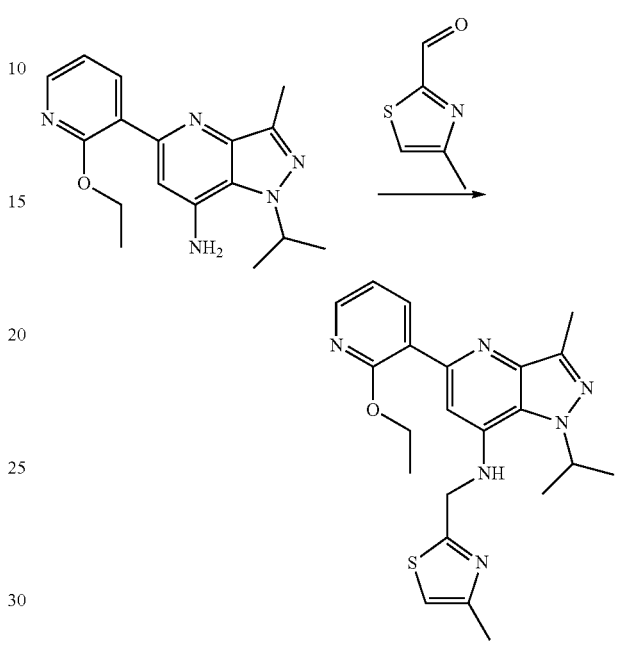

To a solution of 5-(2-ethoxypyridin-3-yl)-1-isopropyl-3-methyl-1H-pyrazolo[4,3-b]pyridin-7-amine (50 mg, 0.16 mmol) in THF (3 mL) was added Ti(i-PrO)$_4$ (91 mg, 0.32 mmol, 95 μL) and 4-methylthiazole-2-carbaldehyde (41 mg, 0.32 mmol, 35 μL). The mixture was stirred at 50° C. for 18 hours. The reaction mixture was cooled to 0° C., then NaBH$_4$ (30 mg, 0.80 mmol) was added into the mixture slowly and the reaction was stirred at 0° C. for 10 min. Water (2 mL) was added to quench the reaction, the resulting mixture was filtered and the residue was washed with ethyl acetate (20 mL×2). The combined filtrates were washed with brine (10 mL), dried over Na$_2$SO$_4$, and concentrated. The residue was purified by column chromatography (SiO$_2$, petroleum ether:ethyl acetate=2:1 to 1:1) followed by purification by preparative HPLC to give 5-(2-ethoxypyridin-3-yl)-1-isopropyl-3-methyl-N-((4-methylthiazol-2-yl)methyl)-1H-pyrazolo[4,3-b]pyridin-7-amine (14 mg).

$^1$H NMR (Cloroform-d, 400 MHz) δ 8.26-8.24 (m, 1H), 8.18-8.17 (m, 1H), 7.19 (s, 1H), 7.03-7.00 (m, 1H), 6.87 (s, 1H), 5.01-4.95 (m, 1H), 4.82 (d, J=4.8 Hz, 2H), 4.47-4.42 (q, J=7.2 Hz, 2H), 2.66 (s, 3H), 2.48 (s, 3H), 1.68 (d, J=6.4 Hz, 6H), 1.37 (t, J=7.2 Hz, 3H). LC-MS (m/z) 423.0 (MH$^+$); $t_R$=1.92 minutes (Method C).

The following examples were prepared in a similar manner:

Supporting Example S41: N-benzyl-5-(2-ethoxy-3-pyridyl)-1-isopropyl-pyrazolo[4,3-b]pyridin-7-amine

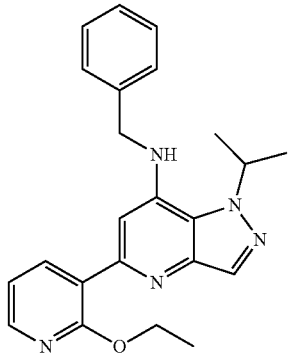 [SMILES: CCOc1ncccc1-c1cc(NCc2ccccc2)c2c(cnn2C(C)C)n1]

Prepared from benzaldehyde and 5-(2-ethoxypyridin-3-yl)-1-isopropyl-1H-pyrazolo[4,3-b]pyridin-7-amine.

$^1$H NMR (DMSO-$d_6$, 600 MHz) δ 8.16-8.07 (m, 3H), 7.43-7.38 (m, 2H), 7.35 (dd, J=8.4, 7.0 Hz, 2H), 7.27-7.21 (m, 1H), 7.04 (dd, J=7.4, 4.9 Hz, 2H), 6.96 (s, 1H), 5.34 (hept, J=6.4 Hz, 1H), 4.58 (d, J=5.6 Hz, 2H), 4.23 (q, J=7.0 Hz, 2H), 1.56-1.45 (d, J=6.4 Hz, 6H), 1.13 (t, J=7.0 Hz, 3H). LC-MS (m/z) 388 (MH$^+$); $t_R$=0.66 minutes (Method D).

Supporting Example S48: 5-(2-ethoxypyridin-3-yl)-1-ethyl-3-methyl-N-((1-methyl-1H-pyrazol-4-yl)methyl)-1H-pyrazolo[4,3-b]pyridin-7-amine

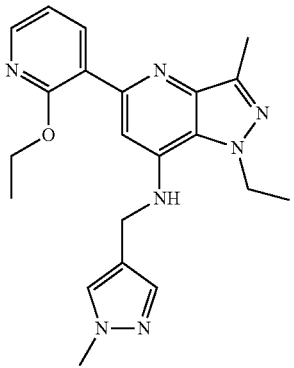 [SMILES: CCOc1ncccc1-c1cc(NCc2cnn(C)c2)c2c(n1)c(C)nn2CC]

Prepared using the same procedure as described for supporting example 1, from (1-methyl-1H-pyrazol-4-yl)methanamine and 5,7-dibromo-1-ethyl-3-methyl-1H-pyrazolo[4,3-b]pyridine.

$^1$H NMR (Chloroform-d, 400 MHz) δ 8.28-8.26 (m, 1H), 8.19-8.17 (m, 1H), 7.56 (s, 1H), 7.43 (s, 1H), 7.23 (s, 1H), 7.04-7.01 (m, 1H), 4.53 (brs, 1H), 4.50-4.45 (m, 4H), 4.40 (d, J=4.8 Hz, 2H), 3.92 (s, 3H), 2.63 (s, 3H), 1.47 (t, J=7.2 Hz, 3H), 1.39 (t, J=7.2 Hz, 3H). LC-MS: LC-MS (m/z) 392.1 (MH$^+$); $t_R$=1.72 min (Method F).

Supporting Example S61: 5-(1,3-dimethylpyrazol-4-yl)-1-isopropyl-3-methyl-N-[(1-methylpyrazol-4-yl)methyl]pyrazolo[4,3-b]pyridin-7-amine

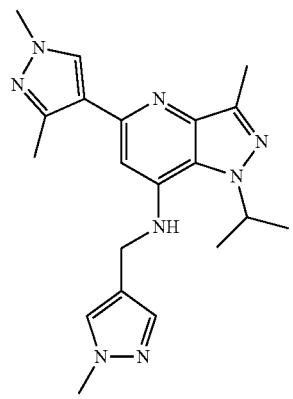 [SMILES: Cc1nn(C)cc1-c1cc(NCc2cnn(C)c2)c2c(n1)c(C)nn2C(C)C]

Prepared using the same procedure as described for example 1, from 5-chloro-1-isopropyl-3-methyl-N-[(1-methylpyrazol-4-yl)methyl]pyrazolo[4,3-b]pyridin-7-amine and 1,3-dimethyl-4-(4,4,5,5-tetramethyl-1,3,2-dioxaborolan-2-yl)pyrazole.

$^1$H NMR (Chloroform-d, 400 MHz): δ 7.75 (s, 1H), 7.55 (s, 1H), 7.40 (s, 1H), 6.56 (s, 1H), 4.74-4.67 (m, 1H), 4.54 (brs, 1H), 4.37 (d, J=4.8 Hz, 2H), 3.92 (s, 3H), 3.87 (s, 3H), 2.60 (s, 3H), 2.50 (s, 3H), 1.56 (d, J=6.4 Hz, 6H). LC-MS (m/z) 379.4 (MH$^+$); $t_R$=0.38 minutes (Method E).

Supporting Example S67: 5-(2-ethoxy-3-pyridyl)-3-methyl-1-[1-methylpropyl]-N-[(1-methylpyrazol-3-yl)methyl]pyrazolo[4,3-b]pyridin-7-amine, enantiomer 2

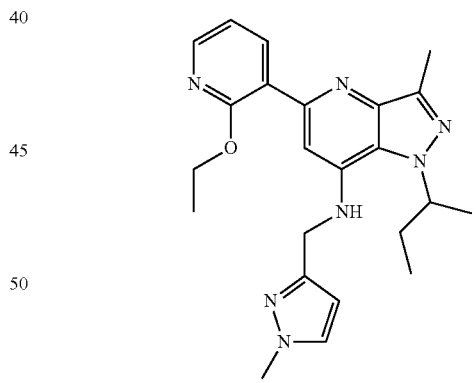

Prepared using the same procedure as described for supporting example 1, from 1-(sec-butyl)-5-(2-ethoxypyridin-3-yl)-3-methyl-1H-pyrazolo[4,3-b]pyridin-7-amine, enantiomer 2, (2-ethoxy-3-pyridyl)boronic acid and (1-methyl-1H-pyrazol-3-yl)methanamine.

$^1$H NMR (Chloroform-d, 400 MHz) δ 8.27 (dd, J=1.6, 7.2 Hz, 1H), 8.17 (dd, J=1.6, 4.8 Hz, 1H), 7.37 (d, J=2.0 Hz, 1H), 7.21 (s, 1H), 7.02 (dd, J=4.8, 7.6 Hz, 1H), 6.25 (d, J=2.0 Hz, 1H), 5.24 (brs, 1H), 4.65-4.60 (m, 1H), 4.51-4.46 (m, 4H), 3.92 (s, 3H), 2.65 (s, 3H), 2.22-2.15 (m, 1H), 1.92-1.85 (m, 1H), 1.62 (d, J=6.4 Hz, 3H), 1.43 (t, J=6.8 Hz, 3H), 0.92 (t, J=7.6 Hz, 3H). LC-MS (m/z) 420.1 (MH$^+$); $t_R$=1.87 (Method A).

Supporting Example S69: 5-(2-ethoxy-3-pyridyl)-1-[1-methylpropyl]-N-[(1-methylpyrazol-4-yl)methyl]pyrazolo[4,3-b]pyridin-7-amine, enantiomer 1

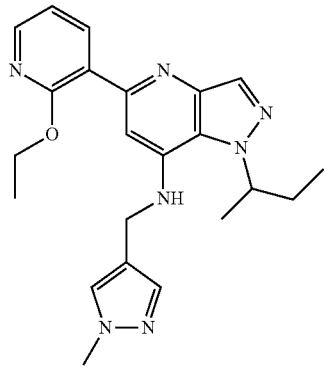 [SMILES: CCOc1ncccc1-c1cc(NCc2cnn(C)c2)c2c(cnn2C(C)CC)n1]

Prepared using the same procedure as described for supporting example 1, from 1-(sec-butyl)-5-(2-ethoxypyridin-3-yl)-1H-pyrazolo[4,3-b]pyridin-7-amine, enantiomer 1, (2-ethoxy-3-pyridyl)boronic acid and (1-methyl-1H-pyrazol-4-yl)methanamine.

$^1$H NMR (Chloroform-d, 400 MHz) δ 8.18-8.14 (m, 2H), 8.11 (s, 1H), 7.59 (s, 1H), 7.40 (s, 1H), 7.11-7.07 (m, 2H), 6.73-6.72 (m, 1H), 5.01-4.96 (m, 1H), 4.39-4.33 (m, 4H), 3.77 (s, 3H), 2.00-1.97 (m, 1H), 1.81-1.79 (m, 1H), 1.49 (d, J=6.8 Hz, 3H), 1.25 (t, J=6.8 Hz, 3H), 0.73 (t, J=7.2 Hz, 3H). SFC-MS: $t_R$=4.72 min, ee %=97.51. LC-MS (m/z) 406.1 (MH$^+$); $t_R$=2.09 (Method A).

Supporting Example S113: 5-(2-ethoxy-3-pyridyl)-3-methyl-N-[(2-methylthiazol-4-yl)methyl]-1-(oxetan-3-yl)pyrazolo[4,3-b]pyridin-7-amine

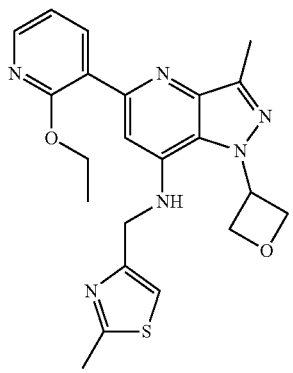 [SMILES: CCOc1ncccc1-c1cc(NCc2csc(C)n2)c2c(n1)c(C)nn2C1COC1]

Prepared using the same procedure as described for supporting example 1, from 5,7-dibromo-3-methyl-1-(oxetan-3-yl)pyrazolo[4,3-b]pyridine, (2-ethoxy-3-pyridyl)boronic acid and (2-methylthiazol-4-yl)methanamine.

$^1$H NMR (Chloroform-d, 400 MHz) δ 8.26 (dd, J=1.6, 7.2 Hz 1H), 8.18 (dd, J=2.0, 4.8 Hz 1H), 7.24 (s, 1H), 7.05-7.02 (m, 2H), 5.94-5.85 (m, 2H), 5.28-5.25 (m, 2H), 5.20-5.16 (m, 2H), 4.57 (d, J=5.2 Hz, 2H), 4.46 (q, J=7.2 Hz, 2H), 2.76 (s, 3H), 2.66 (s, 3H), 1.39 (t, J=7.2 Hz, 3H). LC-MS (m/z) 437.4 (MH$^+$); $t_R$=0.46 minutes (Method E).

Supporting Example S120: 5-(2-ethoxy-3-pyridyl)-3-methyl-1-[1-methylpropyl]-N-(1H-pyrazol-3-ylmethyl)pyrazolo[4,3-b]pyridin-7-amine, enantiomer 2

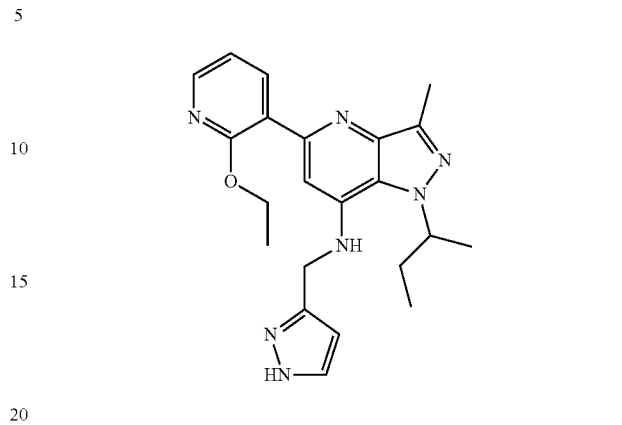

Prepared using the same procedure as described for supporting example 29, from 1-(sec-butyl)-5-(2-ethoxypyridin-3-yl)-3-methyl-1H-pyrazolo[4,3-b]pyridin-7-amine, enantiomer 2 and 1H-pyrazole-3-carbaldehyde.

$^1$H NMR (Chloroform-d, 400 MHz): δ 8.26 (dd, J=2.0, 7.2 Hz, 1H), 8.18 (dd, J=2.0, 4.2 Hz, 1H), 7.60 (d, J=2.4 Hz, 1H), 7.22 (s, 1H), 7.03 (dd, J=4.8, 7.2 Hz, 1H), 6.36 (d, J=2.4 Hz, 1H), 5.28 (br. s, 1H), 4.64-4.60 (m, 1H), 4.57 (d, J=4.8 Hz, 2H), 4.48 (q, J=6.8 Hz, 2H), 2.66 (s, 3H), 2.22-2.14 (m, 1H), 1.92-1.86 (m, 1H), 1.62 (d, J=6.8 Hz, 3H), 1.43 (t, J=6.8 Hz, 3H), 0.89 (t, J=7.2 Hz, 3H). LC-MS (m/z) 406.1 (MH$^+$); $t_R$=2.22 (Method A).

Supporting Example S147: 1-isopropyl-3-methyl-N-[(1-methylpyrazol-4-yl)methyl]-5-thiazol-2-yl-pyrazolo[4,3-b]pyridin-7-amine

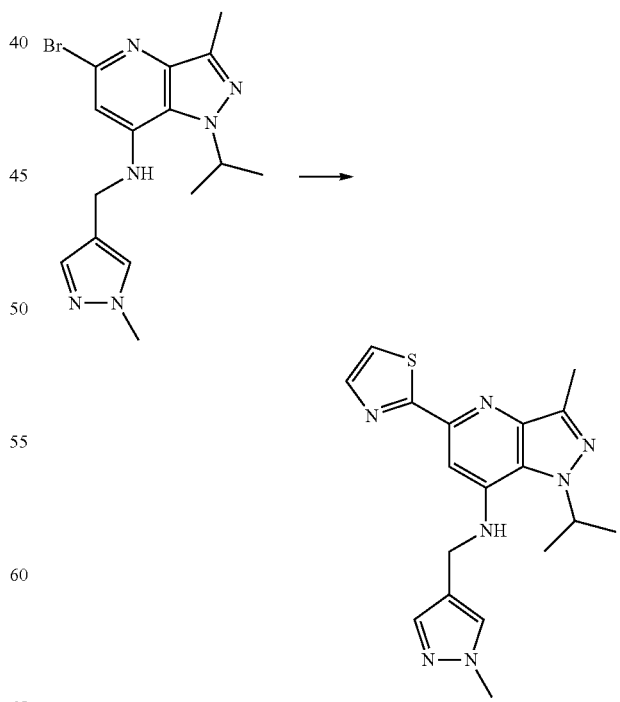

To a solution of 5-bromo-1-isopropyl-3-methyl-N-((1-methyl-1H-pyrazol-4-yl)methyl)-1H-pyrazolo[4,3-b]pyridin-7-amine (50 mg, 0.14 mmol) in DMF (2 mL) was added 2-(tributylstannyl)thiazole (103 mg, 0.28 mmol) and Pd(PPh₃)₄ (16 mg, 0.013 mmol). The mixture was bubbled with N₂ and heated at 80° C. for 2 hours. The mixture was cooled to room temperature. ethyl acetate (20 mL) and water (10 mL) were added. The organic layer was washed with water (10 mL×2), brine (10 mL), dried over Na₂SO₄, filtered and concentrated. The crude was purified by preparative TLC (SiO₂, ethyl acetate) to give 1-isopropyl-3-methyl-N-((1-methyl-1H-pyrazol-4-yl)methyl)-5-(thiazol-2-yl)-1H-pyrazolo[4,3-b]pyridin-7-amine (10 mg).

¹H NMR (Chloroform-d, 400 MHz): δ 7.88 (d, J=3.2 Hz, 1H), 7.58 (s, 1H), 7.46 (s, 2H), 7.40 (d, J=3.2 Hz, 1H), 4.75-4.68 (m, 1H), 4.54 (brs, 1H), 4.46 (d, J=4.8 Hz, 2H), 3.94 (s, 3H), 2.65 (s, 3H), 1.58 (d, J=6.8 Hz, 6H). LC-MS (m/z) 368 (MH⁺); t$_R$=1.91 (Method C).

Supporting Example S161: 5-(2-ethoxy-3-pyridyl)-1-isopropyl-3-methyl-N-[(2-methyl-1,2,4-triazol-3-yl)methyl]pyrazolo[4,3-b]pyridin-7-amine and Supporting Example S162: 5-(2-ethoxy-3-pyridyl)-1-isopropyl-3-methyl-N-[(4-methyl-1,2,4-triazol-3-yl)methyl]pyrazolo[4,3-b]pyridin-7-amine

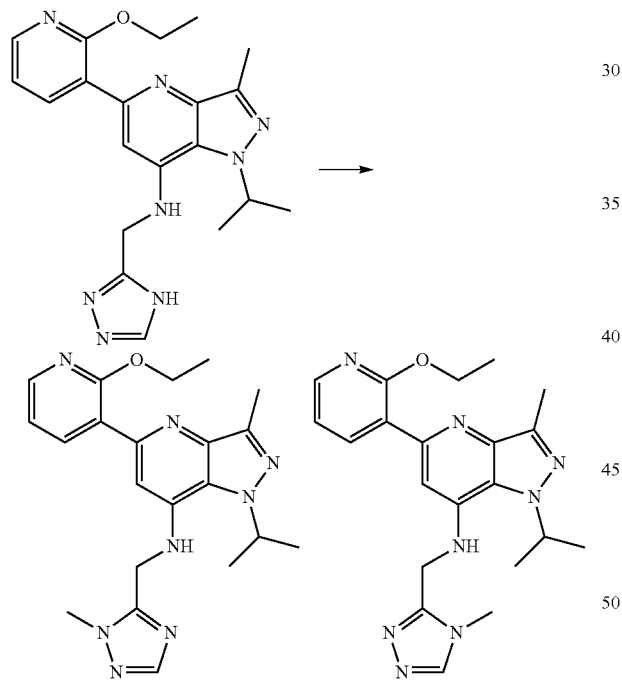

Cs₂CO₃ (16.6 mg, 0.051 mmol) and iodomethane (510 µl, 0.051 mmol, 100 mM, THF) were added to N-((4H-1,2,4-triazol-3-yl)methyl)-5-(2-ethoxypyridin-3-yl)-1-isopropyl-3-methyl-1H-pyrazolo[4,3-b]pyridin-7-amine (20 mg, 0.051 mmol) in THF (1.3 mL). The reaction mixture was stirred in a sealed vial at 80° C. for 50 minutes. The reaction mixture was concentrated in vacuo. Water was added. The mixture was extracted with ethyl acetate. The organic phase was washed with brine, dried over MgSO4, filtered and concentrated in vacuo. The residue was purified by SFC to give 5-(2-ethoxypyridin-3-yl)-1-isopropyl-3-methyl-N-((1-methyl-1H-1,2,4-triazol-5-yl)methyl)-1H-pyrazolo[4,3-b]pyridin-7-amine (2 mg) and 5-(2-ethoxypyridin-3-yl)-1-isopropyl-3-methyl-N-((4-methyl-4H-1,2,4-triazol-3-yl)methyl)-1H-pyrazolo[4,3-b]pyridin-7-amine (1 mg)

Supporting Example S161: 5-(2-ethoxy-3-pyridyl)-1-isopropyl-3-methyl-N-[(2-methyl-1,2,4-triazol-3-yl)methyl]pyrazolo[4,3-b]pyridin-7-amine ¹H NMR (600 MHz, Chloroform-d) δ 8.28 (dt, J=7.3, 1.4 Hz, 1H), 8.19 (dd, J=4.9, 1.9 Hz, 1H), 7.92 (s, 1H), 7.17 (s, 1H), 7.05 (dd, J=7.3, 4.9 Hz, 1H), 5.72 (s, 1H), 4.98 (hept, J=6.6 Hz, 1H), 4.56 (d, J=4.1 Hz, 2H), 4.49 (q, J=7.0 Hz, 2H), 3.95 (s, 3H), 2.66 (s, 3H), 1.66 (d, J=6.5 Hz, 6H), 1.44 (t, J=7.0 Hz, 3H). LC-MS (m/z) 407.4 (MH⁺); t$_R$=0.51 (Method D).

Supporting Example S162: 5-(2-ethoxy-3-pyridyl)-1-isopropyl-3-methyl-N-[(4-methyl-1,2,4-triazol-3-yl)methyl]pyrazolo[4,3-b]pyridin-7-amine ¹H NMR (600 MHz, DMSO-d₆) δ 8.43 (s, 1H), 8.19 (dd, J=4.9, 1.9 Hz, 1H), 8.12 (dd, J=7.3, 2.0 Hz, 1H), 7.32 (s, 1H), 7.09 (dd, J=7.4, 4.8 Hz, 1H), 6.80 (t, J=5.2 Hz, 1H), 5.17 (hept, J=6.8 Hz, 1H), 4.67 (d, J=5.0 Hz, 2H), 4.42 (q, J=7.0 Hz, 2H), 3.71 (s, 3H), 2.46 (s, 3H), 1.45 (d, J=6.3 Hz, 6H), 1.36 (t, J=7.0 Hz, 3H). LC-MS (m/z) 407.4 (MH⁺); t$_R$=0.49 (Method D).

Supporting Example S163: 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine

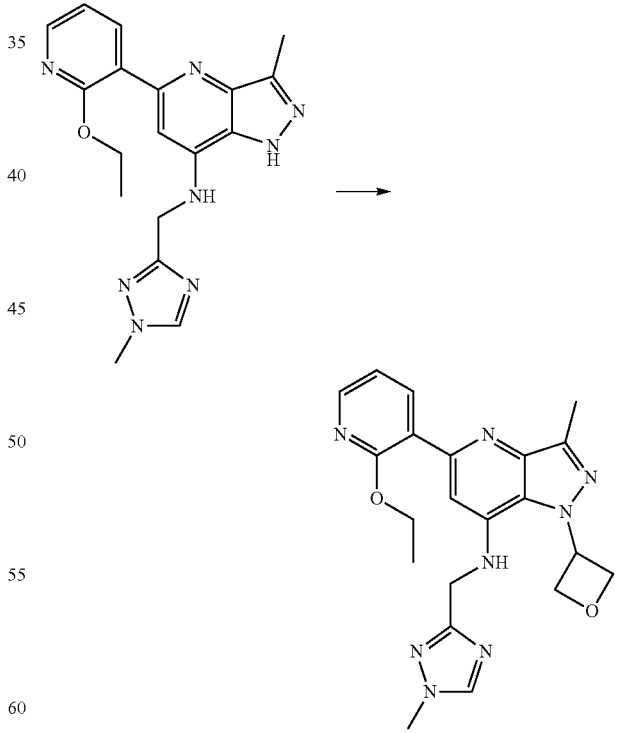

A suspension of 5-(2-ethoxypyridin-3-yl)-3-methyl-N-((1-methyl-1H-1,2,4-triazol-3-yl)methyl)-1H-pyrazolo[4,3-b]pyridin-7-amine (80 mg, 0.22 mmol, prepared using the same procedure as described for example 29, from 5-(2-ethoxypyridin-3-yl)-3-methyl-1H-pyrazolo[4,3-b]pyridin- 7-amine and 1-methyl-1,2,4-triazole-3-carbaldehyde), 3-iodooxetane (81 mg, 0.44 mmol) and t-BuOK (215 mg, 1.91 mmol) in DMF (2 mL) was heated to 120° C. for 34 hours. The reaction mixture was cooled to room temperature and concentrated in vacuo. The residue was purified by preparative HPLC twice to give 5-(2-ethoxy-3-pyridyl)-3-methyl-N-[(1-methyl-1,2,4-triazol-3-yl)methyl]-1-(oxetan-3-yl)pyrazolo[4,3-b]pyridin-7-amine (8 mg).

$^1$H NMR (Cloroform-d, 400 MHz) δ 8.28 (dd, J=2.2, 7.4 Hz, 1H), 8.19 (dd, J=2.0, 4.8 Hz, 1H), 8.06 (s, 1H), 7.26 (s, 1H), 7.03 (dd, J=4.8, 7.4 Hz, 1H), 5.97-5.93 (m, 1H), 5.34 (t, J=6.4 Hz, 2H), 5.19 (t, J=7.2 Hz, 2H), 4.57 (d, J=5.2 Hz, 2H), 4.49 (q, J=6.8 Hz, 2H), 3.96 (s, 3H), 2.67 (s, 3H), 1.44 (t, J=7.2 Hz, 3H). LC-MS (m/z) 421.1 (MH$^+$); $t_R$=2.04 (Method B).

Supporting example S165: N-[[1-(difluoromethyl)pyrazol-4-yl]methyl]-5-(2-ethoxy-3-pyridyl)-1-isopropyl-3-methyl-pyrazolo[4,3-b]pyridin-7-amine

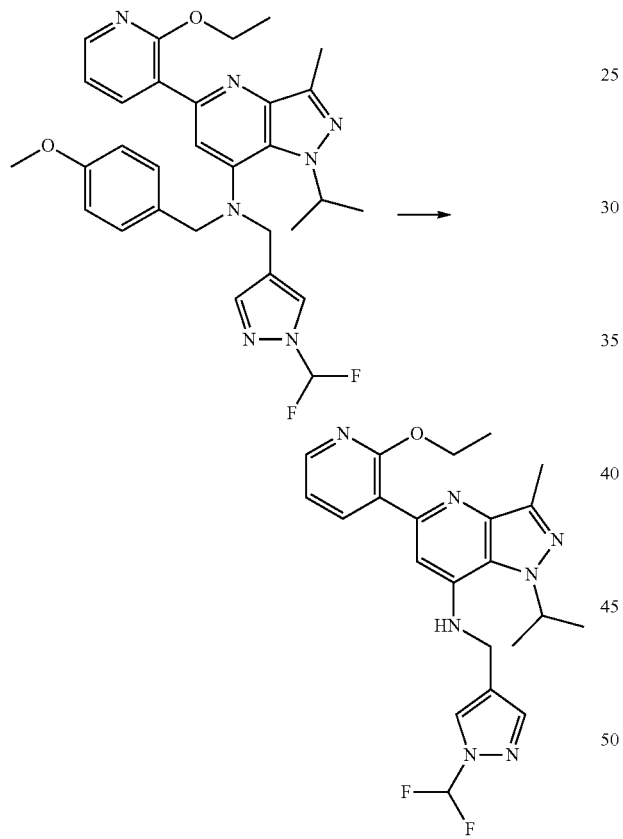

To a solution of N-((1-(difluoromethyl)-1H-pyrazol-4-yl)methyl)-5-(2-ethoxypyridin-3-yl)-1-isopropyl-N-(4-methoxybenzyl)-3-methyl-1H-pyrazolo[4,3-b]pyridin-7-amine (15 mg, 0.027 mmol) in DCM (0.5 mL) was added trifluoro acetic acid (0.5 mL). The mixture was stirred at room temperature for 1 hour. Water (3 mL) was added and the mixture was poured into a saturated, aqueous solution of NaHCO$_3$. The mixture was extracted with ethyl acetate (5 mL×3). The combined organic layers were washed with brine (5 mL), dried over Na$_2$SO$_4$ and concentrated. The crude mixture was purified by flash chromatography with heptane:ethyl acetate=1:0 to 0:1 to give N-((1-(difluoromethyl)-1H-pyrazol-4-yl)methyl)-5-(2-ethoxypyridin-3-yl)-1-isopropyl-3-methyl-1H-pyrazolo[4,3-b]pyridin-7-amine (11 mg, 0.025 mmol, 93% yield).

$^1$H NMR (600 MHz, Chloroform-d) δ 8.26 (dd, J=7.4, 2.0 Hz, 1H), 8.17 (dd, J=4.9, 2.0 Hz, 1H), 7.84 (d, J=2.7 Hz, 1H), 7.20 (s, 1H), 7.17 (t, J=60.7 Hz, 1H), 7.02 (dd, J=7.3, 4.9 Hz, 1H), 6.49 (d, J=2.7 Hz, 1H), 5.24 (s, 1H), 4.91 (hept, J=6.6 Hz, 1H), 4.57 (d, J=4.8 Hz, 2H), 4.47 (q, J=7.0 Hz, 2H), 2.65 (s, 3H), 1.65 (d, J=6.5 Hz, 6H), 1.40 (t, J=7.0 Hz, 3H). LC-MS (m/z) 442.5 (MH$^+$); $t_R$=0.60 minutes (Method D).

Supporting Example S168: 1-isopropyl-3-methyl-N-[(1-methylpyrazol-4-yl)methyl]-5-oxazol-2-yl-pyrazolo[4,3-b]pyridin-7-amine

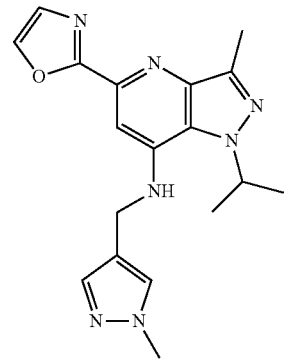 [SMILES: Cc1nn(C(C)C)c2c(NCc3cnn(C)c3)cc(-c3ncco3)nc12]

Prepared using the same procedure as described for supporting example 147 from 5-bromo-1-isopropyl-3-methyl-N-((1-methyl-1H-pyrazol-4-yl)methyl)-1H-pyrazolo[4,3-b]pyridin-7-amine and tributyl(oxazol-2-yl)stannane.

$^1$H NMR (Chloroform-d, 400 MHz): δ 7.83 (s, 1H), 7.59 (s, 1H), 7.46 (s, 1H), 7.39 (s, 1H), 7.29 (s, 1H), 4.76-4.70 (m, 1H), 4.58 (brs, 1H), 4.44 (d, J=4.2 Hz, 2H), 3.94 (s, 3H), 2.69 (s, 3H), 1.59 (d, J=6.4 Hz, 6H). LC-MS (m/z) 352 (MH$^+$); $t_R$=1.75 minutes (Method C).

Supporting Example S169: 1-isopropyl-3-methyl-N-[(1-methylpyrazol-4-yl)methyl]-5-(3-methyltriazol-4-yl)pyrazolo[4,3-b]pyridin-7-amine

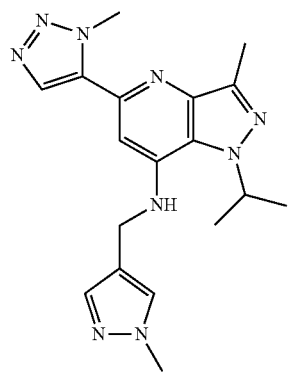 [SMILES: Cc1nn(C(C)C)c2c(NCc3cnn(C)c3)cc(-c3cnnn3C)nc12]

Prepared using the same procedure as described for example 147 from 5-bromo-1-isopropyl-3-methyl-N-((1-methyl-1H-pyrazol-4-yl)methyl)-1H-pyrazolo[4,3-b]pyridin-7-amine and 1-methyl-5-(tributylstannyl)-1H-1,2,3-triazole.

¹H NMR (Chloroform-d, 400 MHz): δ 7.93 (s, 1H), 7.57 (s, 1H), 7.45 (s, 1H), 6.70 (s, 1H), 4.76-4.69 (m, 1H), 4.65 (brs, 1H), 4.48 (s, 3H), 4.39 (d, J=4.4 Hz, 2H), 3.95 (s, 3H), 2.62 (s, 3H), 1.60 (d, J=6.4 Hz, 6H). LC-MS (m/z) 366 (MH⁺); $t_R$=1.69 minutes (Method C).

Supporting Example S184: 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine

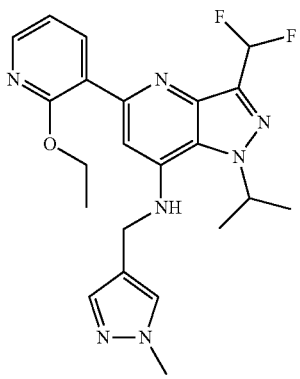 [SMILES: CCOc1ncccc1-c1cc(NCc2cnn(C)c2)c2c(n1)c(C(F)F)nn2C(C)C]

A solution of 7-chloro-3-(difluoromethyl)-5-(2-ethoxypyridin-3-yl)-1-isopropyl-1H-pyrazolo[4,3-b]pyridine (3.0 mg, 6.5 µmol), (1-methyl-1H-pyrazol-4-yl)methanamine (29.0 mg, 0.26 mmol) in NMP (0.22 ml) in a sealed vial was inserted in an oil bath at 155° C. and stirred for 16 hours The mixture was partitioned between ethyl acetate (20 ml) and water (2×15 ml). The organic layer was washed with brine (10 ml), dried (Na₂SO₄) and concentrated. Flash chromatography on silica gel (elution gradient from heptane to ethyl acetate) delivered 3-(difluoromethyl)-5-(2-ethoxypyridin-3-yl)-1-isopropyl-N-((1-methyl-1H-pyrazol-4-yl)methyl)-1H-pyrazolo[4,3-b]pyridin-7-amine.

¹H NMR (Chloroform-d, 600 MHz) δ 8.33 (dd, J=7.4, 2.0 Hz, 1H), 8.18 (dd, J=4.9, 2.0 Hz, 1H), 7.57 (s, 1H), 7.44 (s, 1H), 7.35 (s, 1H), 7.16 (t, J=54.1 Hz, 1H), 7.03 (dd, J=7.4, 4.9 Hz, 1H), 4.82 (hept, J=6.5 Hz, 1H), 4.57 (t, J=5.0 Hz, 1H), 4.47 (q, J=7.0 Hz, 2H), 4.40 (d, J=4.8 Hz, 2H), 3.93 (s, 3H), 1.64 (d, J=6.5 Hz, 6H), 1.39 (t, J=7.0 Hz, 3H). LC-MS (m/z) 442.6 (MH⁺); $t_R$=0.55 minutes (Method D).

Supporting Example S195: 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine

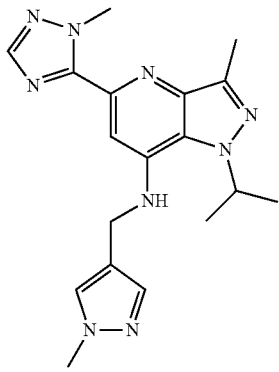 [SMILES: Cc1nn(C(C)C)c2c(NCc3cnn(C)c3)cc(-c3ncnn3C)nc12]

A mixture of 5-bromo-1-isopropyl-3-methyl-N-((1-methyl-1H-pyrazol-4-yl)methyl)-1H-pyrazolo[4,3-b]pyridin-7-amine (0.15 g, 0.41 mmol), 1-methyl-1H-1,2,4-triazole (103 mg, 1.24 mmol), Pd(OAc)₂ (5 mg, 0.021 mmol), Ru-Phos (2-dicyclohexylphosphino-2',6'-diisopropoxybiphenyl) (19 mg, 0.041 mmol), K₂CO₃ (171 mg, 1.24 mmol) and 2,2-dimethylpropanoic acid (21 mg, 0.21 mmol) in xylene (15 mL) was stirred at 140° C. for 12 hours under N₂. The mixture was concentrated under vacuum. The residue was purified by preparative TLC (SiO₂, ethyl acetate/MeOH=10:1) and preparative HPLC to afford 1-isopropyl-3-methyl-5-(1-methyl-1H-1,2,4-triazol-5-yl)-N-((1-methyl-1H-pyrazol-4-yl)methyl)-1H-pyrazolo[4,3-b]pyridin-7-amine.

¹H NMR (Chloroform-d; 400 MHz): δ 7.92 (s, 1H), 7.57 (s, 1H), 7.46 (s, 1H), 7.42 (s, 1H), 4.76-4.70 (m, 1H), 4.59-4.56 (m, 1H), 4.47 (s, 3H), 4.44 (d, J=4.4 Hz, 2H), 3.93 (s, 3H), 2.62 (s, 3H), 1.59 (d, J=6.4 Hz, 6H). LC-MS (m/z) 366.1 (MH⁺); $t_R$=1.72 minutes (Method C).

Supporting Example S197: 5-(2-ethoxy-3-pyridyl)-N-[(2-methoxy-3-pyridyl)methyl]-3-methyl-1-(oxetan-3-yl)pyrazolo[4,3-b]pyridin-7-amine

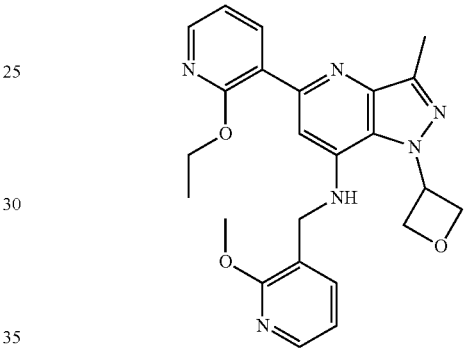

Prepared using the same procedure as described for supporting example 1 from 5,7-dibromo-3-methyl-1-(oxetan-3-yl)pyrazolo[4,3-b]pyridine, (2-methoxy-3-pyridyl)methanamine and (2-ethoxy-3-pyridyl)boronic acid.

¹H NMR (Chloroform-d, 400 MHz): δ 8.27 (dd, J=2.0, 7.6 Hz, 1H), 8.19-8.16 (m, 1H), 8.15-8.12 (m, 1H), 7.59 (d, J=6.4 Hz 1H), 7.23 (s, 1H), 7.04-7.01 (m, 1H), 6.91-6.88 (m, 1H), 6.15 (brs, 1H), 5.90-5.86 (m, 1H), 5.26-5.22 (m, 2H), 5.18-5.15 (m, 2H), 4.53 (d, J=5.6 Hz, 2H), 4.42 (q, J=6.8 Hz, 2H) 4.03 (s, 3H), 2.64 (s, 3H), 1.32 (t, J=6.8 Hz, 3H). LC-MS (m/z) 447 (MH⁺); $t_R$=1.89 minutes (Method C).

Supporting Example S199: 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine

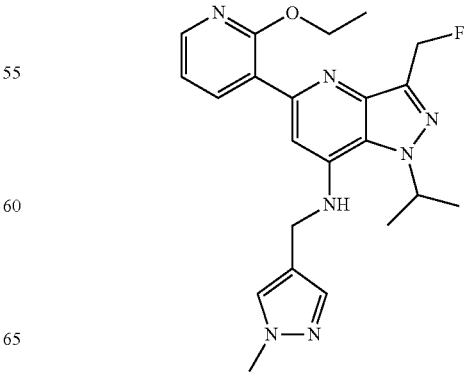

A solution of 7-chloro-5-(2-ethoxypyridin-3-yl)-3-(fluoromethyl)-1-isopropyl-1H-pyrazolo[4,3-b]pyridine (2.0 mg, 5.7 μmol), (1-methyl-1H-pyrazol-4-yl)methanamine (30.0 mg, 0.27 mmol) in NMP (0.2 ml) in a sealed vial was inserted in an oil bath at 155° C. After 20 hours (1-methyl-1H-pyrazol-4-yl)methanamine (30.0 mg, 0.27 mmol) was added and the solution was heated at 155° C. for 15 hours. The mixture was partitioned between ethyl acetate (25 ml) and water (3×20 ml). The organic layer was washed with brine (25 ml), dried ($Na_2SO_4$) and concentrated. The residue was purified by flash chromatography on silica gel (heptane/ethyl acetate) to give 5-(2-ethoxypyridin-3-yl)-3-(fluoromethyl)-1-isopropyl-N-((1-methyl-1H-pyrazol-4-yl)methyl)-1H-pyrazolo[4,3-b]pyridin-7-amine.

$^1$H NMR (DMSO-$d_6$, 600 MHz) δ 8.21-8.15 (m, 2H), 7.61 (s, 1H), 7.42 (s, 1H), 7.14 (s, 1H), 7.10 (dd, J=7.4, 4.9 Hz, 1H), 6.84 (t, J=5.6 Hz, 1H), 5.67 (d, J=49.2 Hz, 2H), 5.28 (hept, J=6.4 Hz, 1H), 4.41-4.33 (m, 4H), 3.77 (s, 3H), 1.51 (d, J=6.5 Hz, 6H), 1.24 (t, J=6.9 Hz, 3H). LC-MS (m/z) 424.6 (MH$^+$); $t_R$=0.5 minutes (Method D).

Supporting Example S200: 1-isopropyl-3-methyl-N-((1-methyl-1H-pyrazol-4-yl)methyl)-5-(4-methyloxazol-5-yl)-1H-pyrazolo[4,3-b]pyridin-7-amine

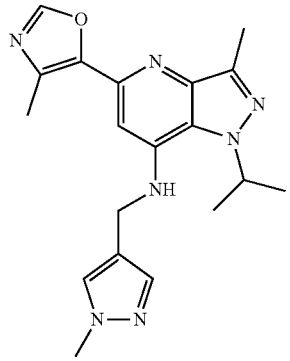 [SMILES: Cc1ncoc1-c1cc(NCc2cnn(C)c2)c2c(n1)c(C)nn2C(C)C]

A mixture of 5-bromo-1-isopropyl-3-methyl-N-((1-methyl-1H-pyrazol-4-yl)methyl)-1H-pyrazolo[4,3-b]pyridin-7-amine (0.15 g, 0.41 mmol), 4-methyloxazole (103 mg, 1.2 mmol), Pd(OAc)$_2$ (5 mg, 0.021 mmol), Ru-Phos (19 mg, 0.041 mmol), $K_2CO_3$ (171 mg, 1.2 mmol) and 2,2-dimethylpropanoic acid (17 mg, 0.17 mmol) in toluene (15 mL) was stirred at 110° C. for 12 hours. The mixture was concentrated under vacuum. The residue was purified by preperative TLC (SiO$_2$, petroleum ether/ethyl acetate=0:1) and preparative HPLC to afford 1-isopropyl-3-methyl-N-((1-methyl-1H-pyrazol-4-yl)methyl)-5-(4-methyloxazol-5-yl)-1H-pyrazolo[4,3-b]pyridin-7-amine.

$^1$H NMR (Chloroform-d; 400 MHz): δ 7.85 (s, 1H), 7.58 (s, 1H), 7.45 (s, 1H), 6.84 (s, 1H), 4.78-4.72 (m, 2H), 4.43 (d, J=4.4 Hz, 2H), 3.94 (s, 3H), 2.68 (s, 3H), 2.62 (s, 3H), 1.58 (d, J=6.4 Hz, 6H). LC-MS (m/z) 366 (MH$^+$); $t_R$=1.6 minutes (Method C).

In vitro Testing

PDE1 Inhibition Assay

PDE1A, PDE1B and PDE1C assays were performed as follows: the assays were performed in 60 μL samples containing a fixed amount of the PDE1 enzyme (sufficient to convert 20-25% of the cyclic nucleotide substrate), a buffer (50 mM HEPES pH 7.6; 10 mM MgCl$_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 hr at room temperature before being terminated through mixing with 20 μL (0.2 mg) yttrium silicate SPA beads (PerkinElmer). The beads were allowed to settle for 1 hr in the dark before the plates were counted in a Wallac 1450 Microbeta counter. The measured signals were converted to activity relative to an uninhibited control (100%) and IC$_{50}$ values were calculated using XIFit (model 205, IDBS).

The invention claimed is:
1. A compound according to formula (I)

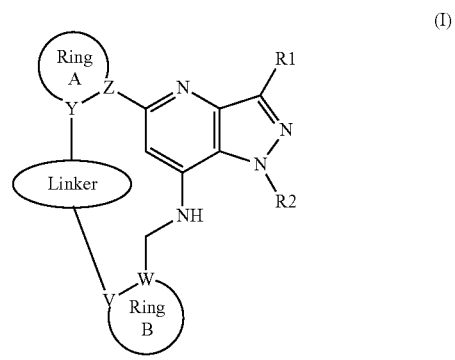

(I)

wherein
ring A is a 5 or 6 membered heteroaromatic ring or ring A is phenyl, and
there is 1 bond between Y and Z;
ring B is a 5 or 6 membered heteroaromatic ring or ring B is phenyl, and
there is 1 bond between V and W;
when ring A is a 5 membered heteroaromatic ring, then one of Y and Z is C and the other is N, or Y═Z═C;
when ring A is a 6 membered heteroaromatic ring or phenyl, then Y═Z═C;
when ring B is a 5 membered heteroaromatic ring, then one of V and W is C and the other is N, or V═W═C;
when ring B is a 6 membered heteroaromatic ring or phenyl, then V═W═C;
the linker is a 5-7 membered saturated chain consisting of carbon and optionally one or more oxygen, with the proviso that the chain contains no O—O bond, and with the proviso that the bond to V cannot be an O—N bond, and with the proviso that the bond to Y cannot be an O—N bond;
R1 is selected from the group consisting of hydrogen, linear or branched C$_{1-4}$ alkyl and saturated monocyclic C$_{3-4}$ cycloalkyl, wherein said linear or branched C$_{1-4}$ alkyl and saturated monocyclic C$_{3-4}$ cycloalkyl can be optionally substituted with one or more halogen;
R2 is selected from the group consisting of linear or branched C$_{1-6}$ alkyl, saturated monocyclic C$_{3-6}$ cycloalkyl, oxetanyl, tetrahydrofuranyl and tetrahydropyranyl, all of which can optionally be substituted with one or more halogen;
or a pharmaceutically acceptable salt thereof.
2. The compound according to claim 1, wherein ring A is a 6 membered heteroaromatic ring.
3. The compound according to claim 1, wherein Ring B is a 5 membered heteroaromatic ring.
4. The compound according to claim 1, wherein Ring B is a 6 membered heteroaromatic ring.

5. The compound according to claim 1, wherein said 5 membered heteroaromatic ring is pyrazolyl.

6. The compound according to claim 1, wherein said 6 membered heteroaromatic ring is pyridinyl or pyrazinyl.

7. The compound according to claim 1, wherein R1 is a linear or branched $C_{1-4}$ alkyl.

8. The compound according to claim 1, wherein R1 is methyl.

9. The compound according to claim 1, wherein R2 is a linear or branched $C_{1-6}$ alkyl.

10. The compound according to claim 1, wherein R2 is selected from methyl, ethyl and isopropyl.

11. The compound according to claim 1, wherein said compound is selected from the list consisting of
  1. $2^1$-isopropyl-$2^3$-methyl-$2^1$H-6,11-dioxa-3-aza-2(5,7)-pyrazolo [4,3-b]pyridina-1,5(3,2)-dipyridinacycloundecaphane;
  2. $2^1$-isopropyl-$2^3$-methyl-$2^1$H-6,12-dioxa-3-aza-2(5,7)-pyrazolo [4,3-b]pyridina- 1,5(3,2)-dipyridinacyclododecaphane;
  3. $2^1$-isopropyl-$2^3$-methyl-$2^1$H-6,10-dioxa-3-aza-2(5,7)-pyrazolo [4,3-b]pyridina- 1,5(3,2)-dipyridinacyclodecaphane;
  4. $2^1$-isopropyl-$2^3$-methyl-$2^1$H-6,9,12-trioxa-3-aza-2(5,7)-pyrazolo[4,3-b]pyridina-1,5(3,2)-dipyridinacyclododecaphane;
  5. $2^1$-isopropyl-$2^3$-methyl-$2^1$H,$5^1$H-11-oxa-3-aza-2(5,7)-pyrazolo[4,3-b]pyridina-1(3,2)-pyridina-5(5,1)-pyrazolacycloundecaphane;
  6. $2^1$-isopropyl-$2^3$-methyl-$2^1$H-6,11-dioxa-3-aza-2(5,7)-pyrazolo[4,3-b]pyridina-1(3,2),5(2,3)-dipyridinacycloundecaphane;
  7. $2^1,2^3$-dimethyl-$2^1$H-6,11-dioxa-3-aza-2(5,7)-pyrazolo[4,3-b]pyridina-1,5(3,2)-dipyridinacycloundecaphane;
  8. $2^1$-ethyl-$2^3$-methyl-$2^1$H-6,11-dioxa-3-aza-2(5,7)-pyrazolo[4,3-b]pyridina-1,5(3,2)-dipyridinacycloundecaphane;
  9. $2^1$-isopropyl-$2^3$-methyl-$2^1$H,$5^1$H-10-oxa-3-aza-2(5,7)-pyrazolo[4,3-b]pyridina-1(3,2)-pyridina-5(5,1)-pyrazolacyclodecaphane;
  10. $2^1$-isopropyl-$2^3$-methyl-$2^1$H-6,11-dioxa-3-aza-2(5,7)-pyrazolo[4,3-b]pyridina-5(2,3)-pyrazina-1(3,2)-pyridinacycloundecaphane;
  or a pharmaceutically acceptable salt of any of these compounds.

12. A pharmaceutical composition comprising a therapeutically effective amount of a compound of claim 1, or a pharmaceutically acceptable salt thereof, and one or more pharmaceutically acceptable carriers, diluents and/or excipients.

13. A method for the treatment of a neurodegenerative disorder, selected from the group consisting of Alzheimer's Disease, Parkinson's Disease and Huntington's Disease, which method comprises the administration of a therapeutically effective amount of a compound according to claim 1, or a pharmaceutically acceptable salt thereof, to a patient in need thereof.

14. The pharmaceutical composition of claim 12, further comprising a second compound, which compound is useful in the treatment of a psychiatric disorder.

15. The pharmaceutical composition according to claim 14, wherein said second compound has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

16. The pharmaceutical composition according to claim 14, wherein said second compound is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

17. The method of claim 13, further comprising administering a therapeutically effective amount of a second compound, which compound is useful in the treatment of a psychiatric disorder; to a patient in need thereof.

18. The method according to claim 17, wherein said second compound, which compound is useful in the treatment of a psychiatric disorder, has a pharmacological activity selected from one or more of the following mechanisms: antagonist/inverse agonist/negative modulator/partial agonist/inhibitor of one or more of the targets dopamine D1 receptor, dopamine D2 receptor, dopamine D3 receptor, phosphodiesterase PDE10, serotonin 5-HT2A receptor, serotonin 5-HT6 receptor, and glycine transporter GlyT1; or agonist/positive modulator/partial agonist of one or more of the targets KCNQ channels, NMDA receptor, AMPA receptor and nicotinic alpha-7 receptor.

19. The method according to claim 18, wherein said second compound, which compound is useful in the treatment of a psychiatric disorder, is selected from the list comprising clozapine, risperidone, paliperidone, olanzapine, quetiapine, amisulpride, ziprasidone, aripiprazole, brexpiprazole, asenapine, haloperidole, iloperidone, lurasidone, chlorpromazine, blonanserin, perphenazine, levomepromazine, sulpiride, fluphenazine, zuclopenthixol, flupenthixol and cariprazine.

* * * * *

UNITED STATES PATENT AND TRADEMARK OFFICE
CERTIFICATE OF CORRECTION

PATENT NO. : 10,618,913 B2
APPLICATION NO. : 16/217754
DATED : April 14, 2020
INVENTOR(S) : Karsten Juhl et al.

It is certified that error appears in the above-identified patent and that said Letters Patent is hereby corrected as shown below:

In the Claims

Claim 11, at Column 101, Lines 33-34, compound 7, please replace the "." after "2¹" with a ","

Signed and Sealed this
Twenty-sixth Day of May, 2020

Andrei Iancu
*Director of the United States Patent and Trademark Office*